US009617231B2

(12) United States Patent
Jorgensen et al.

(10) Patent No.: US 9,617,231 B2
(45) Date of Patent: *Apr. 11, 2017

(54) DEUTERATED 1-PIPERAZINO-3-PHENYL INDANES FOR TREATMENT OF SCHIZOPHRENIA

(71) Applicant: H. Lundbeck A/S, Valby (DK)

(72) Inventors: Morten Jorgensen, Bagsvaerd (DK); Peter Hongaard Andersen, Farum (DK); Klaus Gjervig Jensen, Kobenhavn K (DK)

(73) Assignee: H. LUNDBECK A/S, Valby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/941,800

(22) Filed: Nov. 16, 2015

(65) Prior Publication Data

US 2016/0068497 A1 Mar. 10, 2016

Related U.S. Application Data

(63) Continuation of application No. 14/656,925, filed on Mar. 13, 2015, now Pat. No. 9,216,961, which is a continuation of application No. 13/924,849, filed on Jun. 24, 2013, now Pat. No. 9,012,453, which is a continuation of application No. 13/527,364, filed on Jun. 19, 2012, now Pat. No. 8,575,174.

(60) Provisional application No. 61/537,103, filed on Sep. 21, 2011, provisional application No. 61/498,651, filed on Jun. 20, 2011.

(51) Int. Cl.

| | |
|---|---|
| C07D 295/073 | (2006.01) |
| C07B 59/00 | (2006.01) |
| C07D 241/04 | (2006.01) |
| A61K 31/451 | (2006.01) |
| A61K 31/454 | (2006.01) |
| A61K 31/4545 | (2006.01) |
| A61K 31/495 | (2006.01) |
| A61K 31/496 | (2006.01) |
| A61K 31/519 | (2006.01) |
| A61K 31/551 | (2006.01) |
| A61K 31/554 | (2006.01) |
| C07C 45/61 | (2006.01) |
| C07C 45/67 | (2006.01) |

(52) U.S. Cl.
CPC ........ C07D 295/073 (2013.01); A61K 31/451 (2013.01); A61K 31/454 (2013.01); A61K 31/4545 (2013.01); A61K 31/495 (2013.01); A61K 31/496 (2013.01); A61K 31/519 (2013.01); A61K 31/551 (2013.01); A61K 31/554 (2013.01); C07B 59/002 (2013.01); C07C 45/61 (2013.01); C07C 45/67 (2013.01); C07D 241/04 (2013.01)

(58) Field of Classification Search
CPC .................................................. C07D 295/073
See application file for complete search history.

(56) References Cited

U.S. PATENT DOCUMENTS

| | | | |
|---|---|---|---|
| 4,684,650 A | 8/1987 | Bogeso | |
| 5,807,855 A | 9/1998 | Bøgesø et al. | |
| 6,221,335 B1 | 4/2001 | Foster | |
| 7,456,317 B2 | 11/2008 | Gant et al. | |
| 7,528,131 B2 | 5/2009 | Persichetti et al. | |
| 7,648,991 B2 | 1/2010 | Bang-Andersen et al. | |
| 7,678,914 B2 | 3/2010 | Tung | |
| 7,863,274 B2 | 1/2011 | Tung | |
| 8,263,601 B2 | 9/2012 | Tung et al. | |
| 8,278,460 B2 | 10/2012 | Liu et al. | |
| 8,575,174 B2 | 11/2013 | Jorgensen et al. | |
| 9,012,453 B2 | 4/2015 | Jorgensen et al. | |
| 2006/0281758 A1 | 12/2006 | Bang-Andersen et al. | |
| 2006/0281759 A1 | 12/2006 | de Diego et al. | |
| 2008/0153847 A1 | 6/2008 | Dahl et al. | |
| 2008/0269248 A1 | 10/2008 | Nielsen et al. | |
| 2009/0306092 A1 | 12/2009 | Olsen et al. | |
| 2010/0069676 A1 | 3/2010 | Dahl et al. | |
| 2010/0324291 A1 | 12/2010 | Lopez de Diego et al. | |
| 2011/0053957 A1 | 3/2011 | Lopez de Diego et al. | |
| 2011/0178094 A1 | 7/2011 | Holm et al. | |
| 2011/0207744 A1 | 8/2011 | Olsen et al. | |
| 2015/0307458 A1 | 10/2015 | Jorgensen et al. | |

FOREIGN PATENT DOCUMENTS

| | | |
|---|---|---|
| CN | 101935305 | 1/2011 |
| CN | 102020522 A | 4/2011 |
| EP | 0035363 | 5/1985 |

(Continued)

OTHER PUBLICATIONS

Balsara et al., "Effect of Drugs Influencing central serotonergic mechanisms on haloperidol-Induced Catalepsy," Psychoparmacology, vol. 62, pp. 67-69 (1979).
Blake et al., "Studies with Deuterated Drugs," Journal of Pharmaceutical Sciences, vol. 64, pp. 367-391 (1975).
Bøgesø et al., "3-Phenyl-1-indanamines, Potential Antidepressant Activity and potent Inhibition of Dopamine, Norepinephrine, and Serotonin Uptake," J. Med. Chem, vol. 28, pp. 1817-1828 (1985).
Bøgesø et al., "Enahnced D1 affinity in a Series of Piperazine Ring Substituted 1-Piperazino-3-Arylindans with Potential Atypical Antipsychotic Activity," J. MEd Chem, vol. 38, pp. 4380-4392 (1995).

(Continued)

Primary Examiner — Noble Jarrell
Assistant Examiner — John S Kenyon
(74) Attorney, Agent, or Firm — Wilmer Cutler Pickering Hale and Dorr, LLP

(57) ABSTRACT

The present invention relates to deuterated 1-piperazino-3-phenyl-indanes and salts thereof with activity at dopamine receptors $D_1$ and $D_2$ as well as the $5HT_2$ receptors in the central nervous system, to medicaments comprising such compounds as active ingredients, to the use of such compounds in the treatment of diseases in the central nervous system, and to methods of treatment comprising administration of such compounds.

3 Claims, 12 Drawing Sheets

(56) References Cited

FOREIGN PATENT DOCUMENTS

| EP | 638073 | 6/2000 |
|---|---|---|
| WO | WO-92/10192 A1 | 6/1992 |
| WO | WO 93/22293 | 11/1993 |
| WO | WO-95/26325 A2 | 10/1995 |
| WO | WO 2005/016900 | 2/2005 |
| WO | WO 2005/016901 | 2/2005 |
| WO | WO 2006/086984 | 8/2006 |
| WO | WO 2007/016431 | 2/2007 |
| WO | WO 2008/025361 | 3/2008 |
| WO | WO 2008/156632 | 12/2008 |
| WO | WO 2010/062656 A2 | 6/2010 |
| WO | WO 2011/022682 A1 | 2/2011 |
| WO | WO 2011/059080 A1 | 5/2011 |

OTHER PUBLICATIONS

Bøgesø K. "Drug hunting. The Medicinal Chemistry of 1-Piperazino-3-Phenylindans and related Compounds," Printed in Denmark by Norhaven, Copenhagen Denmark, 1998.

Buteau, "Deuterated Drugs Unexpected Nonobvious?," 10 J. High Tech. L., vol. 22, pp. 22-74 (2009).

Carlsson Arvid, "Antipsychotic Drugs, Neurotransmitters, and Schizophrenia," Am. J. Psychiatry, vol. 135, pp. 164-173 (1978).

Eder, Derek, "CEE-03-310 CENes Pharmaceuticals," Current Opinion in Investigational Drugs, vol. 3(2), pp. 284-288 (2002).

Fisher et al., "The Complexities inherent in attempts to decrease drug clearance by blocking sites of CYP-mediated metabolism," Current Opinion in Drug Discovery & Development, vol. 9(1), pp. 101-109 (2006).

Foster, Allan, "Deuterium Isotope Effects in the Metanolism of Drugs and Xenobiotics: Implications for drug Design," Adv. Drug. Res., vol. 14, pp. 1-40 (1985).

Fukuto et al., "Determination of the Mechanism of Demethylenation of (Methylenedioxy)phenyl compounds by Cytochrome P450 using deuterium isotope effects," J. Med. Chem, vol. 34, pp. 2871-2876 (1991).

Geyer MA and Moghaddam B. Animal Models Relevant to Schizophrenia Disorders. Neuropsychopharmacology: The Fifth Generation of Progress. Edited by Kenneth L. Davis, Dennis Charney, Joseph T. Coyle, and Charles Nemeroff. American College of Neuropsychopharmacology 2002, 689-701.

Gleason SD and Shannon HE. Blockade of phencyclidine-induced hyperlocomotion by olanzapine, clozapine and serotonin receptor subtype selective antagonists in mice. Psychopharmacology (Berl). Jan. 1997;129(1):79-84.

Harbeson et al, "Deuterium in Drug Discovery and development," Ann. Rep. Med Chem, vol. 46, pp. 404-418 (2011).

International Search Report and Written Opinion maild on Nov. 15, 2012, for International Application No. PCT/IB2012/001386 filed Jun. 19, 2012 (9 pages).

Jackson DM et al., "Dopamine receptor antagonists block amphetamine and phencyclidine-induced motor stimulation in rats," Pharmacol Biochem Behav. Jun. 1994;48(2):465-71.

Jentsch JD and Roth RH., "The neuropsychopharmacology of phencyclidine: from NMDA receptor hypofunction to the dopamine hypothesis of schizophrenia," Neuropsychopharmacology 20(3):201-25 (1999).

Kundu et al., "Hydroacylation of 2-Vinyl Benzaldehyde Systems: An Efficient Method for the Synthesis of Chiral 3-Substituted Indanones," JACS, vol. 127, pp. 16042-16043 (2005).

Kushner et al., "Pharmacological uses and persceptives of heavy water and deuterated compounds," Can. J. Physiol Phamacol, vol. 77, pp. 79-88 (1999).

Mamada et al., "Short Communication. Pharmacokinetic Equivalence of Deuterium-Labeled and Unlabeled Phenytoin," Drug metabolism and Disposition, vol. 14, pp. 509-511 (1986).

Minatti et al., "Synthesis of Chiral 3-Substituted Indanones via an Enantioslective Reductive-Heck Reaction," J. Org. Chem, vol. 72, pp. 9253-9258 (2007).

Morgan et al., "Evaluation of stable isotope-labeled probes in the study of solvent pharmacokinetics in human subjects," Int Arch Environ health (1993), vol. 65, pp. S139-S142 (1993).

Mutlib, Abdul, "Application of Stable Isotope-Labeled Compounds in Metabolism and in Metabolism-Mediated toxicity studies," Chem Res. Toxicol, vol. 21, pp. 1672-1689 (2008).

No Author Listed, "Bipolar disorder," May Clinic, retrieved from the internet: URL<http://www.mayoclinic.com/health/bipolar-disorder/DS00356/METHOD=print&DSECTION=all.>, Jan. 2012 (20 pages).

No Author Listed, "Psychosis—information prescription," United Kingdom National Health Service, retrieved from the internet: URL<http://www.nhs.uk/Pages/Preview.aspx?site=Psychosis&print=635180718877108038&JScript=1.>, Oct. 22, 2013 (12 pages).

No Author Listed, "Psychosis," PubMed Health, retrieved from the internet: URL<http://www.ncbi.nlm.nih.gov/pubmedhealth/PMH0002520/.>, Mar. 7, 2012 (2 pages).

No Author Listed, "Schizophrenia," Mayo Clinic, retrieved from the internet: URL<http://www.mayoclinic.com/health/schizophrenia/DS00196/METHOD=print&DSECTION=all.>, Jan. 2012 (10 pages).

Sax, N. Irving, et al., Hawley's Condensed Chemical Dictionary, 11th edition, Van Nostrand Reinhold, 1987, p. 355.

Seeman, Philip, "Dopamine Receptor and psychosis," Science and Medicine, vol. 2, pp. 28-37 (1995).

Shao et al, "The Kinetic isotope effect in the search for deuterated drugs," Drug News & Perspectives, vol. 23(6), pp. 398-404 (2010).

Silverman, "7.4. Pathways for drug deactivation and elimination," The Organic Chemistry of Drug Design and Drug action, Second Edition, Elsevier Academic Press, pp. 415-427 (2004).

Simeone et al., "Palladium on carbo as a precatalyst for Suzuki-Miyuara cross-coupling of aryl chlorides," Tetrahedron, vol. 63, pp. 12646-12654 (2007).

Streeter et al., "Single-dose toxicokinetics of N-nitrosomethylethylamine and N-nitrosomethyl (2,2,2-trideuterioethyl)amine in the rat," Arch Toxicol, vol. 64, pp. 109-115 (1990).

Takagi et al., "Palladium-Catalyzed Cross-coupling reaction of Bis(pimacolato)diboron with 1-Alkenyl Halides or triflates: Convenient Synthesis of Unsymmetrical 1,3-Dienes via the Borylation-Coupling Sequence," J. Am. Chem Soc, vol. 124, pp. 8001-8006 (2002).

Weiden, Peter, "EPS Profiles: The Atypical Antipsychotics are not the same," J. Psychiatr. Pract, vol. 13(1), pp. 13-24 (2007).

Willner, Paul, "Dopamine and Depression: A review of recent evidence. I. Empirical Studies," Brain Research Reviews, vol. 6, pp. 211-224 (1983).

HLM incubated with 10 μM
Compound (X), Compound (II) or Compound (IV)

HLM incubated with 10 μM
Compund (X) and Compound (III)

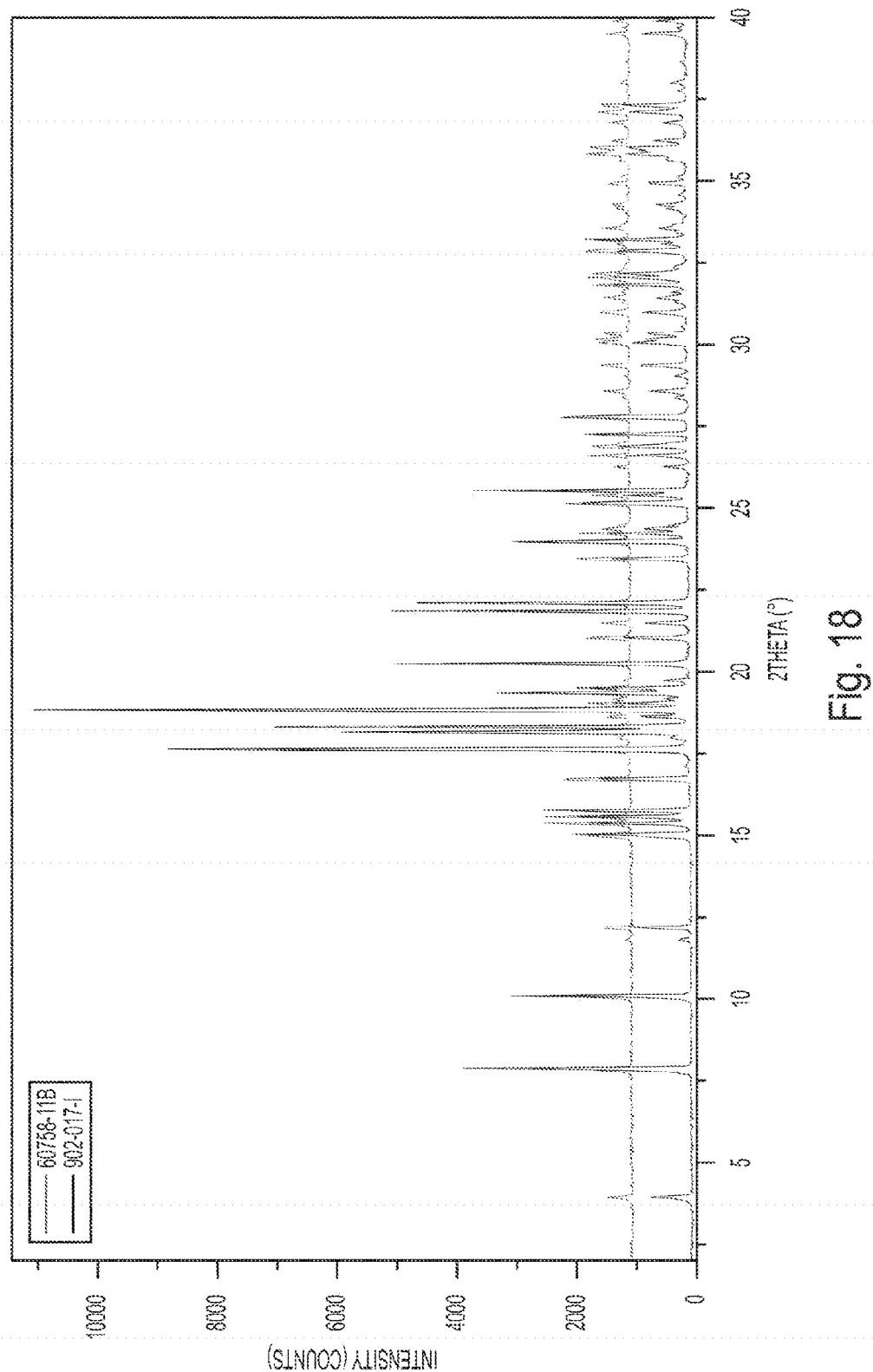

DEUTERATED 1-PIPERAZINO-3-PHENYL INDANES FOR TREATMENT OF SCHIZOPHRENIA

This application is a continuation of U.S. patent application Ser. No. 14/656,925, filed Mar. 13, 2015 and issued as U.S. Pat. No. 9,216,961 on Dec. 22, 2015, which is a continuation of U.S. patent application Ser. No. 13/924,849, filed Jun. 24, 2013 and issued as U.S. Pat. No. 9,012,453 on Apr. 21, 2015, which is a continuation of U.S. patent application Ser. No. 13/527,364, filed Jun. 19, 2012 and issued as U.S. Pat. No. 8,575,174 on Nov. 5, 2013, which claims priority to U.S. Provisional Application No. 61/498,651, filed on Jun. 20, 2011, and 61/537,103, filed on Sep. 21, 2011, the entirety of each of which is incorporated herein by reference.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

FIELD OF THE INVENTION

The present invention relates to deuterated 1-piperazino-3-phenyl-indanes and salts thereof with activity at dopamine $D_1$ and $D_2$ receptors as well as the serotonin $5HT_2$ receptors in the central nervous system, to medicaments comprising such compounds as active ingredients, and to the use of such compounds in the treatment of diseases in the central nervous system.

BACKGROUND OF THE INVENTION

Throughout this application, various publications are referenced in full. The disclosures of these publications are hereby incorporated by reference into this application to describe more fully the state of the art to which this invention pertains.

4-((1R,3S)-6-Chloro-3-phenyl-indan-1-yl)-1,2,2-trimethyl-piperazine and salts thereof, pharmaceutical compositions containing these salts and the medical use thereof, including treatment of schizophrenia or other diseases involving psychotic symptoms, are disclosed in WO2005/016900. 4-((1R,3S)-6-Chloro-3-phenyl-indan-1-yl)-1,2,2-trimethyl-piperazine has the general formula (X), hereinafter referred to as Compound (X)

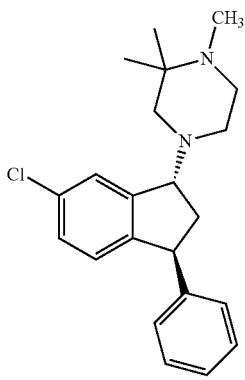

(X)

EP 638 073 recites a group of trans isomers of 3-aryl-1-(1-piperazinyl)indanes substituted in the 2- and/or 3-position of the piperazine ring. The compounds are described as having high affinity for dopamine $D_1$ and $D_2$ receptors and the $5\text{-}HT_2$ receptors and are suggested to be useful for treatment of several diseases in the central nervous system, including schizophrenia.

The enantiomer of formula (X) above has been described by Bøgesø et al. in *J. Med. Chem.*, 1995, 38, page 4380-4392, in the form of the fumarate salt, see table 5, compound (−)-38. This publication concludes that the (−)-enantiomer of compound 38 is a potent $D_1/D_2$ antagonist showing some $D_1$ selectivity in vitro. The compound is also described as a potent $5\text{-}HT_2$ antagonist. It is also mentioned that the compound does not induce catalepsy in rats.

The aetiology of schizophrenia is not known, but the dopamine hypothesis of schizophrenia (Carlsson, *Am. J. Psychiatry* 1978, 135, 164-173), formulated in the early 1960s, has provided a theoretical framework for understanding the biological mechanisms underlying this disorder. In its simplest form, the dopamine hypothesis states that schizophrenia is associated with a hyperdopaminergic state, a notion which is supported by the fact that all antipsychotic drugs on the market today exert some dopamine $D_2$ receptor antagonism (Seeman *Science and Medicine* 1995, 2, 28-37). However, whereas it is generally accepted that antagonism of dopamine $D_2$ receptors in the limbic regions of the brain plays a key role in the treatment of positive symptoms of schizophrenia, the blockade of $D_2$ receptors in striatal regions of the brain causes extrapyramidal symptoms (EPS). As described in EP 638 073 a profile of mixed dopamine $D_1/D_2$ receptor inhibition has been observed with some so-called "atypical" antipsychotic compounds, in particular with clozapine (8-chloro-11-(4-methylpiperazin-1-yl)-5H-dibenzo[b,e][1,4]diazepine), used in treatment of schizophrenic patients.

Further, selective $D_1$ antagonists have been connected to treatment of sleep disorders and alcohol abuse (D. N. Eder, *Current Opinion in Investigational Drugs*, 2002 3(2):284-288).

Dopamine may also play an important role in the aetiology of affective disorders (P. Willner, *Brain. Res. Rev.* 1983, 6, 211-224, 225-236 and 237-246; Bøgesø et al, *J. Med. Chem.*, 1985, 28, 1817-1828).

In EP 638 073 is described how compounds having affinity for $5\text{-}HT_2$ receptors, in particular $5\text{-}HT_{2A}$ receptor antagonists, have been suggested for treatment of different diseases, such as schizophrenia including the negative symptoms in schizophrenic patients, depression, anxiety, sleep disturbance, migraine attacks and neuroleptic-induced parkinsonism. $5\text{-}HT_{2A}$ receptor antagonism has also been suggested to reduce the incidence of extrapyramidal side effects induced by classical neuroleptics (Balsara et al. *Psychopharmacology* 1979, 62, 67-69).

An isotopic substitution of one or more hydrogen atoms (H) by deuterium atoms (D) in a compound may give rise to a kinetic isotope effect which may influence the reaction rate, e.g. metabolism of the compound. This is particularly the case when the isotopic replacement is in a chemical bond that is broken or formed in a rate limiting step. In such a case, the change is termed a primary isotope effect. When the isotopic substitution(s) are not involved in one or more bonds that are broken a smaller rate change, termed the secondary isotope effect may be observed.

SUMMARY OF THE INVENTION

The present invention provides compounds wherein one or more hydrogen atoms atoms (H) in one or more of the metabolic sites M1, M2 and M3 of Compound (X) have been substituted by deuterium atoms (D).

In one aspect, the invention provides a compound of formula Y:

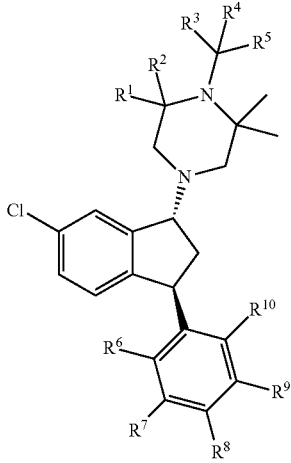

(Y)

wherein, $R^1$-$R^{10}$ are independently hydrogen or deuterium, and wherein at least one of $R^1$-$R^{10}$ comprises at least about 50% deuterium, or a pharmaceutically acceptable acid addition salt thereof.

In another aspect, the invention provides pharmaceutical compositions comprising a compound of formula (Y) and one or more pharmaceutically acceptable carriers, diluents, or excipients.

In another aspect, the invention provides for uses of a compound of formula (Y) or a pharmaceutical composition comprising a compound of formula (Y) in the treatment of psychosis, other diseases involving psychotic symptoms, psychotic disorders or diseases that present with psychotic symptoms.

In yet another aspect, the invention provides for the manufacture of a medicament comprising a compound of formula (Y) for treatment of psychosis, other diseases involving psychotic symptoms, psychotic disorders or diseases that present with psychotic symptoms.

In still another aspect, the invention provides for methods of treating psychosis, other diseases involving psychotic symptoms, psychotic disorders or diseases that present with psychotic symptoms comprising administration of an effective amount of a compound of formula (Y) or a pharmaceutically composition comprising a compound of formula (Y) to a subject in need thereof.

In still another aspect, the invention provides a compound of formula

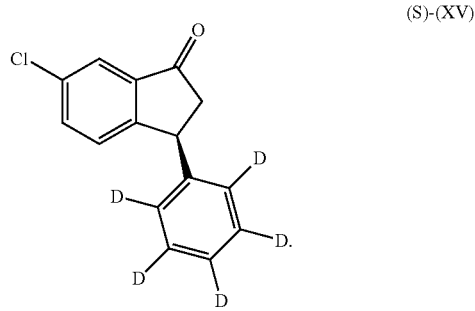

(S)-(XV)

In still another aspect, the invention provides a process for the preparation of compound

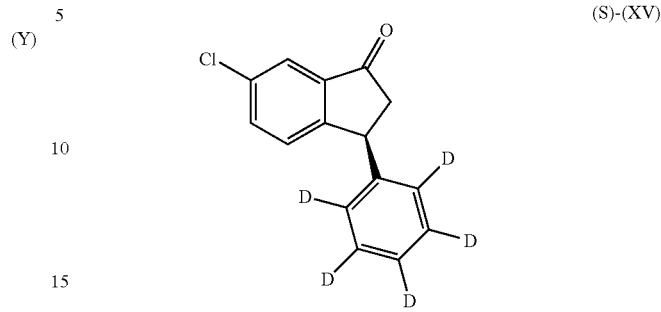

(S)-(XV)

comprising treating compound (XIV) with [(S)-BINAP]Rh (I)BF$_4$.

In still another aspect, the invention provides a process for the preparation of compound (1R,3S)-(IV) tartrate comprising, treatment of racemic trans-1-(6-chloro-3-phenyl(d$_5$)-indan-1-yl)-1(d$_3$), 2,2-trimethyl-piperazine with L-(+)-tartaric acid.

Still other objects and advantages of the invention will become apparent to those of skill in the art from the disclosure herein, which is simply illustrative and not restrictive. Thus, other embodiments will be recognized by the skilled artisan without departing from the spirit and scope of the invention.

BRIEF DESCRIPTION OF THE FIGURES

FIG. 18 shows X-ray diffractograms on two batches of hydrogen tartrate salt of Compound (IV).

DETAILED DESCRIPTION OF THE INVENTION

Atypical antipsychotics have been the subject of numerous studies by the pharmaceutical industry, and have shown promise in treating mental disorders such as schizophrenia, bipolar disorder, dementia, anxiety disorder and obsessive-compulsive disorder (OCD). The mechanism of action of these agents remains unknown; however all antipsychotics work to some degree on the dopamine system. Most atypical antipsychotics exhibit activity at dopamine subtype receptors 1 and 2 ($D_1$ and $D_2$, respectively), and at the serotonin receptors subtype 2 ($5-HT_2$). In some cases, the "atypical" designation was assigned to antipsychotics that did not induce extrapyramidal side effects; however it has been shown that some atypical antipsychotics still induce extrapyramidal side effects, albeit to a lesser degree that that observed with typical antipsychotics (Weiden, P. J., "EPS profiles: the atypical antipsychotics are not all the same" *J. Psychiatr. Pract.* 2007, 13(1): 13-24; herein incorporated by reference in its entirety). Approved atypical antipsychotics include, for example, amisulpride (Solian), aripiprazole (Abilify), asenapine (Saphris), blonanserin (Lonasen), clotiapine (Entumine), clozapine (Clozaril), iloperidone (Fanapt), lurasidone (Latuda), mosapramine (Cremin), olanzapine (Zyprexa), paliperidone (Invega), perospirone (Lullan), quetiapine (Seroquel), remoxipride (Roxiam), risperidone (Risperdal), sertindole (Serdolect), supliride (Sulpirid, Eglonyl), ziprasidone (Geodon, Zeldox), and zotepine (Nipolept). Several others are currently under development. Because the mechanism of atypical antipsychotics is not well understood, side effects associated with these drugs have been difficult to design around. Thus, there is a need for additional antipsychotic therapies with potential for reduced side effect and/or improved therapeutic profile relative to existing therapies.

In one aspect, the present invention provides compounds wherein one or more hydrogen atoms (H) in one or more of the metabolic sites M1, M2 and M3 of Compound (X) have been substituted by deuterium atoms (D). Compound (X) and variants thereof are described in, for example U.S. Pat. Nos. 5,807,855; 7,648,991; 7,767,683; 7,772,240; 8,076,342; U.S. Patent Publication Nos. 2008/0269248; 2010/0069676; 2011/0178094; 2011/0207744; WO 2005/016900; EP 0 638 073; and *J. Med. Chem.* 1995, 38, 4380-4392; each herein incorporated by reference in its entirety.

Figure 1:
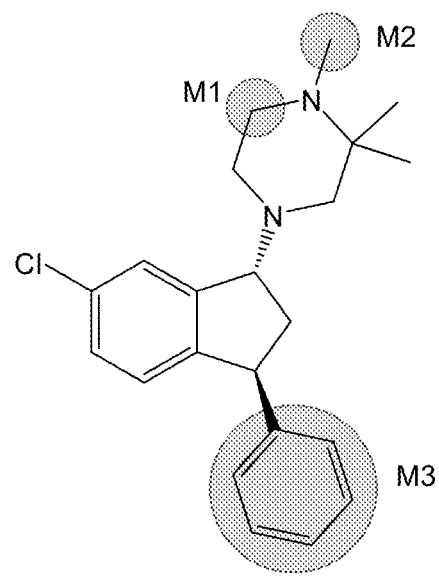
FIG. 1 shows major metabolic sites of Compound (X).

The kinetic isotope effect may potentially influence the rate of metabolism at one or more of the metabolic sites M1, M2, and M3 indicated in FIG. 1. The inventors of the present invention have identified three major metabolic sites of 4-((1R,3S)-6-chloro-3-phenyl-indan-1-yl)-1,2,2-trimethyl-piperazine (Compound (X)) denoted herein as M1, M2 and M3 and indicated in FIG. 1.

Deuteration of a compound at a site subject to oxidative metabolism may, in some cases reduce the rate of metabolism for a compound due to the primary isotope effect. If the C—H bond cleavage step is rate limiting, a significant isotope effect may be observed. However, if other steps drive the rate of metabolism for a compound, the C—H bond cleavage step is not rate limiting and the isotope effect may be of little significance. Additionally, a negative isotope effect can be observed where reaction rate is increased upon substitution with deuterium. Thus, incorporation of deuterium at a site subject to oxidative enzymatic metabolism does not predictably impact pharmacokinetics (See, for example, U.S. Pat. No. 7,678,914; *Drug Metab. Dispos.* 1986, 14, 509; *Arch. Toxicol.* 1990, 64, 109; *Int. Arch. Occup. Environ. Health* 1993, 65(Suppl. 1): 5139; each herein incorporated by reference in its entirety). The impact of deuterium incorporation is unpredictable does not work for many drugs or classes of drugs. Decreased metabolic clearance has been observed with some deuterated compounds relative to non-deuterated derivatives; whereas metabolism of other compounds has been unimpacted. Examples of studies indicating lack of predictability regarding deuterium incorporation include U.S. Pat. No. 6,221,335; *J. Pharm. Sci.* 1975, 64, 367-391; *Adv. Drug. Res.* 1985, 14, 1-40; *J. Med. Chem.* 1991, 34, 2871-2876; *Can. J. Physiol. Pharmacol.* 1999, 79-88; Silverman, R. B., The Organic Chemistry of Drug Design and Drug Action, $2^{nd}$ Ed. (2004), 422; *Curr. Opin. Drug Dev.* 2006, 9, 101-109; *Chemical Res. Tox.* 2008, 1672; Harbeson, S. L and Tung, R. D. "Deuterium in Drug Discovery and Development," in *Ann. Rep. Med. Chem.* 2011, 46, 404-418; each herein incorporated by reference in its entirety. Even incorporation deuterium at known sites of metabolism has an unpredictable impact on metabolic profile. Metabolic switching may result wherein the metabolic profile of a particular drug is changed due to deuterium incorporation, thus leading to different proportions of (or different) metabolites than observed with a non-deuterated analog of the same drug. The new metabolic profile may result in a distinct toxicological profile of the deuterated analog. Adding to the potential complications of deuterium incorporation is the possibility of deuterium/hydrogen exchange in the physiological environment (*Adv. Drug. Res.* 1985, 14, 1-40; herein incorporated by reference in its entirety).

In some embodiments, isotopic substitution of one or more hydrogen atoms in Compound (X) by deuterium atoms has given rise to a kinetic isotope effect that influences the rate of metabolism.

Figure 2:
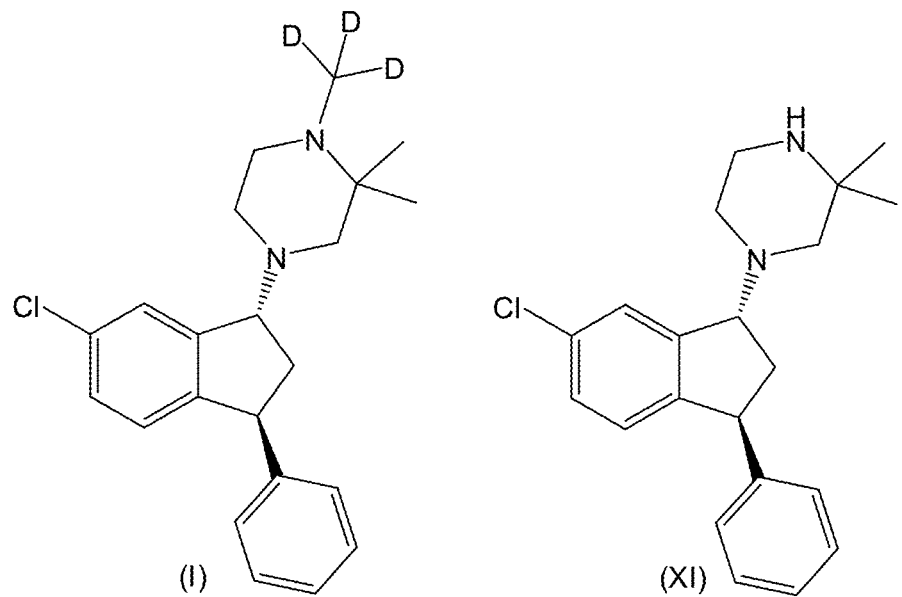
FIG. 2 shows Compound (I) and Compound (XI), each as the (1R,3S)-enantiomer.

The isotopic substitution of hydrogen atoms in Compound (X) by deuterium atoms results in less metabolism of the deuterated compound as shown to occur in dog hepatocytes where for instance an approximately 50% decrease in formation of the desmethyl metabolite (Compound (XI)) from Compound (I) (FIG. 2) was noted in comparison to the formation of Compound (XI) from the metabolism of Compound (X).

Deuteration of the free phenyl, optionally in combination with deuteration of the 1-methyl group (Compound (II) and (IV)), surprisingly reduces the amount of the desmethyl metabolite produced in human liver microsomes as compared to the non-deuterated compound (Compound (X)). Also surprisingly, deuteration of the 1-methyl group impacted metabolism in dog but not human hepatocytes, thus indicative of the unpredictability of deuteration on pharmacological properties.

The effect of the reduced metabolism is higher bioavailability of the deuterated, parent compound and less metabolite formation. Without being bound by theory, based on the results described in the experimental section of this application the same effect is expected to show up after multiple dosing in humans, allowing for lower doses to be administered to humans i.e. less burden to the entire body, e.g. the liver, and a less frequent dosing.

The desmethyl metabolite (Compound (XI)) is known to have hERG affinity and thus potentially contribute to QTc prolongation. As mentioned above, deuteration of the free phenyl optionally in combination with deuteration of the 1-methyl group (Compound (II) and (IV)), surprisingly reduces the amount of the desmethyl metabolite produced in human liver microsomes as compared to the non-deuterated compound (Compound (X)). Accordingly and without being bound by theory, it is anticipated that there will be less interaction with the hERG channel and resultant lower burden on the heart when dosing the deuterated variants of Compound (X) [e.g., compounds of formula (Y)] compared to when dosing Compound (X).

The invention is further detailed in the exemplary embodiments provided herein.

Definitions

The term "compound(s) of the invention" as used herein means Compounds (Y), (I), (II), (III), (IV), (V), (VI), and/or (VII), and may include salts, hydrates and/or solvates thereof. The compounds of the present invention are prepared in different forms, such as salts, hydrates, and/or solvates, and the invention includes compositions and methods encompassing all variant forms of the compounds.

The term "composition(s) of the invention" as used herein means compositions comprising Compounds (Y), (I), (II), (III), (IV), (V), (VI), and/or (VII), or salts, hydrates and solvates thereof. The compositions of the invention may further comprise one or more chemical components such as, for example, excipients, diluents, vehicles or carriers.

The term "method(s) of the invention" as used herein means methods comprising treatment with the compounds and/or compositions of the invention.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

An "effective amount", "sufficient amount" or "therapeutically effective amount" as used herein is an amount of a compound that is sufficient to effect beneficial or desired results, including clinical results. As such, the effective amount may be sufficient, for example, to reduce or ameliorate the severity and/or duration of an affliction or condition, or one or more symptoms thereof, prevent the advancement of conditions related to an affliction or condition, prevent the recurrence, development, or onset of one or more symptoms associated with an affliction or condition, or enhance or otherwise improve the prophylactic or therapeutic effect(s) of another therapy. An effective amount also includes the amount of the compound that avoids or substantially attenuates undesirable side effects.

As used herein and as well understood in the art, "treatment" is an approach for obtaining beneficial or desired results, including clinical results. Beneficial or desired clinical results may include, but are not limited to, alleviation or amelioration of one or more symptoms or conditions, diminution of extent of disease, a stabilized (i.e., not worsening) state of disease, preventing spread of disease, delay or slowing of disease progression, amelioration or palliation of the disease state and remission (whether partial or total), whether detectable or undetectable. "Treatment" can also mean prolonging survival as compared to expected survival if not receiving treatment.

The term "in need thereof" refers to the need for symptomatic or asymptomatic relief from a condition such as, for example, psychosis or a psychotic disorder. The subject in need thereof may or may not be undergoing treatment for conditions related to, for example, psychosis or a psychotic disorder.

The term "carrier" refers to a diluent, adjuvant, excipient, or vehicle with which a compound is administered. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in Remington: The Science and Practice of Pharmacy, 21$^{st}$ Edition (University of the Sciences in Philadelphia, ed., Lippincott Williams & Wilkins 2005). (hereby incorporated by reference in its entirety).

The terms "animal," "subject" and "patient" as used herein include all members of the animal kingdom including, but not limited to, mammals, animals (e.g., cats, dogs, horses, swine, etc.) and humans.

The term "isotopic variant" as used herein means a compound obtained by substituting one or more hydrogen in a parent compound not comprising deuterium atoms by deuterium atoms.

It is recognized that elements are present in natural isotopic abundances in most synthetic compounds, and result in inherent incorporation of deuterium. However, the natural isotopic abundance of hydrogen isotopes such as deuterium is immaterial (about 0.015%) relative to the degree of stable isotopic substitution of compounds indicated herein. Thus, as used herein, designation of an atom as deuterium at a position indicates that the abundance of deuterium is significantly greater than the natural abundance of deuterium. Any atom not designated as a particular isotope is intended to represent any stable isotope of that atom, as will be apparent to the ordinarily skilled artisan.

Compounds (Y) are isotopic variants of Compound (X).

In some embodiments, compounds (I), (II), (III), (IV), (V), (VI) and (VII) are isotopic variants of Compound (X).

M1 is a site of Compound (X) susceptible to metabolism; M1 consists of —$CH_2$— in the 6-position of the piperazine of Compound (X).

M2 is a site of compound (X) susceptible to metabolism; M2 consists of the N-bound methyl of the piperazine of Compound (X).

M3 is a site of Compound (X) susceptible to metabolism; M3 consists of the phenyl group of Compound (X).

Parent compound is the chemical compound which is the basis for its derivatives obtained either by substitution or breakdown, e.g. metabolic breakdown. In the context of the present invention the parent compound is the Active Pharmaceutical Ingredient (API).

In some embodiments, any atom not designated as deuterium is present at its natural isotopic abundance. In some embodiments, any hydrogen atom not designated as deuterium is present at less than 1% isotopic abundance of deuterium.

In one aspect, the invention provides a compound of formula (Y):

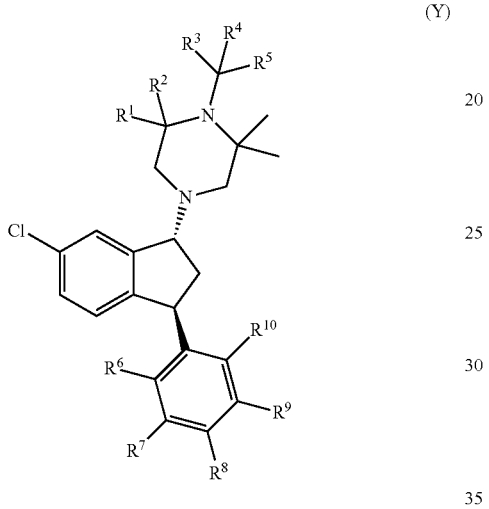

(Y)

wherein, $R^1$-$R^{10}$ are independently hydrogen or deuterium, wherein at least one of $R^1$-$R^{10}$ comprises at least about 50% deuterium, or a pharmaceutically acceptable acid addition salt thereof.

In another aspect, the invention provides pharmaceutical compositions comprising a compound of formula (Y) and one or more pharmaceutically acceptable carriers, diluents, or excipients.

In another aspect, the invention provides for uses of a compound of formula (Y) or a pharmaceutical composition comprising a compound of formula (Y) in the treatment of psychosis, other diseases involving psychotic symptoms, psychotic disorders or diseases that present with psychotic symptoms.

In yet another aspect, the invention provides for the manufacture of a medicament comprising a compound of formula (Y) for treatment of psychosis, other diseases involving psychotic symptoms, psychotic disorders or diseases that present with psychotic symptoms.

In still another aspect, the invention provides for methods of treating psychosis, other diseases involving psychotic symptoms, psychotic disorders or diseases that present with psychotic symptoms comprising administration of an effective amount of a compound of formula (Y) or a pharmaceutically composition comprising a compound of formula (Y).

In some embodiments, the compound is racemic. In some embodiments, the compound is enantiomerically enriched.

In some embodiments, the compound is selected from the group consisting of

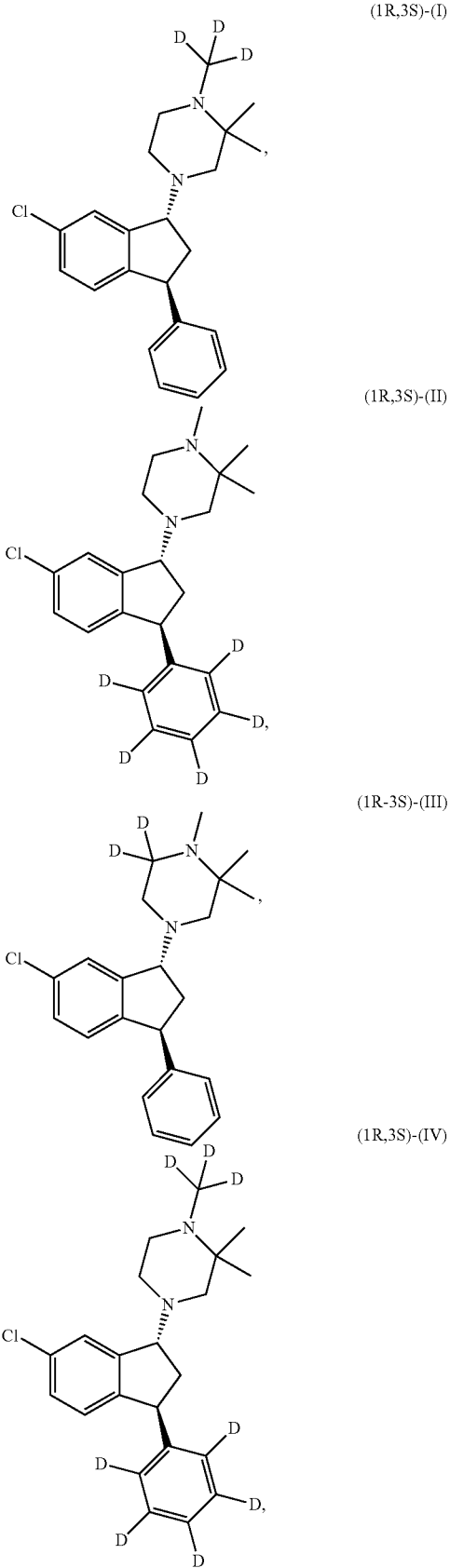

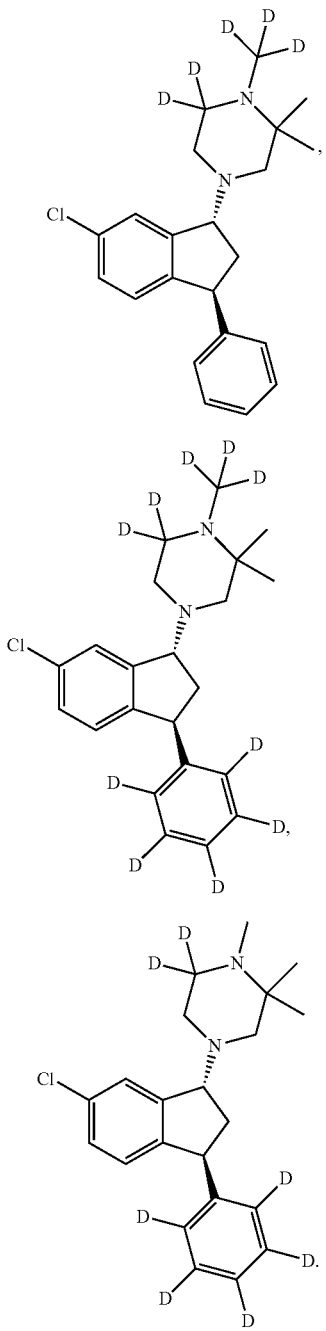

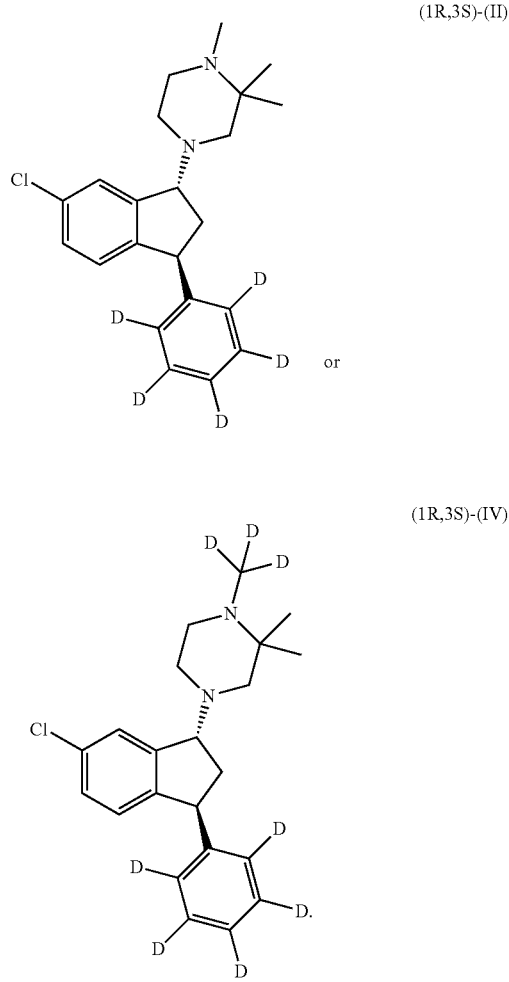

In some embodiments, $R^3$-$R^{10}$ comprise deuterium.
In some embodiments, $R^1$-$R^{10}$ comprise deuterium.
In some embodiments, the compound is In some embodiments, $R^1$ and $R^2$ comprise deuterium, $R^3$-$R^5$ comprise deuterium, or $R^6$-$R^{10}$ comprise deuterium.

In some embodiments, $R^1$ and $R^2$ comprise deuterium. In some embodiments, $R^1$ and $R^2$ comprise deuterium and $R^3$-$R^5$ comprise hydrogen.

In some embodiments, $R^3$-$R^5$ comprise deuterium. In some embodiments, $R^3$-$R^5$ comprise hydrogen.

In some embodiments, $R^6$-$R^{10}$ comprise deuterium. In some embodiments, $R^6$-$R^{10}$ comprise deuterium and $R^3$-$R^5$ comprise hydrogen.

In some embodiments, $R^1$-$R^5$ comprise deuterium.

In some embodiments, $R^1$, $R^2$, and $R^6$-$R^{10}$ comprise deuterium.

In some embodiments, the compound is

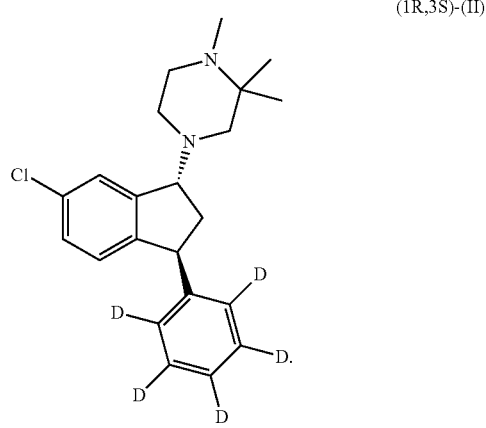

In some embodiments, the compound is

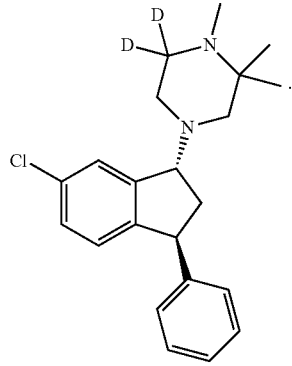
(1R,3S)-(III)

In some embodiments, the compound is

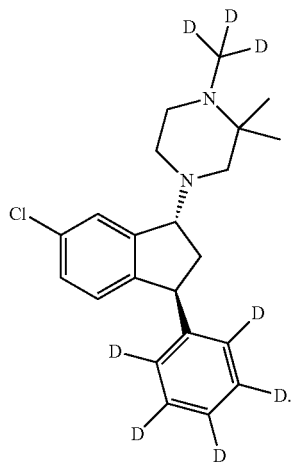
(1R,3S)-(IV)

In some embodiments, the compound is

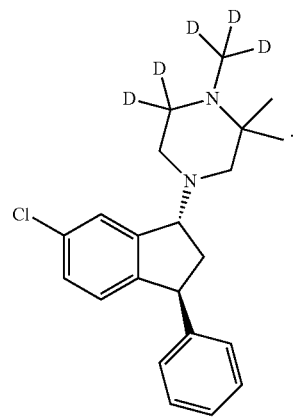
(1R,3S)-(V)

In some embodiments, the compound is

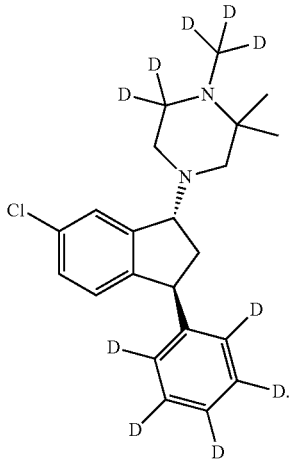
(1R,3S)-(VI)

In some embodiments, the compound is

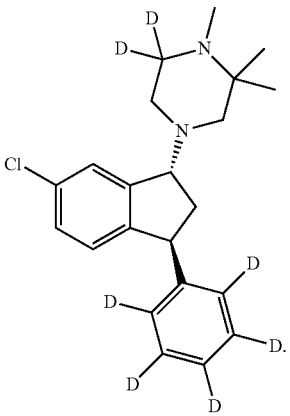
(1R,3S)-(VII)

In some embodiments, at least about 75% of the compound has a deuterium atom at each position designated as deuterium, and any atom not designated as deuterium is present at about its natural isotopic abundance.

In some embodiments, at least about 85% of the compound has a deuterium atom at each position designated as deuterium, and any atom not designated as deuterium is present at about its natural isotopic abundance.

In some embodiments, at least about 90% of the compound has a deuterium atom at each position designated as deuterium, and any atom not designated as deuterium is present at about its natural isotopic abundance.

In some embodiments, the compound is a salt selected from the group consisting of fumarate, maleate, succinate, and tartrate. In some embodiments, the compound is a fumarate salt. In some embodiments, the compound is a hydrogen fumarate salt. In some embodiments, the compound is a maleate salt. In some embodiments, the compound is a hydrogen maleate salt. In some embodiments, the compound is a succinate salt. In some embodiments, the compound is a hydrogen succinate salt. In some embodiments, the compound is a tartrate salt. In some embodiments, the compound is the hydrogen tartrate salt.

In some embodiments, the compound is the hydrogen tartrate salt of (1R,3S)-(IV).

In some embodiments, the psychosis or disease involving psychotic symptoms is schizophrenia, schizophreniform disorder, schizoaffective disorder, delusional disorder, brief psychotic disorder, shared psychotic disorder, bipolar disorder, or mania in bipolar disorder. In some embodiments, the psychosis or disease involving psychotic symptoms is schizophrenia.

In some embodiments, the methods further comprise administration of with one or more neuroleptic agents.

In some embodiments, the uses further comprise use of a one or more neuroleptic agents.

In some embodiments, the neuroleptic agent is selected from the group consisting of sertindole, olanzapine, risperidone, quetiapine, aripiprazole, haloperidol, clozapine, ziprasidone and osanetant.

In some embodiments, administration is oral, sublingual, or buccal. In some embodiments, administration is oral.

In some embodiments, the subject is a mammal. In some embodiments, the subject is a rodent, cat, dog, monkey, horse, swine, bovine, or human. In some embodiments, the subject is a rodent, cat, dog, monkey, bovine or human. In some embodiments, the subject is a mouse, rat, cat, dog, monkey, or human. In some embodiments, the subject is a mouse, rat, dog, monkey, or human. In some embodiments, the subject is a mouse, rat, dog, or human. In some embodiments, the subject is a mouse, rat or a human. In some embodiments, the subject is a dog or a human. In some embodiments, the subject is a human.

In some embodiments, designation of a position as "D" in a compound has a minimum deuterium incorporation of greater than about 40% at that position. In some embodiments, designation of a position as "D" in a compound has a minimum deuterium incorporation of greater than about 50% at that position. In some embodiments, designation of a position as "D" in a compound has a minimum deuterium incorporation of greater than about 60% at that position. In some embodiments, designation of a position as "D" in a compound has a minimum deuterium incorporation of greater than about 65% at that position. In some embodiments, designation of a position as "D" in a compound has a minimum deuterium incorporation of greater than about 70% at that position. In some embodiments, designation of a position as "D" in a compound has a minimum deuterium incorporation of greater than about 75% at that position. In some embodiments, designation of a position as "D" in a compound has a minimum deuterium incorporation of greater than about 80% at that position. In some embodiments, designation of a position as "D" in a compound has a minimum deuterium incorporation of greater than about 85% at that position. In some embodiments, designation of a position as "D" in a compound has a minimum deuterium incorporation of greater than about 90% at that position. In some embodiments, designation of a position as "D" in a compound has a minimum deuterium incorporation of greater than about 95% at that position. In some embodiments, designation of a position as "D" in a compound has a minimum deuterium incorporation of greater than about 97% at that position. In some embodiments, designation of a position as "D" in a compound has a minimum deuterium incorporation of greater than about 99% at that position.

Pharmaceutically Acceptable Salts

The present invention also comprises salts of the compounds, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutically acceptable inorganic or organic acid addition salts include the pharmaceutically acceptable salts listed in Berge, S. M. et al., *J. Pharm. Sci.* 1977, 66, 2, and Gould, P. L., *Int. J. Pharmaceutics* 1986, 33, 201-217; the contents of each are hereby incorporated by reference.

Furthermore, the compounds of this invention may exist in unsolvated as well as in solvated forms with pharmaceutically acceptable solvents such as water, ethanol and the like. In general, the solvated forms are considered comparable to the unsolvated forms for the purposes of this invention.

Headings and sub-headings are used herein for convenience only, and should not be construed as limiting the invention in any way.

The use of any and all examples, or exemplary language (including "for instance", "for example", "e.g.", and "as such") in the present specification is intended merely to better illuminate the invention, and does not pose a limitation on the scope of invention unless otherwise indicated.

The use of the terms "a" and "an" and "the" and similar referents in the context of describing the invention are to be construed to cover both the singular and the plural, unless otherwise indicated herein or clearly contradicted by context.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context.

Exemplary syntheses of the compounds of the invention can be readily achieved by methods described, for example, U.S. Pat. Nos. 5,807,855; 7,648,991; 7,767,683; 7,772,240; 8,076,342; U.S. Patent Publication Nos. 2008/0269248; 2010/0069676; 2011/0178094; 2011/0207744; WO 2005/016900; EP 0 638 073; and *J. Med. Chem.* 1995, 38, 4380-4392; each herein incorporated by reference in its entirety. Such methods, and similar methods can be performed using deuterated reagents and/or intermediates, and/or introducing deuterium atoms to a chemical structure according to protocols known in the art.

Further exemplary methods of synthesis include conversion of indanone A to intermediate C via treatment of 3-bromo-6-chloro-indan-1-one (A; for references on this material, see: Bøgesø EP 35363 A1 19810909 and Kehler, Juhl, Püschl, WO 2008025361; each herein incorporated by reference in its entirety) with a base such as triethylamine in a solvent such as tetrahydrofuran at ambient temperature (Scheme 1). Removal of the precipitated amine hydrobromide salt by filtration and concentration of the filtrate will afford 6-chloro-inden-1-one (B). This material can be reacted with phenyl-$d_5$-boronic acid in the presence of approximately 1 equivalent of a base such as triethylamine and a catalytic amount of a 1:1 mixture of [Rh(ndb)$_2$]BF$_4$ (bis(norbornadiene)rhodium(I) tetrafluoroborate) and racemic BINAP (2,2'-bis(diphenylphosphino)-1,1'-binaphthyl) in a suitable solvent (e.g. approximately 10:1 solvent mixture of 1,4-dioxane and water) under an atmosphere of argon at elevated temperature (e.g. about 100° C.). Work-up will afford racemic 6-chloro-3-phenyl-$d_5$-indan-1-one (C).

Scheme 1. Exemplary synthesis of intermediate C.

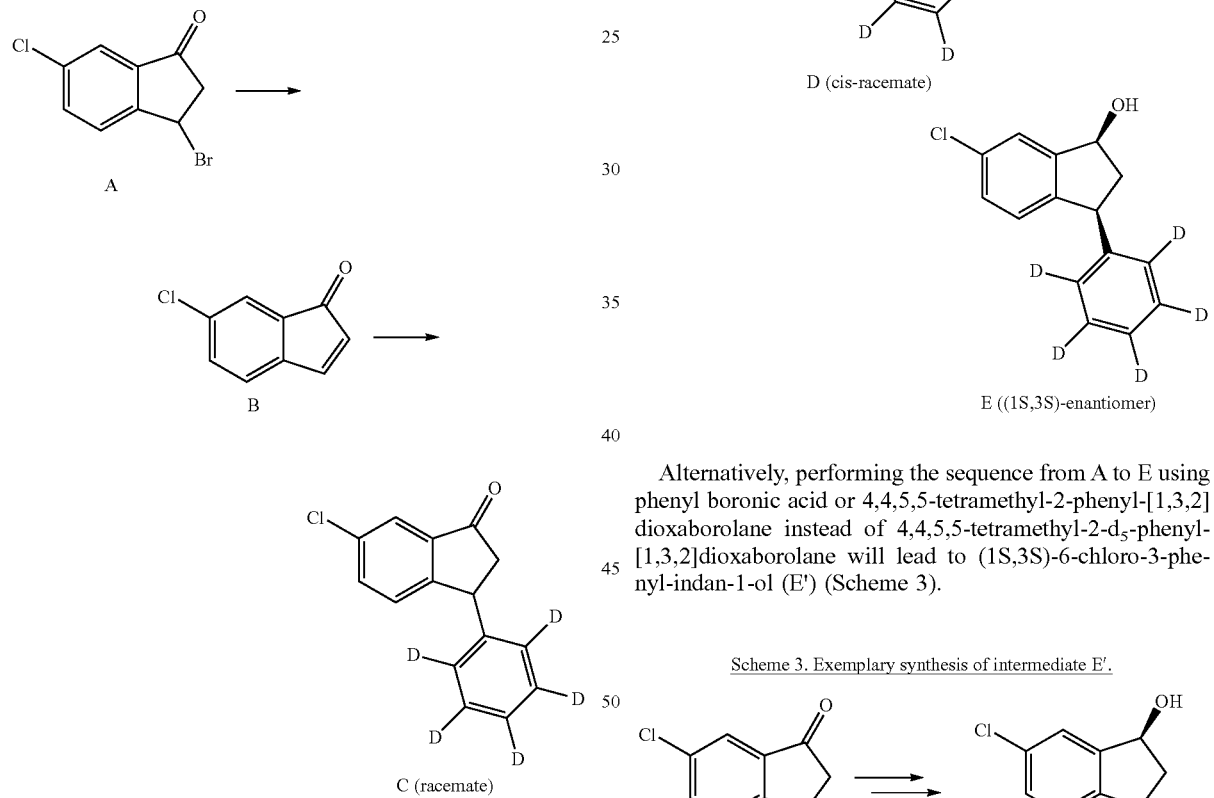

Treatment of 6-chloro-3-phenyl-$d_5$-indan-1-one (C) with a reductive base such as sodium borohydride (~2 equivalents) in a ~10:1 solvent mixture of tetrahydrofuran and water at low temperature (approximately −15° C.) will lead to reduction of the carbonyl group to the corresponding alcohol (Scheme 2). Work-up will afford racemic cis-6-chloro-3-phenyl-indan-1-ol (D). Treatment of this material with vinyl butyrate (approximately 5 equivalents) and Novozym 435® in a solvent such as di-iso-propyl ether at ambient temperature will afford (1S,3S)-6-chloro-3-phenyl-indan-1-ol (E) after work-up.

Scheme 2. Exemplary synthesis of intermediate E.

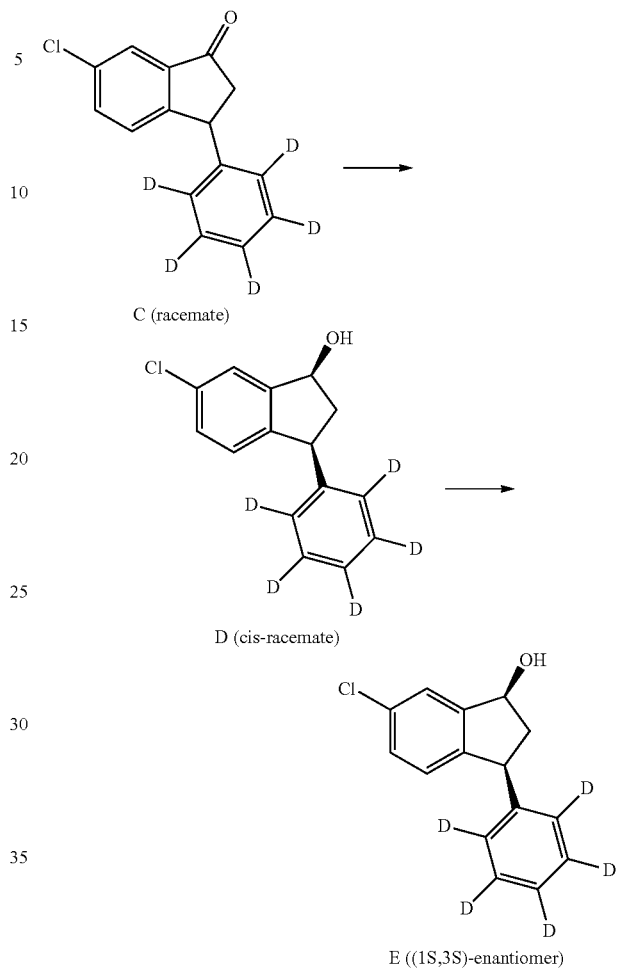

Alternatively, performing the sequence from A to E using phenyl boronic acid or 4,4,5,5-tetramethyl-2-phenyl-[1,3,2]dioxaborolane instead of 4,4,5,5-tetramethyl-2-$d_5$-phenyl-[1,3,2]dioxaborolane will lead to (1S,3S)-6-chloro-3-phenyl-indan-1-ol (E') (Scheme 3).

Scheme 3. Exemplary synthesis of intermediate E'.

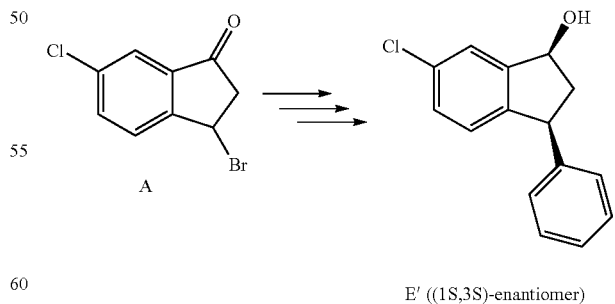

Further alternative synthetic methods to obtain E' are disclosed in the patent literature (Dahl, Wøhlk Nielsen, Suteu, Robin, Brøsen WO2006/086984 A1; Bang-Andersen, Bøgesø, Jensen, Svane, Dahl, Howells, Lyngsø, Mow WO2005/016901 A1; each herein incorporated by reference in its entirety). These procedures rely on benzyl cyanide as one of the substrates. Using benzyl cyanide-$d_7$ (commercially available from Aldrich, catalog #495840) or phenyl-$d_5$-acetonitrile (commercially available from Aldrich catalog #495859 or from CDN catalog # D-5340 or from Kanto catalog #49132-27) the same procedure may lead to E (Scheme 4). As alternatives to the commercial sources, benzyl cyanide-$d_7$ and phenyl-$d_5$-acetonitrile can be prepared sodium cyanide and benzyl-$d_7$ chloride (commercially available from Aldrich, catalog #217336) and benzyl-2,3,4,5,6-$d_5$ chloride (commercially available from Aldrich, catalog #485764), respectively.

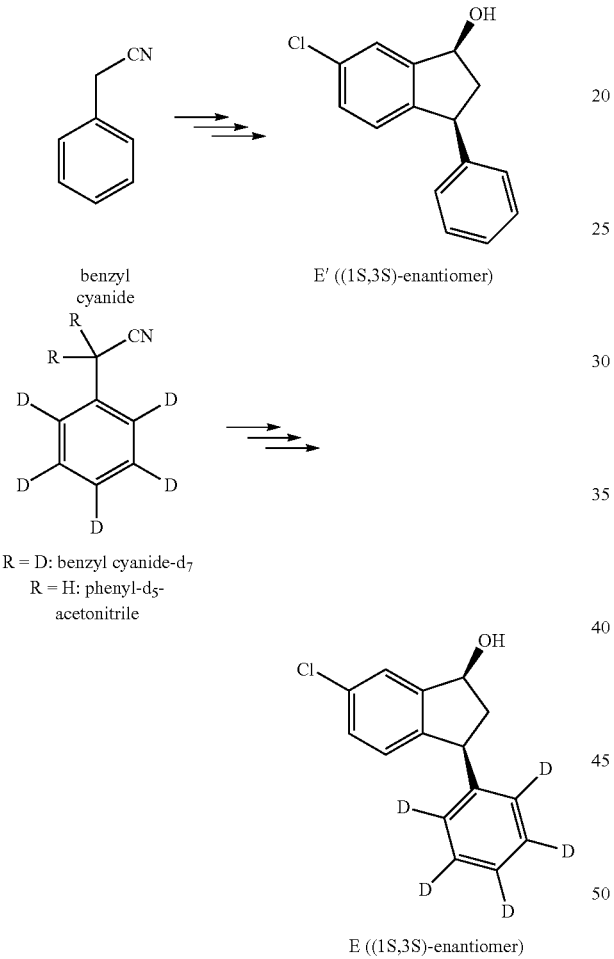

Scheme 4. Exemplary synthesis of intermediate E and E'.

Treatment of E with approximately 4 equivalents of di-iso-propylethylamine and approximately 2 equivalents methanesulphonic anhydride in tetrahydrofuran at approximately −18° C. followed by slow heating to approximately −5° C. and subsequent treatment with approximately 4 equivalents 2,2-dimethyl-piperazine will lead to the formation of 1-((1R,3S)-6-chloro-3-phenyl-$d_5$-indan-1-yl)-3,3-dimethyl-piperazine (F) that can be purified after the reaction (Scheme 5). Alternatively, one can convert alcohol E to the corresponding chloride, predominantly with retention of configuration at C1 leading to (1S,3S)-1-chloro-3-$d_5$-phenyl-indan (E″); similarly E′ can be converted to (1S,3S)-1-chloro-3-phenyl-indan (E‴)). Chloride E″ can be reacted with 2,2-dimethyl-piperazine to afford F. The final step can be performed as described for the preparation of Compound (I).butanedioic acid salt by the use of iodomethane to give Compound (II) or $d_3$-iodomethane to give Compound (IV), respectively. Alternatively, as described below, the methyl group or $d_3$-methyl group can be installed by refluxing in HCHO/HCOOH or DCDO/DCOOD, respectively.

Scheme 5. Exemplary synthesis of intermediates F and Compounds (II) and (IV).

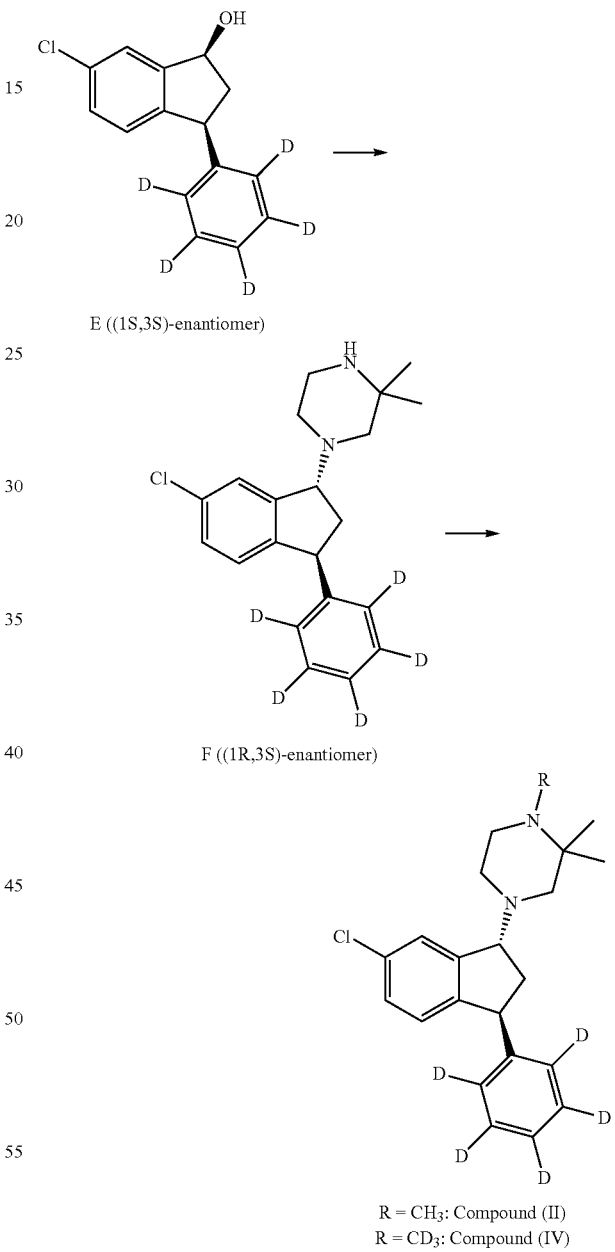

(2-Amino-2-methyl-propyl)-carbamic acid tert-butyl ester (G) can be prepared from 2-methyl-propane-1,2-diamine and di-tert-butyl dicarbonate (alternatively, G is claimed to be commercially available: Prime catalog # POI-1362-MB4; Rovathin catalog # NX45401). Reaction of G with a haloacetyl halide such as either chloroacetyl chloride or bromoacetyl bromide will give [2-(2-chloroacetylamino)-2-methyl-propyl]-carbamic acid tert-butyl ester or [2-(2-bromo-acetylamino)-2-methyl-propyl]-carbamic acid tert-butyl ester (H), respectively (Scheme 6). Treatment of either variant of H with acid followed by base will lead to the formation of 6,6-dimethyl-piperazine-2-one (I). This material can be reduced to 2,2-dimethyl-5,5-$d_2$-piperazine (J) by treatment with lithium aluminium deuteride.

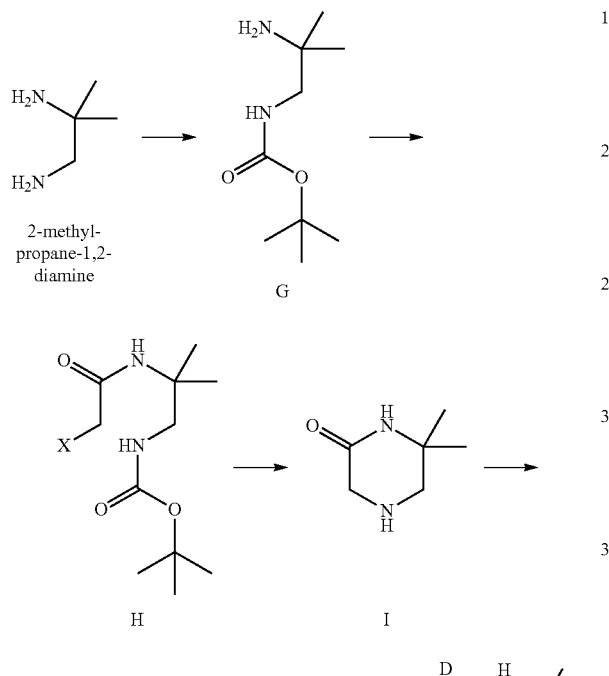

Scheme 6. Exemplary synthesis of intermediate J.

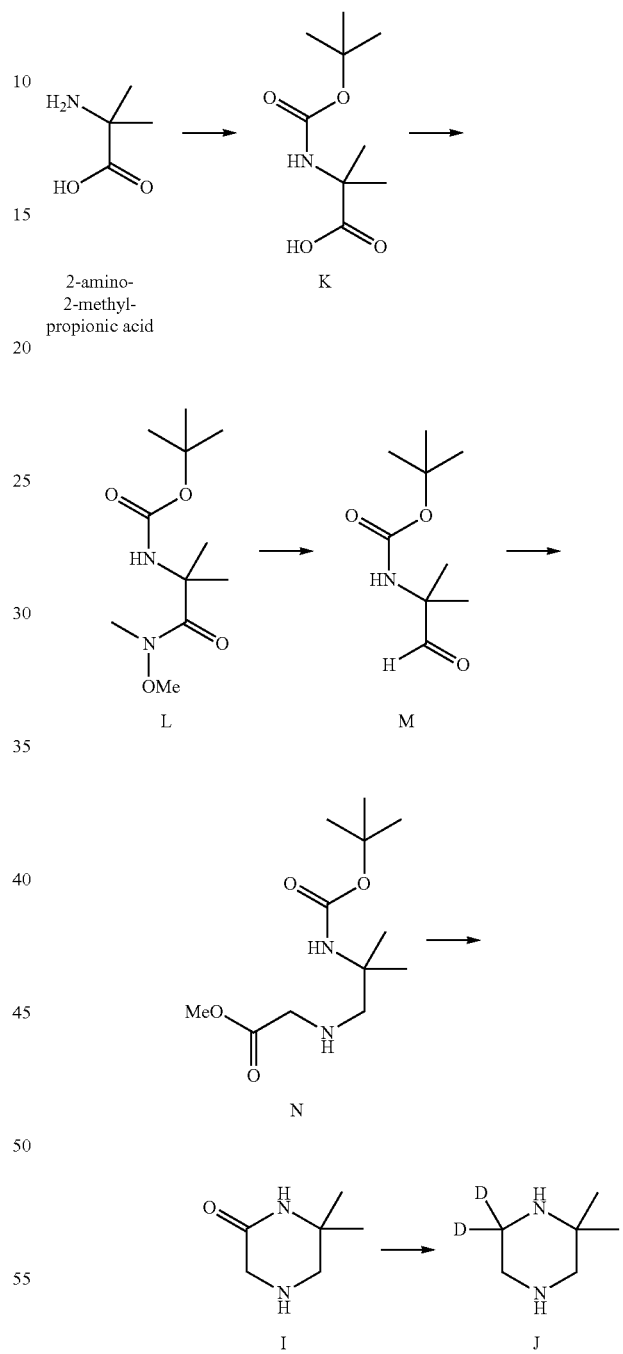

Scheme 7. Alternative exemplary synthesis of intermediate J.

Alternatively, J can be prepared from 2-amino-2-methyl-propionic acid. Reaction of 2-amino-2-methyl-propionic acid and di-tert-butyl dicarbonate will afford 2-tert-butoxycarbonylamino-2-methyl-propionic acid (K) (Scheme 7). The acid functionality can be converted to the corresponding Weinreb amide by reaction with O,N-dimethyl-hydroxylamine in the presence of a suitable coupling reagent such as 2-(1H-7-azabenzotriazol-1-yl)-1,1,3,3-tetramethyl uronium hexafluorophosphate methanaminium (HATU) or 1-ethyl-3-(3-dimethylaminopropyl) carbodiimide (EDC) to afford [1-(methoxy-methyl-carbamoyl)-1-methyl-ethyl]-carbamic acid tert-butyl ester (L). Selective reduction of the Weinreb amide leads to (1,1-dimethyl-2-oxo-ethyl)-carbamic acid tert-butyl ester (M). Reductive amination involving aldehyde M and amino-acetic acid methyl ester can be used to prepare (2-tert-butoxycarbonylamino-2-methyl-propylamino)-acetic acid methyl ester (N). Treatment of carbamate-ester N with a suitable acid, such as trifluoroacetic acid, will lead to the formation of piperazinone I that upon treatment with lithium aluminium deuteride gives piperazine J.

Using J instead of 2,2-dimethyl-piperazine as described for the conversion of E to Compounds (II) and (IV) will lead to Compounds (VI) and Compound (VII), respectively. Similarly, using E' and J instead of 2,2-dimethyl-piperazine and E will lead to Compound (III) and Compound (V).

In another aspect, the invention provides a process for the preparation of compound

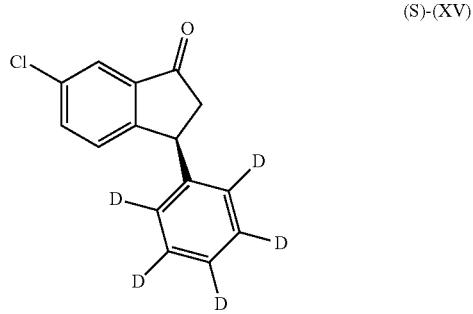 [SMILES: [2H]c1c([2H])c([2H])c([C@@H]2CC(=O)c3cc(Cl)ccc32)c([2H])c1[2H]]

(S)-(XV)

comprising treating compound (XIV) with [(S)-BINAP]Rh(I)BF$_4$.

In another aspect, the invention provides a process of the preparation of compound (1R,3S)-(IV) tartrate comprising treatment of racemic trans-1-(6-chloro-3-phenyl(d$_5$)-indan-1-yl)-1(d$_3$), 2,2-trimethyl-piperazine with L-(+)-tartaric acid.

In some embodiments, racemic trans-1-(6-chloro-3-phenyl(d$_5$)-indan-1-yl)-1 (d$_3$), 2, 2-trimethyl-piperazine is generated from the corresponding succinate salt thereof.

In some embodiments, racemic trans-1-(6-chloro-3-phenyl(d$_5$)-indan-1-yl)-1 (d$_3$), 2, 2-trimethyl-piperazine succinate is generated from the maleate salt of racemic trans-1-(6-chloro-3-phenyl(d$_5$)-indan-1-yl)-3,3-dimethyl-piperazine.

In some embodiments, acetophenone-d$_5$ is converted to an enol ether. In some embodiments, the enol ether is a silyl enol ether. In some embodiments, the enol ether of acetophenone-d$_5$ is converted to the corresponding vinyl boronate. In some embodiments, the enol ether of acetophenone-d$_5$ is treated with bis(pinacolato)diboron. In some embodiments, the vinyl boronate is treated with 2-halo-5-chlorobenzaldehyde.

In some embodiments, the compounds exist as racemates. In some embodiments, the compounds exist in greater than about 70% enantiomeric excess. In some embodiments, the compounds exist in greater than about 75% enantiomeric excess. In some embodiments, the compounds exist in greater than about 80% enantiomeric excess. In some embodiments, the compounds exist in greater than about 85% enantiomeric excess. In some embodiments, the compounds exist in greater than about 90% enantiomeric excess. In some embodiments, the compounds exist in greater than about 92% enantiomeric excess. In some embodiments, the compounds exist in greater than about 95% enantiomeric excess. In some embodiments, the compounds exist in greater than about 97% enantiomeric excess. In some embodiments, the compounds exist in greater than about 99% enantiomeric excess.

Pharmaceutical Compositions

The present invention further provides pharmaceutical compositions comprising a therapeutically effective amount of the compounds of the present invention and a pharmaceutically acceptable carrier or diluent.

The compounds of the invention may be administered alone or in combination with pharmaceutically acceptable carriers, diluents or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 21$^{st}$ Edition (University of the Sciences in Philadelphia, ed., Lippincott Williams & Wilkins 2005). Further exemplary compositions of the compounds of the invention are described in, for example, U.S. Pat. Nos. 5,807,855; 7,648,991; 7,767,683; 7,772,240; 8,076,342; U.S. Patent Publication Nos. 2008/0269248; 2010/0069676; 2011/0178094; 2011/0207744; WO 2005/016900; EP 0 638 073; and J. Med. Chem. 1995, 38, 4380-4392; each herein incorporated by reference in its entirety.

The pharmaceutical compositions may be specifically formulated for administration by any suitable route such as oral, nasal, topical (including buccal and sublingual), and parenteral (including subcutaneous, intramuscular, intrathecal, intravenous and intradermal) routes. It will be appreciated that the route will depend on the general condition and age of the subject to be treated, the nature of the condition to be treated and the active ingredient.

The daily dose of the compounds of the invention, calculated as the free base, is suitably from about 1.0 to about 160 mg/day, more suitably from about 1 to about 100 mg, e.g. preferably from about 2 to about 55, such as from about 2 to about 15 mg, e.g. from about 3 to about 10 mg. In some embodiments, the daily dose is from about 0.1 mg to about 500 mg. In some embodiments, the daily dose is from about 1 mg to about 500 mg. In some embodiments, the daily dose is from about 1 mg to about 400 mg. In some embodiments, the daily dose is from about 1 mg to about 300 mg. In some embodiments, the daily dose is from about 1 mg to about 200 mg. In some embodiments, the daily dose is from about 1 mg to about 160 mg. In some embodiments, the daily dose is from about 1 mg to about 100 mg. In some embodiments, the daily dose is from about 1 mg to about 60 mg. In some embodiments, the daily dose is from about 2 mg to about 30 mg. In some embodiments, the daily dose is from about 2 mg to about 15 mg. In some embodiments, the daily dose is from about 3 mg to about 10 mg. In some embodiments, the daily dose is about 60 mg. In some embodiments, the daily dose is about 50 mg. In some embodiments, the daily dose is about 40 mg. In some embodiments, the daily dose is about 30 mg. In some embodiments, the daily dose is about 20 mg. In some embodiments, the daily dose is about 10 mg. In some embodiments, the daily dose is about 5 mg. In some embodiments, the daily dose is about 3 mg. In some embodiments, the daily dose is about 2 mg. In some embodiments, the daily dose is about 1 mg.

For parenteral routes such as intravenous, intrathecal, intramuscular and similar administration, typical doses are in the order of half the dose employed for oral administration.

The compounds of this invention are generally utilized as the free substance or as a pharmaceutically acceptable salt thereof. Examples of suitable organic and inorganic acids are described herein.

In some embodiments, the composition comprises a cyclodextrin. In some embodiments, the composition comprises a cyclodextrin in water. In some embodiments, the cyclodextrin is hydroxypropyl-β-cyclodextrin. In some embodiments, the composition comprises hydroxypropyl-β-cyclodextrin in water.

Treatment of Disorders

The invention also relates to the medical use of compounds of the present invention, such as for the treatment of a disease in the central nervous system, including psychosis, in particular schizophrenia or other diseases involving psychotic symptoms, such as, e.g., Schizophrenia, Schizophreniform Disorder, Schizoaffective Disorder, Delusional Disorder, Brief Psychotic Disorder, Shared Psychotic Disorder as well other psychotic disorders or diseases that present with psychotic symptoms, e.g. bipolar disorder, such as mania in bipolar disorder. Compounds and/or compositions of the invention can further be used in treatment of disorders such as those described in, for example, U.S. Pat. Nos. 5,807,855; 7,648,991; 7,767,683; 7,772,240; 8,076,342; U.S. Patent Publication Nos. 2008/0269248; 2010/0069676; 2011/0178094; 2011/0207744; WO 2005/016900; EP 0 638 073; and *J. Med. Chem.* 1995, 38, 4380-4392; each herein incorporated by reference in its entirety. The invention also relates to the medical use of compounds of the present invention as combination therapy in conjunction with other therapeutic agents such as those described in, for example, U.S. Pat. Nos. 5,807,855; 7,648,991; 7,767,683; 7,772,240; 8,076,342; U.S. Patent Publication Nos. 2008/0269248; 2010/0069676; 2011/0178094; 2011/0207744; WO 2005/016900; EP 0 638 073; and *J. Med. Chem.* 1995, 38, 4380-4392; each herein incorporated by reference in its entirety.

It will recognized that one or more features of any embodiments disclosed herein may be combined and/or rearranged within the scope of the invention to produce further embodiments that are also within the scope of the invention.

Those skilled in the art will recognize, or be able to ascertain using no more than routine experimentation, many equivalents to the specific embodiments of the invention described herein. Such equivalents are intended to be within the scope of the present invention.

The invention is further described by the following non-limiting Examples.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Purification of compounds by chromatography refers to the application of silica gel chromatography using either manual flash chromatography or automated flash chromatography, typically performed using eluent gradients from heptanes to ethyl acetate or mixtures of ethyl acetate, triethylamine and methanol.

Description of LCMS Methods.

Compounds (I), (II), (III), (IV), (V), (VI) and (VII) were characterized by LCMS using the following methods (Table 1):

TABLE 1

Methods for LCMS Analysis

Methods WXV-AB5, WXV-AB10, and WXV-AB30

| | | |
|---|---|---|
| Equipment | Agilent 1100 LCMS system with ELS Detector | |
| | [method WuXiAB25 Agilent 1200 LCMS system with ELS Detector] | |
| | Pump | G1311A |
| | Degasser | G1379A |
| | Well-plate Autosampler | G1367A |
| | Column Oven | G1316A |
| | DAD | G1315B |
| | MSD | G1946C or G1956A [method WuXiAB25 6110] |
| | ELSD | Alltech ELSD 800 [method WuXiAB25 Aligent1200] |
| Column | YMC ODS-AQ [method WuXiAB25 Agilent TC-C18] | |
| | Particle size | 5 micrometer |
| | Pore size | 12 nm |
| | Dimension | 50 * 2.0 mm ID [method WuXiAB25 50 * 2.1 mm ID] |
| Injection volume | 2 microL | |
| Column temperature | 50° C. | |
| Flow | 0.8 mL/min | |
| Mobile phases | A | 0.1% TFA in water |
| | B | 0.05% TFA in acetonitrile |
| | Total run time | 4.5 min |
| | Gradient | linear |
| UV Detection | Wavelength | 254 nm |
| ELSD Detection | Temperature: | 50° C. |
| | Gas Pressure: | 3.2 bar |

| | Time | Gradient |
|---|---|---|
| WXV-AB05 | 0 min | 95% A 5% B |
| | 3.5 min | 0% A 100% B |
| | 3.55 min | 95% A 6% B |
| WXV-AB10 | 0 min | 90% A 10% B |
| | 3.4 min | 100% B |
| | 3.5 min | 100% B |
| | 3.51 min | 90% A 10% B |
| WXV-AB30 | 0 min | 70% A 30% B |
| | 3.2 min | 0% A 100% B |
| | 3.5 min | 0% A 100% B |
| | 3.55 min | 70% A 30% B |
| WuXiAB25 | 0 min | 75% A 25% B |
| | 3.4 min | 0% A 100% B |
| | 4 min | 0% A 100% B |
| | 4.01 min | 75% A 25% B |
| | 4.5 min | 75% A 25% B |

TABLE 1-continued

| Methods for LCMS Analysis | | |
|---|---|---|
| Method 131 | | |
| Equipment | Sciex API150EX equipped with APPI-source operating in positive ion mode | |
| | LC-MS were run on a Sciex API150EX equipped with APPI-source operating in posi-tive ion mode. The HPLC consisted of Shimadzu LC10-ADvp LC pumps, SPD-M20A PDA detector (operating at 254 nM) and SCL-10A system controller. Autosampler was Gilson | |
| | Autosampler | Gilson 215 |
| | Column Oven | Jones Chromatography 7990R |
| | ELSD | Sedere Sedex 85 |
| Column | Waters Symmetry C-18 | |
| | Particle size | 3.5 micrometer |
| | Dimension | 30 * 4.6 mm ID |
| Injection volume | 10 microL | |
| Column temperature | 60° C. | |
| Flow | 3.0 mL/min | |
| Mobile phases | A | 0.05% TFA in water |
| | B | 0.05% TFA in methanol |
| | Total run time | 2.8 min |
| | Gradient | non-linear |
| UV Detection | Wavelength | 254 nm |
| ELSD Detection | Temperature: | 50° C. |
| | Gas Pressure: | 4.4 bar |
| | Time | Gradient |
| | 0.01 min | 17% B in A |
| | 0.27 min | 28% B in A |
| | 0.53 min | 39% B in A |
| | 0.80 min | 50% B in A |
| | 1.07 min | 59% B in A |
| | 1.34 min | 68% B in A |
| | 1.60 min | 78% B in A |
| | 1.87 min | 86% B in A |
| | 2.14 min | 93% B in A |
| | 2.38 min | 100% B |
| | 2.40 min | 17% B in A |
| | 2.80 min | 17% B in A |

Description of Chiral HPLC Methods

The enantiomeric purity was assayed on a Hewlett Packard 1100 series system equipped with a diode array detector and using ChemStation for LC Rev. A.08.03[847]. The HPLC method parameters are described in the table below (Table 2). Compound (X) has a retention time around 13.6-13.7 min while its enantiomer, 4-((1S,3R)-6-chloro-3-phenyl-indan-1-yl)-1,2,2-trimethyl-piperazine, elutes at 8.5-8.6 min.

TABLE 2

| Methods for Chiral HPLC Analysis | |
|---|---|
| Sample Preparation | 1-3 mg/mL in hexane/2-propanol (80/20 v/v) |
| Column: | Chiralpak ADH 5 microm 250 × 4.6 mm |
| Column Temperature (° C.): | 30 |
| Injection (microL): | 5 |
| Detection: Wavelength, Bandwidth (nm): | 240, 8 |
| Total run-time | 30 min |
| Flow Rate (mL · min$^{-1}$): | 0.6 |
| Mobile Phase | hexane/2-propanol/diethylamine/propionic acid 90/10/0.2/2 |

Example 1

Preparation of 4-((1R,3S)-6-chloro-3-phenyl-indan-1-yl)-1-methyl-d$_3$-2,2-dimethyl-piperazine.butane-dioic acid (Compound (I).butanedioic acid salt)

Scheme 8. Synthesis of Compound (I).

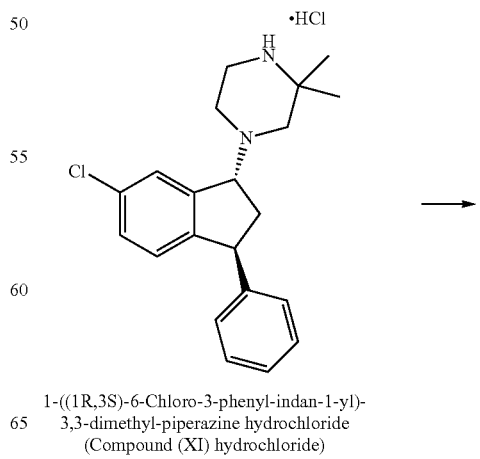

1-((1R,3S)-6-Chloro-3-phenyl-indan-1-yl)-3,3-dimethyl-piperazine hydrochloride
(Compound (XI) hydrochloride)

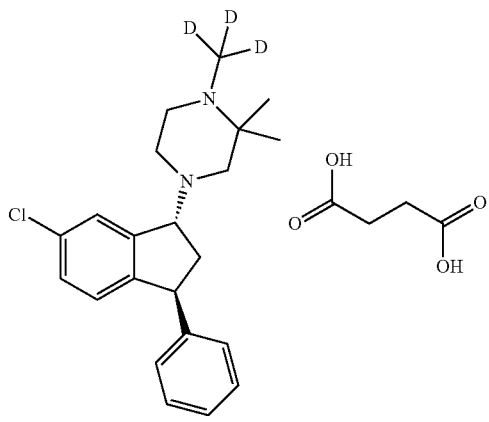

Compound (I) butanedioic acid salt 1-((1R,3S)-6-Chloro-3-phenyl-indan-1-yl)-3,3-dimethyl-piperazine hydrochloride (11.1 g) was dissolved in a mixture of toluene (74 mL) and water (74 mL). Preparation of 1-((1R,3S)-6-chloro-3-phenyl-indan-1-yl)-3,3-dimethyl-piperazine hydrochloride is disclosed in the patent literature (Dahl, Wøhlk Nielsen, Suteu, Robin, Brøsen WO2006/086984 A1; Bang-Andersen, Bøgesø, Jensen, Svane, Dahl, Howells, Lyngsø, Mow WO2005/016901 A1; each herein incorporated by reference in its entirety). 12.0 M of potassium hydroxide in water (5.38 mL), tetra-N-butylammonium bromide (1.42 g), and $d_3$-iodomethane (Aldrich catalog #176036; 2.4 mL) were added and the mixture was stirred at room temperature for 18 hours (Scheme 8). The mixture was filtered through a glass filter into a separatory funnel. The solid on the filter was washed with toluene (50 mL) into the separatory funnel. The aqueous layer was extracted with toluene (100 mL) and the combined organic layers were washed with concentrated aqueous ammonia (100 mL) and subsequently with water (100 mL) before it was dried over sodium sulfate, filtered, and concentrated in vacuum affording a slightly yellow oil. The oil was cooled to −78° C. under vacuum which solidified the oil. Upon warming to room temperature the oil became a semi-solid.

This material was dissolved in acetone (30 mL); in a separate flask butanedioic acid (3.46 g) was suspended in acetone (30 mL) and warmed to reflux (not all of the diacid went into solution). The acid suspension was added to the solution of the crude product and additional acetone (50 mL) was added to the butanedioic acid residue and then poured into solution. The mixture was stirred overnight. Partial precipitation had occurred overnight, and the mixture was concentrated in vacuum. The residue was re-dissolved in acetone (70 mL) and warmed to reflux and allowed to cool to room temperature and stirred for 2 hours.

The mixture was filtered affording 4-((1R,3S)-6-chloro-3-phenyl-indan-1-yl)-1-methyl-$d_3$-2,2-dimethyl-piperazine.butanedioic acid (Compound (I).butanedioic acid salt; 7.61 g). LC-MS (method 131): RT(UV) 1.57 min; UV/ELS purity 100%/100%; mass observed 358.0. Incorporation of three deuterium atoms >99%. The proton-decoupled $^{13}$C NMR spectrum showed a heptet around 36.4 ppm corresponding to the deuterated M2 metabolic site; this signal collapsed to a singlet in the proton- and deuterium-decoupled $^{13}$C NMR spectrum. All other signals were singlets in both spectra. Optical purity >95% ee.

Example 2

Alternative method of preparation of 4-((1R,3S)-6-chloro-3-phenyl-indan-1-yl)-1-methyl-$d_3$-2,2-dimethyl-piperazine.butanedioic acid (Compound (I).butanedioic acid salt)

The free base of 1-((1R,3S)-6-chloro-3-phenyl-indan-1-yl)-3,3-dimethyl-piperazine was prepared from the corresponding hydrochloride salt by partitioning 23.4 g of the salt between a mixture of water (100 mL), concentrated aqueous potassium hydroxide (40 mL), and toluene (250 mL). The organic layer was washed with a mixture of water (50 mL) and concentrated aqueous potassium hydroxide (10 mL). The combined aqueous layers were extracted with toluene (75 mL). The combined organic layers were dried over sodium sulfate, filtered, and concentrated in vacuum affording the free base of 1-((1R,3S)-6-chloro-3-phenyl-indan-1-yl)-3,3-dimethyl-piperazine (21.0 g) as a colorless oil. This material was dissolved in a mixture of toluene (150 mL) and water (150 mL), before 12.0 M aqueous potassium hydroxide (11.3 mL), tetra-N-butylammonium bromide (2.98 g), and $d_3$-iodomethane (4.9 mL) were added and mixture was stirred at room temperature for 18 hours.

Work-up and purification was performed as described above and afforded 4-((1R,3S)-6-chloro-3-phenyl-indan-1-yl)-1-methyl-$d_3$-2,2-dimethyl-piperazine.butanedioic acid (Compound (I).butanedioic acid salt; 14.34 g; 48.9%).

Example 3

Preparation of 4-((1R,3S)-6-chloro-3-phenyl-$d_5$-indan-1-yl)-1,2,2-trimethyl-piperazine (Compound (II)) and 4-((1R,3S)-6-chloro-3-phenyl-$d_5$-indan-1-yl)-1-methyl-$d_3$-2,2-dimethyl-piperazine (Compound (IV))

To a solution of compound A (57 g) in tetrahydrofuran (600 mL) was added triethylamine (30 mL) dropwise over 30 min. The reaction mixture was kept at room temperature for 3 hours. The precipitated solid was filtered and the filtrate was concentrated in vacuo. The residue was reprecipitated from diethyl ether to afford compound B (31 g) as a yellow solid. To a solution of compound phenyl-$d_5$-boronic acid (25 g) in 1,4-dioxane/water (900 mL/90 mL) was added [Rh(ndb)$_2$]BF$_4$ (1.3 g), racemic BINAP (2.1 g) and triethylamine (14 mL), then the reaction mixture was kept at room temperature for 2 hours under N$_2$. Then compound indenone (19 g) was added, and the resulting mixture was heated to 100° C. for 3 hours. The precipitated solid was filtered off. The filtrate was concentrated in vacuo. The residue was purified by chromatography to afford indanone C (10 g).

Scheme 9. Synthesis of Compound C.

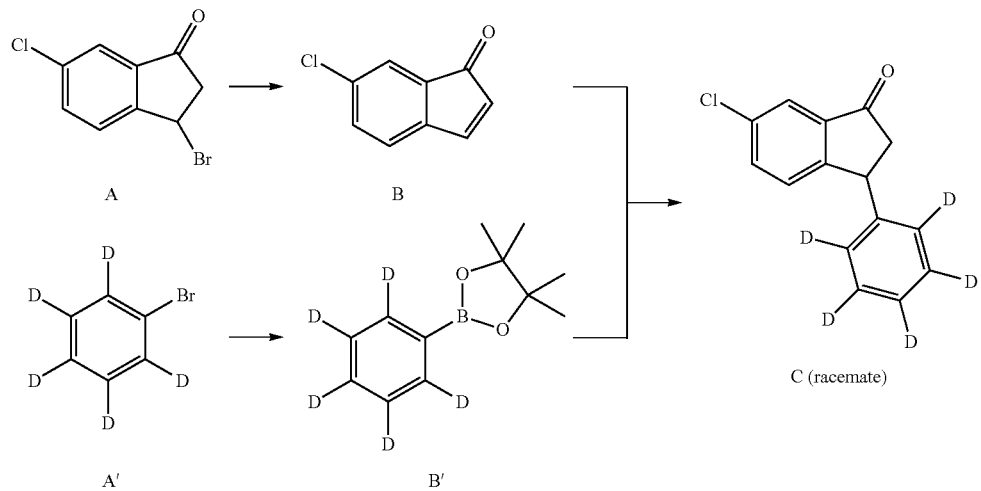

13.4 kg 3-Bromo-6-chloro-indan-1-one (A; for references on this material, see: Bøgesø EP 35363 A1 19810909 and Kehler, Juhl, Püschl, WO 2008025361; each herein incorporated by reference in its entirety) was dissolved in tetrahydrofuran (170.8 L), and the solution was cooled to 0-5° C. (Scheme 9). Triethylamine (9.1 L) was added over 0.5 h. The mixture was stirred at 0-5° C. for 5 hours before an additional portion of triethylamine (2.48 L) was added over 0.5 hour, and stirring was continued for 2 hours. The mixture was filtered, and the filtrate was concentrated to 30 L before n-heptane (102 L) was added. The volume was reduced to 60 L. More n-heptane (203 L) was added, and the mixture was stirred for 1 hour. Silica gel (17.2 kg) was added. The mixture was filtered, and the residual solid was washed with n-heptane (100 L). The combined filtrates were concentrated to 30 L and stirred at 0-5° C. for 1 hour. The mixture was centrifuged, and the residual solid was dried to afford 6-chloro-inden-1-one (compound B; 2.42 kg) sufficiently pure for the next step.

2-Methyl-tetrahydrofuran (85 L) and N,N-dimethyl acetamide (12.4 L) were added to a reactor followed by potassium acetate (10.9 kg) and bis(pinacolato)diboron (14.8 kg). The resulting mixture was stirred for 0.5 hour. Pd(dppf)Cl$_2$-DCM (0.91 kg) was added followed by bromobenzene-d$_5$ (9.0 kg) and 2-methyl-tetrahydrofuran (12.2 L). The mixture was heated to 80-85° C. for 3 hours, before the temperature was reduced to ambient temperature. The crude mixture was filtered via kieselguhr and silica gel. The filter-cake was washed with 2-methyl-tetrahydrofuran (31 L). The combined filtrates were concentrated to approximately 25 L while maintaining the temperature below 35° C. n-Heptane (52 L) and 7% aqueous NaHCO$_3$ (31 L) were added, and the mixture was stirred for 0.5 hour. The organic layer was stirred with 7% aqueous NaHCO$_3$ (31 L) for 0.5 hour. The combined aqueous layers were extracted with n-heptane (22 L) over 0.5 hour. The combined organic extracts were washed with 25% aqueous NaCl (50 L) over 0.5 hour. The organic layer was concentrated while maintaining the temperature below 35° C. to afford 4,4,5,5-tetramethyl-2-d$_5$-phenyl-[1,3,2]dioxaborolane (compound B'; 10.5 kg) sufficiently pure for the next step.

To a reactor was added sequentially 1,4-dioxane (85 L), 6-chloro-inden-1-one (compound B; 9.09 kg prepared in a similar manner to the one described above), 1,5-cyclooctadiene (0.2 L), bis(norbornadiene)rhodium(I) tetrafluoroborate (0.52 kg), triethylamine (5.5 L), 4,4,5,5-tetramethyl-2-d$_5$-phenyl-[1,3,2]dioxaborolane (compound B'; 6.5 kg), and 1,4-dioxane (26 L). The mixture was heated to 48-53° C. and stirred at that temperature for 5 hours. The reaction was quenched by the addition of 2M aqueous HCl (13 kg). Then n-heptane (110 L), methyl tert-butyl ether (32 L), and water (90 L) were added, and the resulting mixture was stirred for 0.3 hour. The organic layer was washed with water (90 L) over 0.3 hour. The combined aqueous layers were extracted with a mixture of methyl tert-butyl ether (30 L) and n-heptane (57 L) over 0.3 hour. The combined organic layers were filtered through silica gel (13 kg). The filter-cake was washed with a 2:1 mixture of n-heptane and methyl tert-butyl ether (19.5 kg). The filtrate was concentrated to approximately 25 L. n-Heptane (45 L) was added, and the volume was reduced to approximately 25 L. n-Heptane (45 L) was added, and the volume was reduced to approximately 35 L. The mixture was stirred at 0-5° C. for 3 hours. The mixture was centrifuged, and the residual solid was dried to afford racemic 6-chloro-3-d$_5$-phenyl-indan-1-one (compound C; 8.4 kg) sufficiently pure for the next step.

Tetrahydrofuran (90 L) was added to a reactor followed by water (10 L) and 6-chloro-3-d$_5$-phenyl-indan-1-one (compound C; 7.73 kg) (Scheme 10). The mixture was cooled to −35-−30° C. Sodium borohydride (1.5 kg) was added portion-wise while maintaining the temperature at −35-−30° C. The resulting mixture was stirred at −35-−30° C. for 5 hours before it was allowed to warm to ambient temperature. Excess sodium borohydride was quenched by the addition of 2M aqueous HCl (7.6 kg) while maintaining the temperature below 45° C. Water (17 L) and methyl tert-butyl ether (67 L) were added and the mixture was stirred for 0.3 hour. The aq layer was extracted with methyl tert-butyl ether (39 L) over 0.3 hour. The combined organic layers were washed with brine (36 kg) over 0.3 hour. The organic layer was filtered through silica gel (6.4 kg). The filter-cake was washed with methyl tert-butyl ether (20 L). The combined filtrates were concentrated to approximately 30 L while maintaining the temperature below 45° C. n-Heptane (55 L) was added and the resulting mixture was concentrated to approximately 30 L while maintaining the temperature below 45° C. The resulting mixture was stirred at 0-5° C. for 2 hours. The mixture was centrifuged, and the filter-cake was washed with n-heptane (12 L) before it was centrifuged again. The residual solid was dried to afford crude D. 4.87 kg of this material was dissolved in methyl tert-butyl ether (20 L) and dried over Na$_2$SO$_4$ (2 kg) over 0.25 hour. The mixture was filtered, and the filter-cake was washed with methyl tert-butyl ether (4.4 L). The combined filtrate was concentrated to approximately 20 L while maintaining the temperature below 45° C. n-Heptane (32 L) was added and the mixture was to approximately 25 L while maintaining the temperature below 45° C. n-Heptane (16 L) was added and the mixture was to approximately 20 L while maintaining the temperature below 45° C. The solid was filtered off and dried to afford racemic cis-6-chloro-3-d$_5$-phenyl-indan-1-ol (compound D; 4.99 kg) sufficiently pure for the next step.

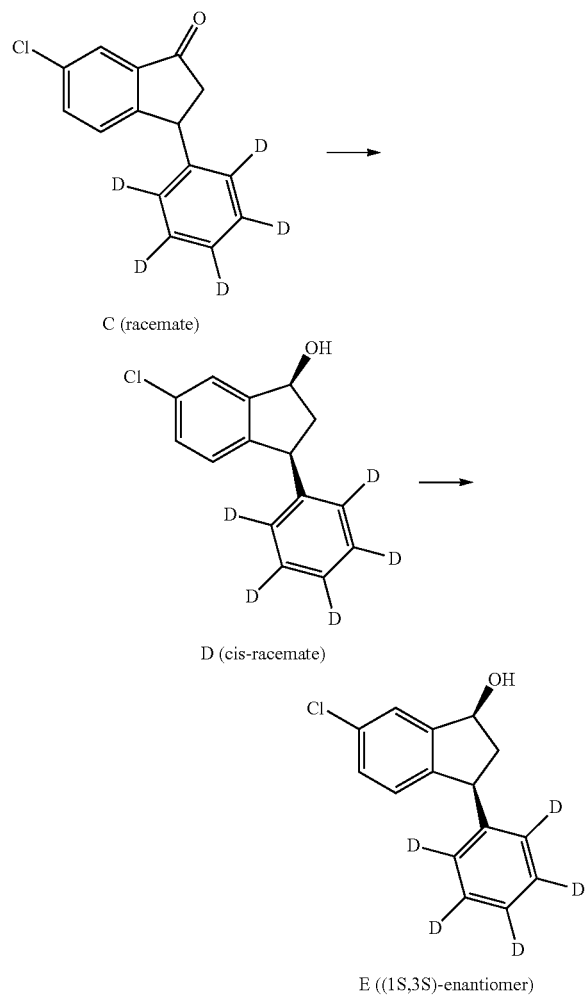

Scheme 10. Synthesis and resolution of Compound E.

C (racemate)

D (cis-racemate)

E ((1S,3S)-enantiomer)

To a solution of racemic cis-6-chloro-3-d$_5$-phenyl-indan-1-ol (compound D; 50 g) in 2-isopropoxypropane (200 mL) was added vinyl butyrate (120 mL) and Novozym-435 (15 g). The mixture was kept at ambient temperature for 2 days. The solid was filtered off. The filtrate was evaporated and purified by chromatography on silica gel to afford (1S,3S)-6-chloro-3-d$_5$-phenyl-indan-1-ol (compound E; 13 g) sufficiently pure for the next step.

To a solution of (1S,3S)-6-chloro-3-d$_5$-phenyl-indan-1-ol (compound E; 7 g) in THF (100 mL) was treated with SOCl$_2$ (6.6 g) at ambient temperature overnight. The mixture was poured into ice-cold water, and extracted with ethyl acetate. The organic layer was washed with brine. The organic layer was dried over Na$_2$SO$_4$, filtered, and concentrated in vacuo to afford the intermediate chloride (7.5 g). 3.5 g of this material was dissolved in 2-butanone (50 mL) and reacted with 2,2-dimethyl-piperazine (1.7 g) in the presence of K$_2$CO$_3$ (2.7 g) at reflux overnight. The solid was filtered off. The filtrate was concentrated in vacuo and the residue was purified by preparative HPLC on a Shimadzu FRC-10A instrument fitted with a Synergi C18 column (250 mm*50 mm, 10 microm) using water and acetonitrile (containing 0.1% TFA, v/v) as the eluent to afford 1-((1R,3S)-6-chloro-3-d$_5$-phenyl-indan-1-yl)-3,3-dimethyl-piperazine (compound F; 2.6 g) sufficiently pure for the next step.

To a solution of 1-((1R,3S)-6-chloro-3-d$_5$-phenyl-indan-1-yl)-3,3-dimethyl-piperazine (compound F; 2.2 g) in HCHO/HCOOH (3 mL/3 mL) was refluxed overnight. The volatiles were removed in vacuo. The residue was partitioned between ethyl acetate and 10% aq NaOH. The organic layer was dried over Na$_2$SO$_4$, filtered, and concentrated in vacuo. The residue was purified by chromatography on silica gel to afford 4-((1R,3S)-6-chloro-3-d$_5$-phenyl-indan-1-yl)-1,2,2-trimethyl-piperazine (Compound (II); 1.89 g). LC-MS (method WXV-AB05): RT(UV) 2.43 min; UV/ELS purity 95.1%/99.6%; mass observed 360.2. Incorporation of five deuterium atoms >95%. The proton-decoupled $^{13}$C NMR spectrum showed three triplets around 126.1, 127.2, and 128.2 ppm corresponding to the deuterated M3 metabolic sites; these signal collapsed to three singlets in the proton- and deuterium-decoupled $^{13}$C NMR spectrum. All other signals were singlets in both spectra. Optical purity >95% ee.

To a solution of 1-((1R,3S)-6-chloro-3-d$_5$-phenyl-indan-1-yl)-3,3-dimethyl-piperazine (compound F; 3.0 g) in DCDO/DCOOD (4 mL/4 mL) was refluxed overnight. The volatiles were removed in vacuo. The residue was partitioned between ethyl acetate and 10% aq NaOH. The organic layer was dried over Na$_2$SO$_4$, filtered, and concentrated in vacuo. The residue was purified by chromatography on silica gel to afford 4-((1R,3S)-6-chloro-3-d$_5$-phenyl-indan-1-yl)-1-d$_3$-methyl-2,2-dimethyl-piperazine (Compound (IV); 2.14 g). LC-MS (method WXV-AB10): RT(UV) 2.06 min; UV/ELS purity 98%/100%; mass observed 363.3. Incorporation of eight deuterium atoms >94%. The proton-decoupled $^{13}$C NMR spectrum showed a heptet around 36.4 ppm corresponding to the deuterated M2 metabolic site; this signal collapsed to a singlet in the proton- and deuterium-decoupled $^{13}$C NMR spectrum. The proton-decoupled $^{13}$C NMR spectrum further showed three triplets around 126.1, 127.2, and 128.2 ppm corresponding to the deuterated M3 metabolic sites; these signal collapsed to three singlets in the proton- and deuterium-decoupled $^{13}$C NMR spectrum. All other signals were singlets in both spectra. Optical purity >95% ee.

Example 4

Preparation of 4-((1R,3S)-6-chloro-3-phenyl-indan-1-yl)-1,2,2-trimethyl-piperazine-6,6-d$_2$ (Compound (III)), 4-((1R,3S)-6-chloro-3-phenyl-indan-1-yl)-1-methyl-d$_3$-2,2-dimethyl-piperazine-6,6-d$_2$ (Compound (V)), 4-((1R,3S)-6-chloro-3-phenyl-d$_5$-indan-1-yl)-1-methyl-d$_3$-2,2-dimethyl-piperazine-6,6-d$_2$ (Compound (VI)), and 4-((1R,3S)-6-chloro-3-phenyl-d$_5$-indan-1-yl)-1,2,2-trimethyl-piperazine-6,6-d$_2$ (Compound (VII)

2-Amino-2-methyl-propionic acid (50.0 g) was suspended in a mixture of methanol and triethylamine (9:1, 1.2 L) (Scheme 11). 1M aqueous NaOH (450 mL) was added with stirring until all solid was dissolved. Di-tert-butyl dicarbonate (Boc$_2$O; 214.0 g) was added, and the mixture was stirred at ambient temperature overnight. The organic volatiles were removed in vacuo. EtOAc (500 mL) was added. The organic layer was washed with brine and dried over Na$_2$SO$_4$, filtered, then concentrated to afford 2-tert-butoxycarbonylamino-2-methyl-propionic acid (compound K; 90 g) as a white solid which was used directly in next step directly.

Scheme 11. Synthesis of intermediate J.

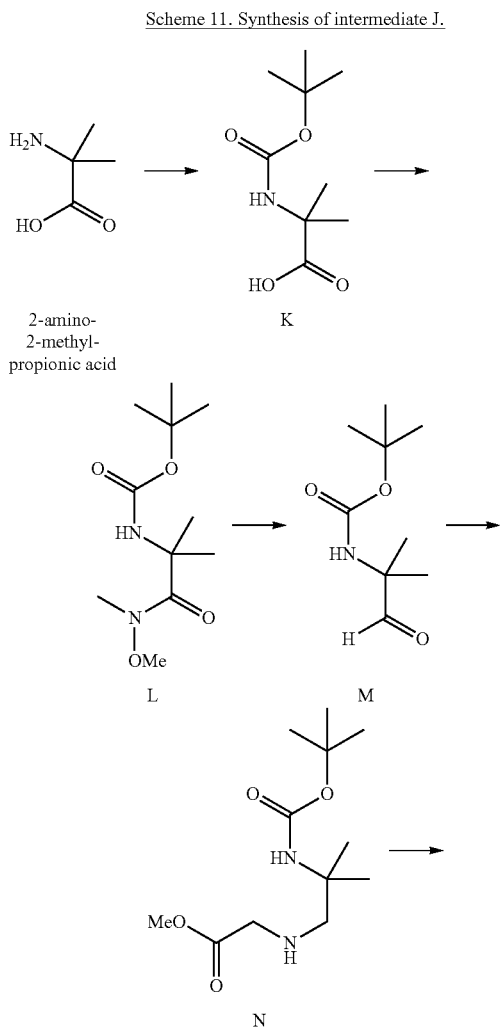

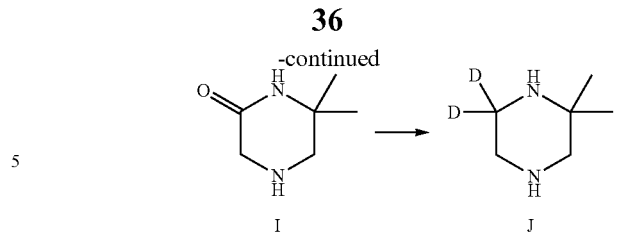

A mixture of afford 2-tert-butoxycarbonylamino-2-methyl-propionic acid (compound K; 60.0 g) and 1-ethyl-3 (3-dimethylaminopropyl) carbodiimide hydrochloride (EDC.HCl; 86.4 g) in dichloromethane (900 mL) was stirred at ambient temperature, then N,O-dimethyl hydroxylamine hydrochloride (35.3 g) and triethylamine (150 mL) were added. The resulting mixture was stirred at ambient temperature for 3 days. Water was added and most of volatiles were removed in vacuo. The residue was partitioned between DCM and aqueous NaHCO$_3$. The organic layer was washed with 3M aqueous HCl, subsequently with brine before it was dried over Na$_2$SO$_4$, filtered, and concentrated in vacuo. The residue was purified by silica gel chromatography to give [1-(methoxy-methyl-carbamoyl)-1-methyl-ethyl]-carbamic acid tert-butyl ester (compound L; 28.2 g) as a white solid sufficiently pure for the next step.

Lithium aluminum hydride (7.8 g) was added to a stirred solution of [1-(methoxy-methyl-carbamoyl)-1-methyl-ethyl]-carbamic acid tert-butyl ester (compound L; 42.0 g) in dry diethyl ether (1.5 L) at −40° C. Then stirred at that temperature for about 5 min. Excess LiAlH$_4$ was quenched with a solution of potassium hydrogen sulfate in water. The resulting mixture was partitioned between EtOAc and 3M aqueous HCl. The organic layer was washed with sat. aqueous NaHCO$_3$, dried over Na$_2$SO$_4$, filtered, and concentrated in vacuo to afford (1,1-dimethyl-2-oxo-ethyl)-carbamic acid tert-butyl ester (compound M; 29 g) sufficiently pure for the next step.

Amino-acetic acid methyl ester hydrochloride (80.6 g) and Et$_3$N (160 mL) were dissolved in DCM (1000 mL) and stirred for 15 min to liberate the amine from the salt. Then a solution of 1,1-dimethyl-2-oxo-ethyl)-carbamic acid tert-butyl ester (compound M; 29.0 g) in DCM (600 mL) was added. The resulting mixture was stirred for 0.5 hour at ambient temperature before NaBH(OAc)$_3$ (102 g) was added and the mixture was stirred at ambient temperature overnight. Sat. aqueous NaHCO$_3$ was added. The aqueous layer was extracted with DCM. The combined organic layers were dried over Na$_2$SO$_4$, filtered, and concentrated in vacuo. The residue was purified by silica gel chromatography to afford (2-tert-butoxycarbonylamino-2-methyl-propylamino)-acetic acid methyl ester (compound N; 26.5 g) as white solid which was used directly in the next step.

A mixture of (2-tert-butoxycarbonylamino-2-methyl-propylamino)-acetic acid methyl ester (compound N; 26.5 g) in DCM (800 mL) was stirred at ambient temperature, TFA (180 mL) was added drop-wise. The mixture was stirred at 30-40° C. for 5 h before it was concentrated in vacuo. The residue was partitioned between dissolved toluene and water. The organic layer was dried over Na$_2$SO$_4$, filtered, and concentrated in vacuo. The residual solid was dissolved in a mixture of ethanol (400 mL) and methanol (90 mL). K$_2$CO$_3$ (207 g) was added and the mixture was refluxed overnight. The mixture was cooled to room temperature. DCM (2500 mL) was added, and the mixture was stirred for 1 hour at ambient temperature. The solid was filtered off, and the filtrate was concentrated in vacuo to afford 6,6-dimethylpiperazin-2-one (Compound I; 5.85 g) as a white solid sufficiently pure for the next step.

A solution of 6,6-dimethyl-piperazin-2-one (Compound I; 3.6 g) in THF (20 mL) was stirred at 0° C. Lithium aluminum deuteride (LiAlD₄; 3.6 g) was added then the mixture was refluxed overnight. The mixture was cooled to ambient temperature and Na₂SO₄ was added. The mixture was stirred for 0.5 h before most of the volatiles were removed in vacuo. The residue was suspended in a saturated solution of HCl in EtOAc at ambient temperature for 0.5 hour. The solid was filtered off and dried to afford to give 2,2-d₂-6,6-dimethyl-piperazine as the bis-hydrochloride salt (Compound J.2HCl; 5.3 g) sufficiently pure for the next step.

To a solution of compound E' (5 g) in THF (50 mL) was added SOCl₂ (4.7 g), and the resulting mixture was stirred overnight at ambient temperature (Scheme 12). The mixture was poured into ice-water and extracted with EtOAc. The organic layer was washed with brine, dried over Na₂SO₄, filtered, and concentrated in vacuo to afford the corresponding chloride (5.3 g) which was used directly in the next step. 3.3 g of this material was dissolved in 2-butanone (50 mL) and reacted with 2,2-d₂-6,6-dimethyl-piperazine (Compound J; 3 g) in the presence of K₂CO₃ (8.28 g) at reflux overnight. The solid was filtered off. The filtrate was concentrated in vacuo. The residue was purified by preparative HPLC on a Shimadzu FRC-10A instrument fitted with a Synergy C18 column (250 mm*50 mm, 10 microm) using water and acetonitrile (containing 0.1% TFA, v/v) as the eluents to afford 1-((1R,3S)-6-chloro-3-phenyl-indan-1-yl)-3,3-d₂-5,5-dimethyl-piperazine (Compound 0; 1.7 g).

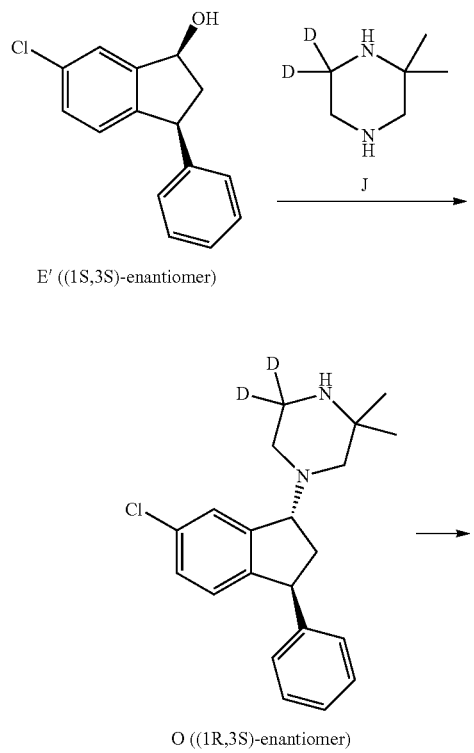

Scheme 12. Synthesis of Compound (III) and Compound (V).

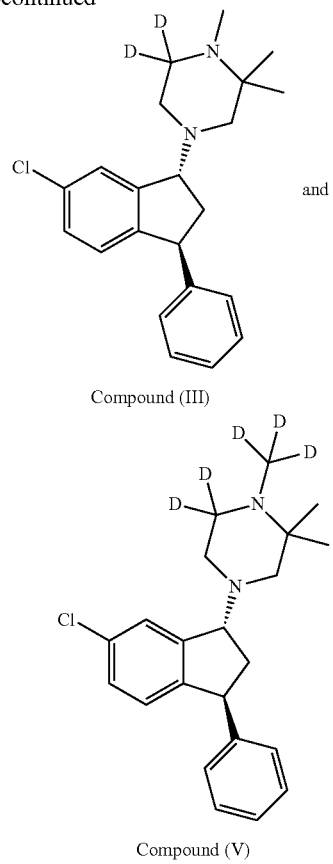

Compound (III)

and

Compound (V)

A solution of 1-((1R,3S)-6-chloro-3-phenyl-indan-1-yl)-3,3-d₂-5,5-dimethyl-piperazine (Compound 0; 0.5 g) in HCHO/HCOOH (1 mL/1 mL) was refluxed overnight. The volatiles were removed in vacuo. The residue was partitioned between EtOAc and 10% aqueous NaOH. The organic layer was dried over Na₂SO₄, filtered, and concentrated in vacuo. The residue was purified by chromatography on silica gel to afford 4-((1R,3S)-6-chloro-3-phenyl-indan-1-yl)-1,2,2-trimethyl-piperazine-6,6-d₂ (Compound (III); 0.33 g). LC-MS (method WXV-AB30): RT(UV) 1.42 min; UV/ELS purity 100%/100%; mass observed 357.2. Incorporation of two deuterium atoms >97%. The proton-decoupled ¹³C NMR spectrum showed a quintet around 49.5 ppm corresponding to the deuterated M1 metabolic site; this signal collapsed to a singlet in the proton- and deuterium-decoupled ¹³C NMR spectrum. The proton-decoupled ¹³C NMR spectrum further showed three triplets around 126.1, 127.2, and 128.2 ppm corresponding to the deuterated M3 metabolic sites; these signal collapsed to three singlets in the proton- and deuterium-decoupled ¹³C NMR spectrum. All other signals were singlets in both spectra. Optical purity >95% ee.

A solution of 1-((1R,3S)-6-chloro-3-phenyl-indan-1-yl)-3,3-d₂-5,5-dimethyl-piperazine (Compound 0; 0.7 g) in DCDO/DCOOD (1 mL/1 mL) was refluxed overnight. The volatiles were removed in vacuo. The residue was partitioned between EtOAc and 10% aqueous NaOH. The organic layer was dried over Na$_2$SO$_4$, filtered, and concentrated in vacuo. The residue was purified by chromatography on silica gel to afford 4-((1R,3S)-6-chloro-3-phenyl-indan-1-yl)-1-methyl-d$_3$-2,2-dimethyl-piperazine-6,6-d$_2$ (Compound (V); 0.49 g). LC-MS (method WXVAB25): RT(UV) 2.13 min; UV/ELS purity 100%/100%; mass observed 360.2. Incorporation of five deuterium atoms >95%. The proton-decoupled $^{13}$C NMR spectrum showed a heptet around 36.4 ppm corresponding to the deuterated M2 metabolic site; this signal collapsed to a singlet in the proton- and deuterium-decoupled $^{13}$C NMR spectrum. The proton-decoupled $^{13}$C NMR spectrum further showed a quintet around 49.5 ppm corresponding to the deuterated M1 metabolic site; this signal collapsed to a singlet in the proton- and deuterium-decoupled $^{13}$C NMR spectrum. All other signals were singlets in both spectra. Optical purity >95% ee.

To a solution of (1S,3S)-6-chloro-3-d$_5$-phenyl-indan-1-ol (compound E; 7 g) in THF (100 mL) was treated with SOCl$_2$ (6.6 g) at ambient temperature overnight (Scheme 13). The mixture was poured into ice-cold water, and extracted with ethyl acetate. The organic layer was washed with brine. The organic layer was dried over Na$_2$SO$_4$, filtered, and concentrated in vacuo to afford the intermediate chloride (7.5 g).

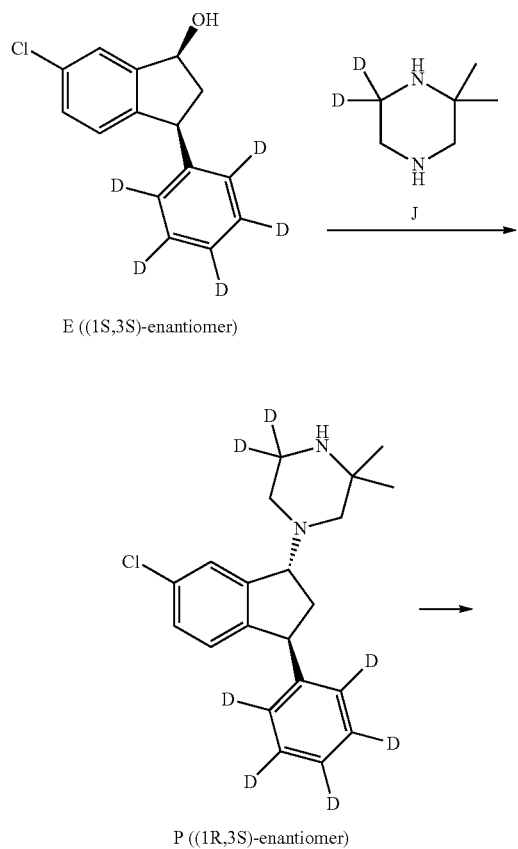

Scheme 13. Synthesis of Compound (VI) and Compound (VII).

E ((1S,3S)-enantiomer)

P ((1R,3S)-enantiomer)

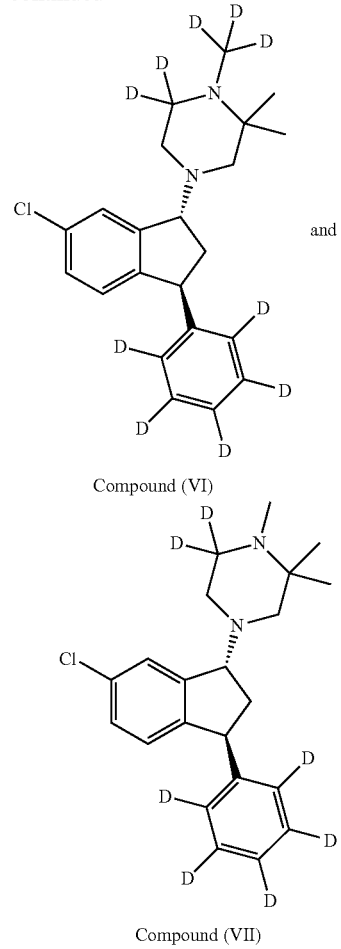

Compound (VI)

Compound (VII)

1.8 g of this material was dissolved in 2-butanone (30 mL) and reacted with 2,2-d$_2$-6,6-dimethyl-piperazine (Compound J; 1.4 g) in the presence of K$_2$CO$_3$ (5.5 g) at reflux overnight. The solid was filtered off. The filtrate was concentrated in vacuo. The residue was purified by preparative HPLC on a Shimadzu FRC-10A instrument fitted with a Synergy C18 column (250 mm*50 mm, 10 microm) using water and acetonitrile (containing 0.1% TFA, v/v) as the eluents to afford 1-((1R,3S)-6-Chloro-3-d$_5$-phenyl-indan-1-yl)-3,3-d$_2$-5,5-dimethyl-piperazine (Compound P; 1.7 g).

A solution of 1-((1R,3S)-6-chloro-3-d$_5$-phenyl-indan-1-yl)-3,3-d$_2$-5,5-dimethyl-piperazine (Compound P; 1 g) in DCDO/DCOOD (1.5 mL/1.5 mL) was refluxed overnight. The volatiles were removed in vacuo. The residue was partitioned between EtOAc and 10% aq NaOH. The organic layer was dried over Na$_2$SO$_4$, filtered, and concentrated in vacuo. The residue was purified by chromatography on silica gel to afford 4-((1R,3S)-6-chloro-3-d$_5$-phenyl-indan-1-yl)-1-d$_3$-methyl-2,2-dimethyl-piperazine-6,6-d$_2$ (Compound (VI); 0.55 g). LC-MS (method WuXiAB25): RT(UV) 2.13 min; UV/ELS purity 98.2%/100%; mass observed 365.2. Incorporation of ten deuterium atoms >91%. The proton-decoupled $^{13}$C NMR spectrum showed a heptet around 36.4 ppm corresponding to the deuterated M2 metabolic site; this signal collapsed to a singlet in the proton- and deuterium-decoupled $^{13}$C NMR spectrum. The proton-decoupled $^{13}$C NMR spectrum further showed a quintet around 49.5 ppm corresponding to the deuterated M1 metabolic site; this signal collapsed to a singlet in the proton- and deuterium-decoupled $^{13}$C NMR spectrum. The proton-decoupled $^{13}$C NMR spectrum further showed three triplets around 126.1, 127.2, and 128.2 ppm corresponding to the deuterated M3 metabolic sites; these signal collapsed to three singlets in the proton- and deuterium-decoupled $^{13}$C NMR spectrum. All other signals were singlets in both spectra. Optical purity >95% ee.

A solution of 1-((1R,3S)-6-chloro-3-d$_5$-phenyl-indan-1-yl)-3,3-d$_2$-5,5-dimethyl-piperazine (Compound P; 0.7 g) in HCHO/HCOOH (1 mL/1 mL) was refluxed overnight. The volatiles were removed in vacuo. The residue was partitioned between EtOAc and 10% aqueous NaOH. The organic layer was dried over Na$_2$SO$_4$, filtered, and concentrated in vacuo. The residue was purified by chromatography on silica gel to afford 4-((1R,3S)-6-chloro-3-d$_5$-phenyl-indan-1-yl)-1-methyl-2,2-dimethyl-piperazine-6,6-d$_2$ (Compound (VII); 0.47 g). LC-MS (method WXV-AB30): RT(UV) 1.33 min; UV/ELS purity 97.4%/100%; mass observed 362.3. Incorporation of seven deuterium atoms >93%=. The proton-decoupled $^{13}$C NMR spectrum showed a quintet around 49.5 ppm corresponding to the deuterated M1 metabolic site; this signal collapsed to a singlet in the proton- and deuterium-decoupled $^{13}$C NMR spectrum. The proton-decoupled $^{13}$C NMR spectrum further showed three triplets around 126.1, 127.2, and 128.2 ppm corresponding to the deuterated M3 metabolic sites; these signal collapsed to three singlets in the proton- and deuterium-decoupled $^{13}$C NMR spectrum. All other signals were singlets in both spectra. Optical purity >95% ee.

Example 5

Description of NMR Determination of the Position(s) Bearing Deuterium Rather than Hydrogen NMR spectra were recorded on a Bruker 600-Avance-III spectrometer equipped with a 5 mm TCI cryoprobe operating at 150.91 MHz for $^{13}$C. The solvent CDCl$_3$ was used as internal reference for the proton-decoupled experiments, while the proton- and inverse gated deuterium-decoupled spectra were recorded using gated lock. Difference(s) between the two spectra for the compounds of the invention determine(s) the position(s) of the deuterium atoms. When combining this information summarized in the table below (Table 3) with the electrospray mass spectrometry data that determined degree of deuteration, the structures of the compounds of the invention can be assigned unambiguously.

TABLE 3

Carbon NMR data for compounds.

| Cmpd. | M2 (methyl group @ ~36.4 ppm) | | M1 (methylene group @ ~49.5 ppm) | | M3 (phenyl group @ ~126.1 ppm, ~127.2 (2C), and ~128.2 (2C)) | |
|---|---|---|---|---|---|---|
| | $^{13}$C NMR proton-decoupled | $^{13}$C NMR proton- and deuterium-decoupled | $^{13}$C NMR proton-decoupled | $^{13}$C NMR proton- and deuterium-decoupled | $^{13}$C NMR proton-decoupled | $^{13}$C NMR proton- and deuterium-decoupled |
| (I) | heptet | singlet | singlet | singlet | singlets | singlets |
| (II) | singlet | singlet | singlet | singlet | 3 triplets | 3 singlets |
| (III) | singlet | singlet | quintet | singlet | 3 singlets | 3 singlets |
| (IV) | heptet | singlet | singlet | singlet | 3 triplets | 3 singlets |
| (V) | heptet | singlet | quintet | singlet | 3 singlets | 3 singlets |
| (VI) | heptet | singlet | quintet | singlet | 3 triplets | 3 singlets |
| (VII) | singlet | singlet | quintet | singlet | 3 triplets | 3 singlets |

Only NMR signals that 'change' as a consequence of the presence of D rather than H in the compounds of the invention are included in the table.

Figure 3A:
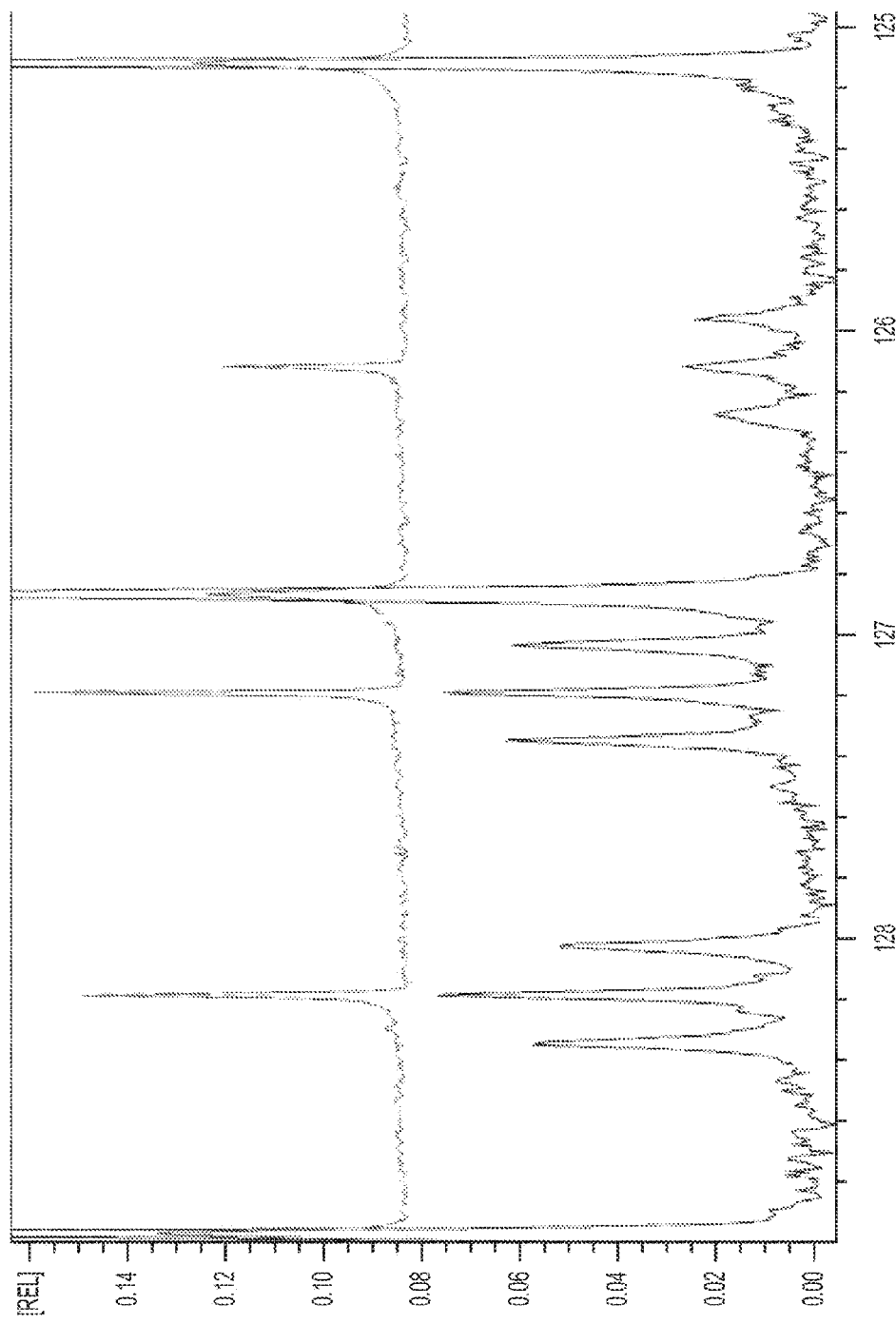
FIGS. 3A-3B show NMR spectra of Compound (II) and Compound (V). Selected regions of the proton-decoupled and proton- and deuterium-decoupled $^{13}$C NMR spectra of Compound (II) [FIG. 3A] and Compound (V) [FIG. 3B] are shown.
Figure 3B:
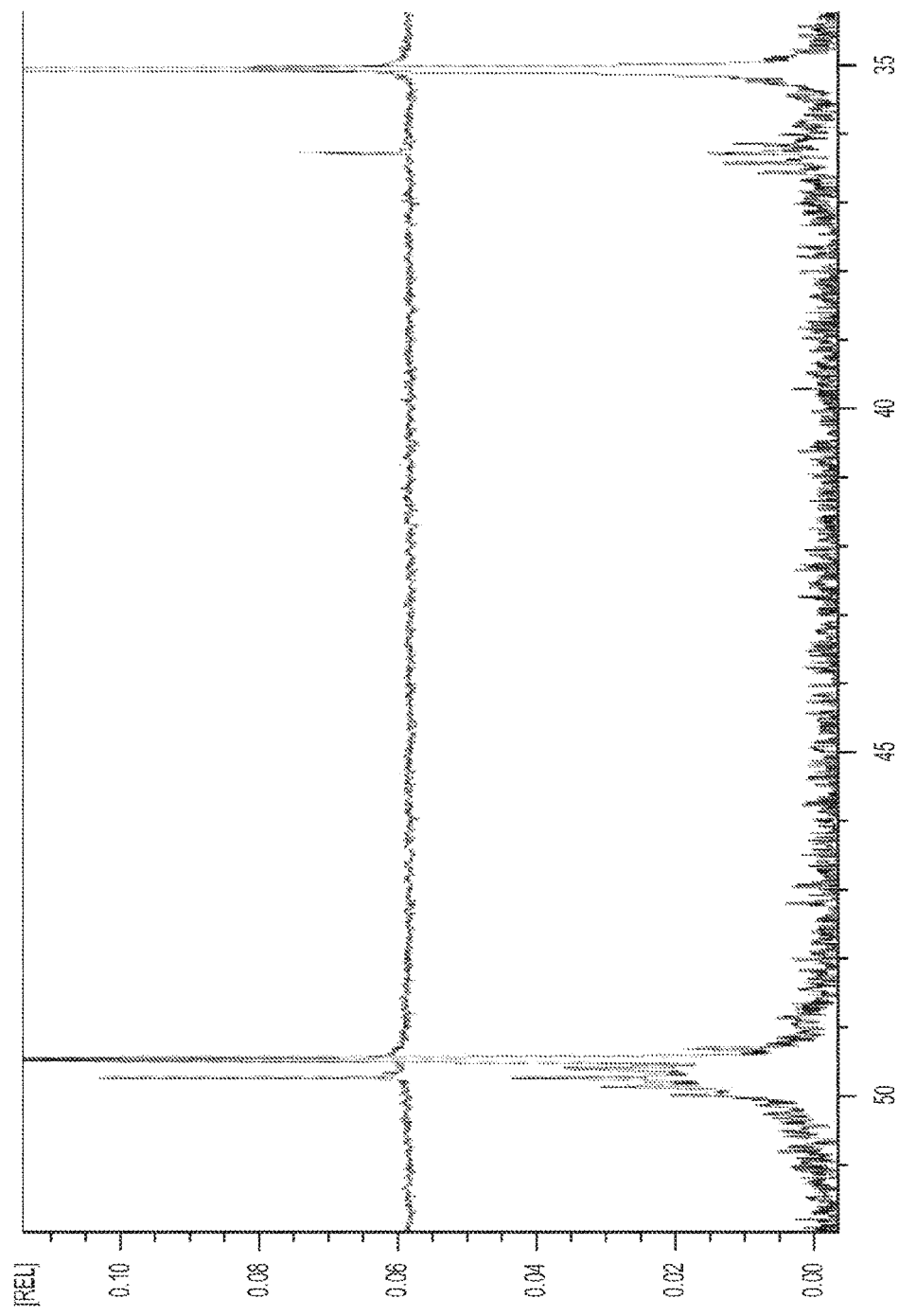

Relevant regions of the $^{13}$C proton-decoupled (lower spectrum) and $^{13}$C proton- and deuterium-decoupled (upper spectrum) NMR spectra of Compound (II) and Compound (V) are shown in FIG. 3 as representative examples. Selected regions of the proton-decoupled and proton- and deuterium-decoupled $^{13}$C NMR spectra of Compound (II) [FIG. 3A] and Compound (V) [FIG. 3B].

Example 6

Description of the Electrospray Mass Spectrometry to Determine Degree of Deuteration Instrumentation: Mass spectra of acidic, aqueous solutions of the compounds were obtained on a Hewlett Packard quadrupole mass spectrometer model 1100 LC-MSD. Liquid chromatography was performed on an Agilent 1100 HPLC-system coupled to the mass spectrometer.

Experimental: Solutions of the samples were made by dissolving approx. 2 mg substance in 2 mL methanol+18 mL 10 mM ammonium formate pH 3.0. Subsequently the solutions were diluted 100-fold prior to analysis. In order to get a "clean" peak, the samples were chromatographed using a Waters X-bridge C18, 3.5 microm (150×2.1 mm) column, and 0.1% trifluoroacetic acid/acetonitrile 50/50 as mobile phase. This procedure gave one peak of the compound of interest eluting at ca. 3.6 min, containing both the deuterated compounds of the invension as well as small quantities of deuterium-deficient species. The mass spectra obtained from these peaks were used to evaluate the speciation of the target molecules. The results were analyzed in percent of the total amount of substance, adding up to 100%. The actual potency of the compounds were not analyzed, merely the relative content of the deuterium deficient species.

Figure 4:
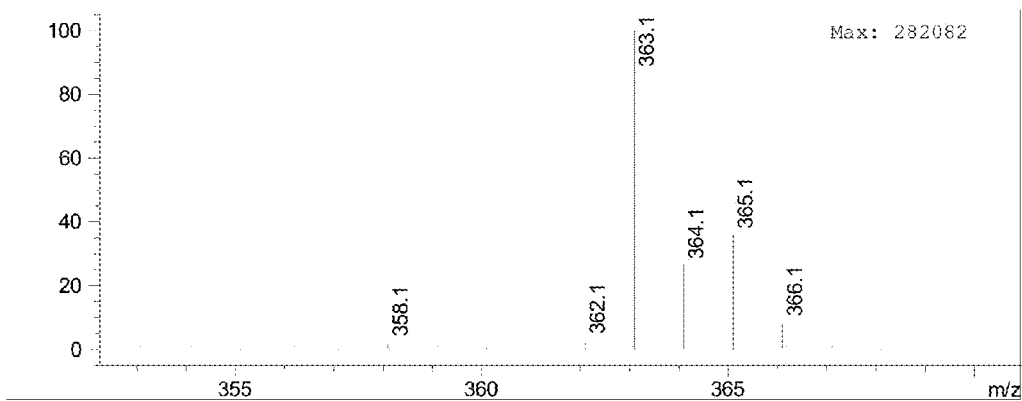
FIG. 4 shows the mass spectrum of Compound (IV).

As a representative example, the mass spectrum of Compound (IV) is shown in FIG. 4. The isotopic pattern of the protonated Compound (V) [M+H] with mass 363.1 u (362.1 u+1.0 u) and the isotope ions 363.1 u, 364.1 u, 365.1 u and 366.1 u was in the ratio 100:25.3:34.9:7.9; calculation for $C_{20}H_{22}N_2ClD_8$ gives the ratio 100:25.2:34.9:8.3. Furthermore, $D_7$-analogs and the $D_3$-analogs were observed at masses 362.1 u and 358.1 u, respectively. The signals at 364 u, 365 u and 366 u are primarily due to protonated molecules containing $^{13}C$ and/or $^{37}Cl$ isotopes instead of $^{12}C$ and $^{35}Cl$ (due to the natural distribution). This data shows that the incorporation of eight deuterium atoms was greater than 94%.

Example 7

Experimental Binding Assays

Description of Human $D_2$ Binding Assay

The assay was performed as a SPA-based competition-binding in a 50 mM Tris pH 7.4 assay buffer containing 120 mM NaCl, 5 mM KCl, 4 mM $MgCl_2$, 1.5 mM $CaCl_2$, 1 mM EDTA.

1.5 nM $^3H$-raclopride (Perkin Elmer, NET 975) was mixed with test compound before addition of 20 microg of a homogenised human $D_2$ receptor membrane-preparation and 0.25 mg SPA beads (WGA RPNQ 0001, Amersham) in a total volume of 90 microL. The assay plates were under agitation incubated for 60 minutes at room temperature and subsequently counted in a scintillation counter (TriLux, Wallac). The total binding, which comprised approximately 15% of added radioligand, was defined using assay buffer, whereas the non-specific binding was defined in the presence of 10 microM haloperidol. The non-specific binding constituted approximately 10% of the total binding.

Data points were expressed in percent of the specific binding of $^3H$-Raclopride and the $IC_{50}$ values (concentration causing 50 percent inhibition of $^3H$-raclopride specific binding) were determined by non-linear regression analysis using a sigmoidal variable slope curve fitting. The dissociation constant ($K_i$) was calculated from the Cheng Prusoff equation ($K_i=IC_{50}/(1+(L/K_D))$), where the concentration of free radioligand L is approximated to the concentration of added $^3H$-raclopride in the assay. The $K_D$ of $^3H$-raclopride was determined to 1.5 nM from two independent saturation assays each performed with triplicate determinations.

Description of Human $D_1$ Binding Assay

The assay was performed as a SPA-based competition-binding in a 50 mM Tris pH 7.4 assay buffer containing 120 mM NaCl, 5 mM KCl, 4 mM $MgCl_2$, 1.5 mM $CaCl_2$, 1 mM EDTA. Approximately 1 nM $^3H$-SCH23390 (Perkin Elmer, NET 930) was mixed with test compound before addition of 2.5 microg of a homogenized human $D_1$ receptor membrane-preparation and 0.25 mg SPA beads (WGA RPNQ 0001, Amersham) in a total volume of 60 microL.

The assay plates were under agitation incubated for 60 minutes at room temperature before the plates were centrifuged and subsequently counted in a scintillation counter (TriLux, Wallac). The total binding, which comprised approximately 15% of added radioligand, was defined using assay buffer whereas the non-specific binding was defined in the presence of 10 microM haloperidol.

Data points were expressed in percent of the specific binding and the $IC_{50}$ values (concentration causing 50 percent inhibition of specific binding) and were determined by non-linear regression analysis using a sigmoidal variable slope curve fitting. The dissociation constant ($K_i$) was calculated from the Cheng Prusoff equation ($K_i=IC_{50}/(1+(L/K_D))$), where the concentration of free radioligand L is approximated to the concentration of added radio-ligand in the assay.

Description of Human $5-HT2_A$ Binding

The experiment was carried out at Cerep Contract Laboratories (Cat. ref #471).

Compound (I) was also tested in an in vivo set up demonstrating central effects of the compound. By in vivo binding, the compound's in vivo affinity for $D_2$ receptors was assessed and occupancy of 60% of the target was observed. Occupancy of $D_2$ receptors is closely linked to antipsychotic effects in animal models and in patients.

Description of In Vivo Binding to $D_2$ Receptors in Rat Brain

In vivo binding was carried out according to Andersen et al (Eur J Pharmacol, (1987) 144:1-6; herein incorporated by reference in its entirety) with a few modifications (Kapur S. et al, J Pharm Exp Ther, 2003, 305, 625-631; herein incorporated by reference in its entirety). Briefly, 6 rats (male Wistar, 180-200 g) were treated with 20 mg/kg test compound subcutaneous 30 minutes before receiving 9.4 micro Ci [$^3H$]-raclopride intravenously via the tail vein.

15 minutes after the injection of the radio ligand the animals were killed by cervical dislocation, the brain quickly removed and striatum and cerebellum dissected out and homogenized in 5 mL (cerebellum in 20 mL) ice-cold buffer (50 mM $K_3PO_4$, pH 7.4). 1.0 mL of the homogenate was filtered through 0.1% PEI-soaked Whatman GF/C filters. This was completed within 60 seconds subsequent to the decapitation. Filters were washed 2 times with 5 mL ice-cold buffer and counted in a scintillation counter. A group of vehicle treated animals was used to determine [$^3H$]-raclopride total binding in striatum and non-specific binding in cerebellum. The homogenate was measured for protein content by the BCA protein determination assay (Smith P. K. et al (1985) Anal. Biochem., 150: 6-85; herein incorporated by reference in its entirety).

Example 8

Investigation of the metabolism of 4-((1R,3S)-6-chloro-3-phenyl-indan-1-yl)-1,2,2-trimethyl-piperazine (Compound (X)) and 4-((1R,3S)-6-chloro-3-phenyl-indan-1-yl)-1-methyl-$d_3$-2,2-dimethyl-piperazine (Compound (I))

Cryopreserved dog (male Beagle dog) hepatocytes (1 million cells/mL in suspension, 50 microL/well) were pre-incubated for 15 minutes in a 96 well plate at 37° C. water bath in DMEM high glucose buffered with 1M HEPES. The cell suspension was added with 50 microL test compounds (final concentration 0.1 or 1 microM of 4-((1R,3S)-6-chloro-3-phenyl-indan-1-yl)-1,2,2-trimethyl-piperazine (Compound (X)) or 4-((1R,3S)-6-chloro-3-phenyl-indan-1-yl)-1-methyl-$d_3$-2,2-dimethyl-piperazine (Compound (I)) and further incubated for 0, 15, 45, 75 and 120 minutes. The reaction was stopped by addition of 100 microL acetonitrile to the cell suspension, and the samples were then removed for LC-MS analysis of the desmethyl metabolite (Compound (XI)). Data were expressed as MS area relative to an internal standard.

Figure 5:
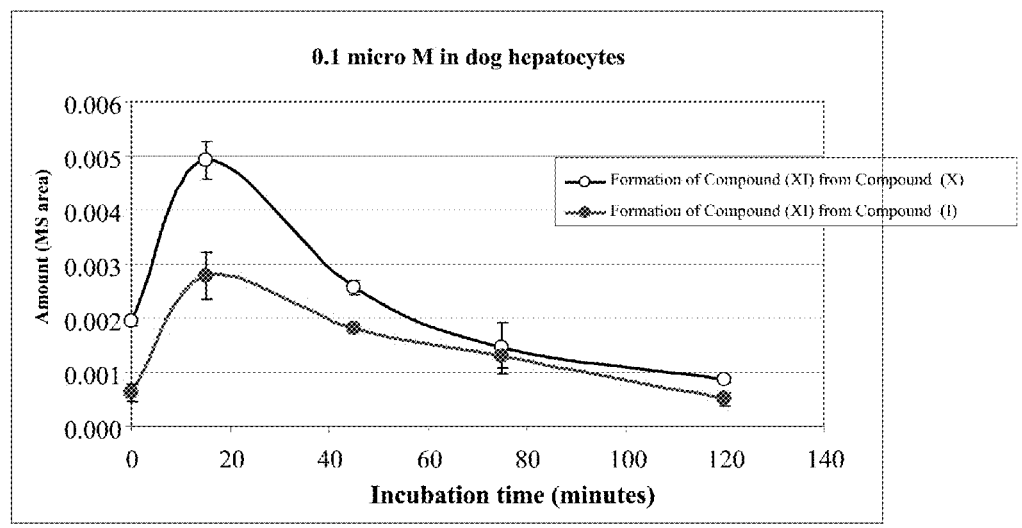
FIG. 5 shows formation of the metabolite Compound (XI) by metabolism of Compound (X) and Compound (I) (0.1 microM) in cryopreserved dog hepatocytes (n=2 the bars represent max and min results).
Figure 6:
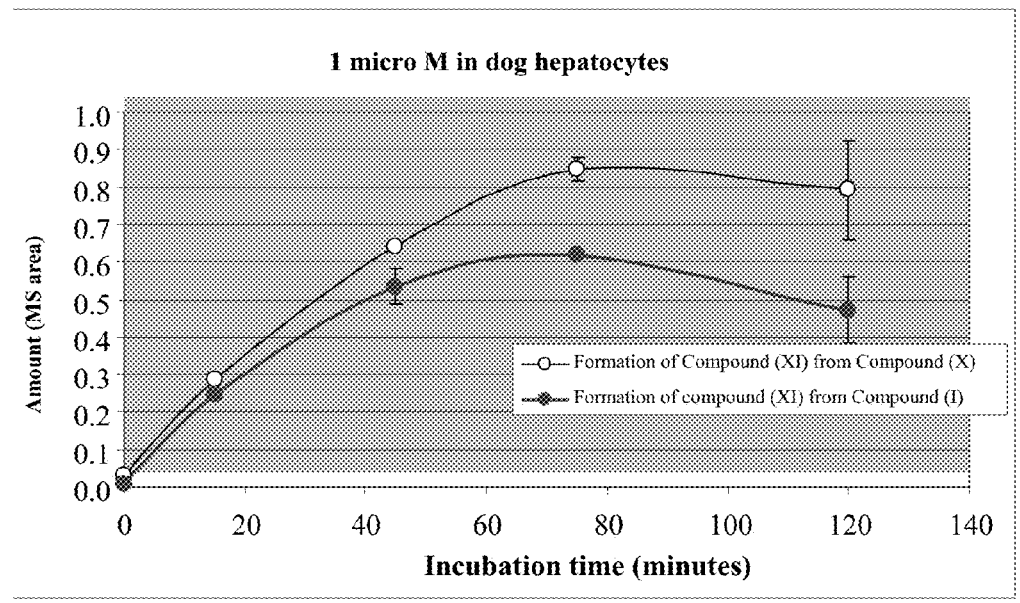
FIG. 6 shows formation of the metabolite Compound (XI) by metabolism of Compound (X) and Compound (I) (1 microM) in cryopreserved dog hepatocytes (n=2 the bars represent max and min results).

The results (FIG. 5 and FIG. 6) show that the amount of the desmethyl metabolite (Compound (XI)) produced in cryopreserved dog hepatocytes is lower from the deuterated form (Compound (I)) than from the parent compound (Compound (X)), both at a concentration of 0.1 micro M (FIG. 5) and at a concentration of 1 micro M (FIG. 6).

Example 9

Pharmacological Testing of Compounds 4-((1R,3S)-6-chloro-3-phenyl-indan-1-yl)-1-$d_3$-methyl-2,2-dimethyl-piperazine (Compound (I))

4-((1R,3S)-6-chloro-3-phenyl-indan-1-yl)-1-$d_3$-methyl-2,2-dimethyl-piperazine (Compound (I)) was tested in three in vitro assays for dopamine $D_1$, dopamine $D_2$ and serotonin 5-$HT_{2A}$ affinity.

The experiments were carried out as in the section Binding assays. The experimental results showed the following affinities for 4-((1R,3S)-6-chloro-3-phenyl-indan-1-yl)-1-methyl-$d_3$-2,2-dimethyl-piperazine:

$D_1$: Ki log mean=7.5 nM (pKi 0.88+/−0.15)
$D_2$: Ki log mean=34 nM (pKi 1.54+/−0.11)
5$HT_{2A}$: IC50=1.14 nM These binding affinities indicate that Compound (I) has biological activity likely to exert antipsychotic effect.

Pharmacological Testing of Compound (II) and Compound (IV)

The experiments were carried out as described in the section "Binding assays". The experimental results for the two compounds are provided below.

Compounds (II) and Compound (IV) were tested in two in vitro assays for dopamine $D_1$ and dopamine $D_2$ affinity.

Compound (IV):
$D_1$: Ki log mean=26.1 nM (pKi 1.42+/−0.03)
$D_2$: Ki log mean=26.7 nM (pKi 1.43+/−0.04)

Compound (II):
$D_1$: Ki log mean=23.2 nM (pKi 1.37+/−0.03)
$D_2$: Ki log mean=26.5 nM (pKi 1.42+/−0.03)

These binding affinities indicate that Compound (II) and (IV) have biological activity likely to exert antipsychotic effect.

Compound (II) and (IV) were also tested in an in vivo set up demonstrating central effects of the compound. By in vivo binding, the compound's in vivo affinity for $D_2$ receptors was assessed and occupancy of 70% (Compound (IV)) and 75% (Compound (II)) of the target was observed. Occupancy of $D_2$ receptors is closely linked to antipsychotic effects in animal models and in patients.

Compounds (I)-(VII) and (X) were assayed in a side-by-side analysis at Cerep Contract Laboratories (Cat. Refs. #44, 46 and 471). Results of receptor binding is listed in Table 4.

TABLE 4

Binding of Compounds to D1, D2 and 5-HT2a.

| Cmpd. | alternative human $D_1$ receptor binding ($K_i$) | alternative human $D_2$ receptor binding ($K_i$) | human 5-$HT_{2A}$ (IC$_{50}$) |
|---|---|---|---|
| (I) | 0.10 nM | 7.6 nM | 0.37 nM; 1.14 nM* |
| (II) | 0.20 nM | 6.8 nM | 1.1 nM |
| (III) | 0.36 nM | 7.6 nM | 1.1 nM |
| (IV) | 0.05 nM | 10 nM | 0.25 nM |
| (V) | 0.10 nM | 4.8 nM | 0.61 nM |
| (VI) | 0.10 nM | 3.7 nM | 0.24 nM |
| (VII) | 0.14 nM | 5.2 nM | 0.33 nM |
| (X) | 0.22 nM | 7 nM | 0.79 nM |

*Compound (I) was tested twice in this assay.

Example 10

Metabolism Investigations in Pooled Human Liver Microsomes (HLM)

Pooled human liver microsomes (50 donors, from Xenotech) were incubated with 1 microM or 10 microM of compound at 37° C. The incubation mixture contained 50 mM Tris-HCl, 154 mM KCl, 5 mM MgCl$_2$ and a NADPH regenerating system (1 mM NADP 5 mM isocitric acid, 1 unit/mL isocitric dehydrogenase, from Sigma-Aldrich). The protein concentration was 0.2 mg/mL and the final volume was 0.5 mL. Following a 10 minute pre-incubation, the reaction was initiated by adding Compound. After 0, 15, 30, 60, 90, 120 and 180 minutes, the reactions were terminated by transferring the subcellular fraction to 0.5 mL of stopping reagent containing internal standard. The incubations were carried out in triplicate. The samples were centrifuged at 4000 g (4° C., 15 min) and the supernatants were analysed by HPLC-MS/MS. Data were expressed as MS area relative to an internal standard.

Figure 7:
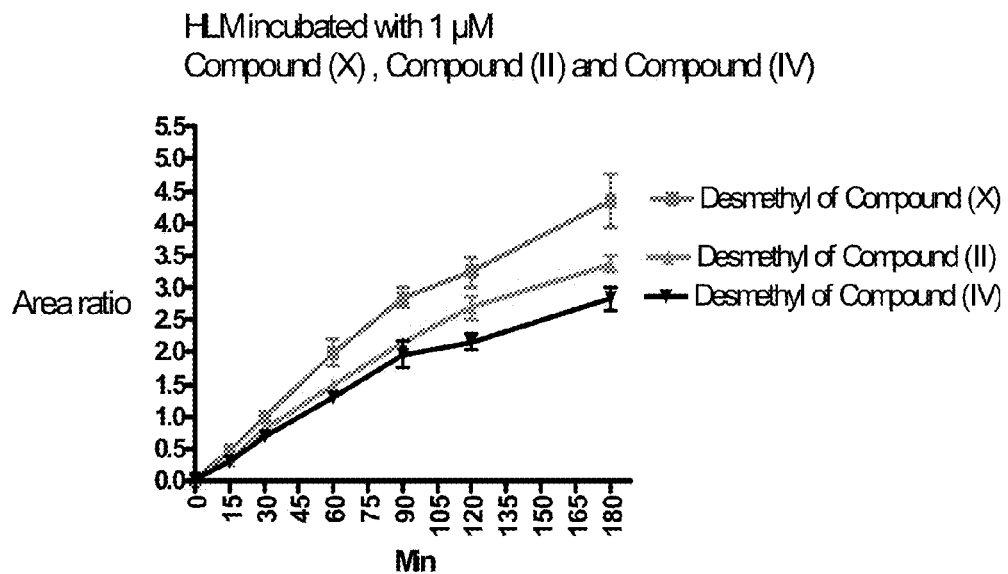
FIG. 7 shows formation of the desmethyl metabolite by metabolism of Compound (II), (IV) and (X) (1 micro M) in human liver microsomes (n=3, the bars represent standard deviation).
Figure 8:
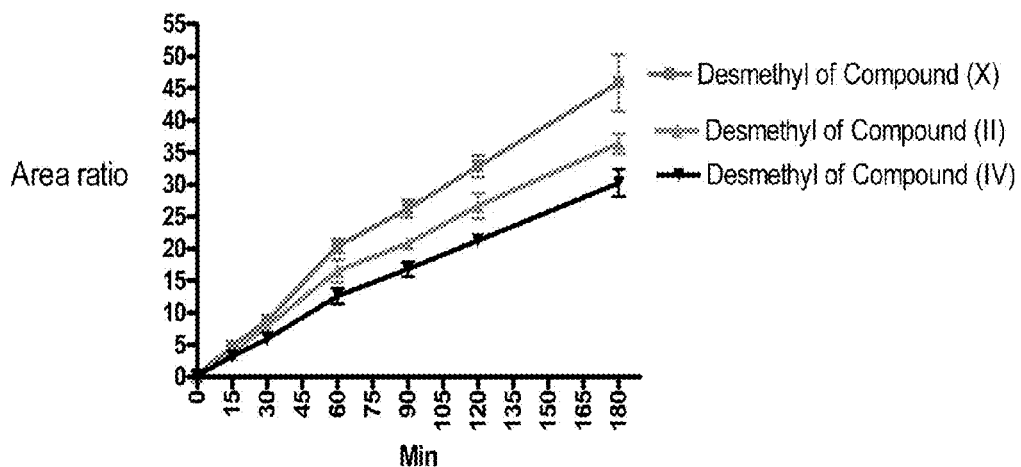
FIG. 8 shows formation of the desmethyl metabolite by metabolism of Compound (II), (IV) and (X) (10 micro M) in human liver microsomes (n=3, the bars represent standard deviation).
Figure 9:
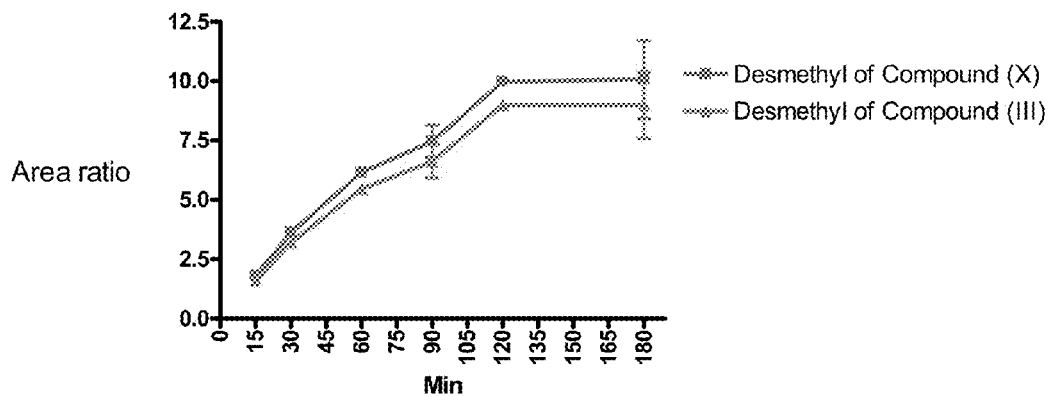
FIG. 9 shows formation of the desmethyl metabolite by metabolism of Compound (III) (10 micro M) in human liver microsomes (n=3, the bars represent standard deviation).
Figure 10:
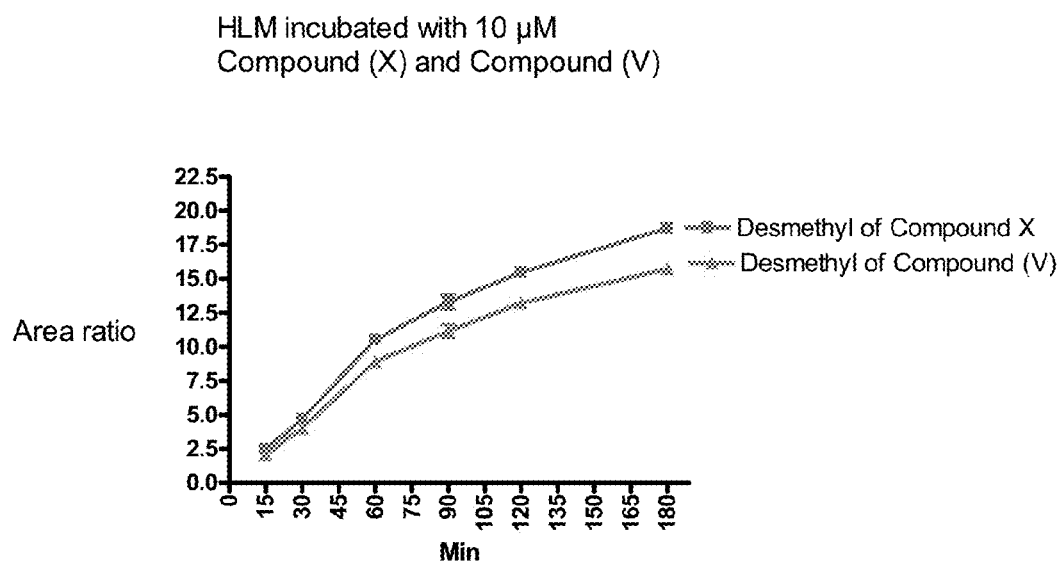
FIG. 10 shows formation of the desmethyl metabolite by metabolism of Compound (V) (10 micro M) in human liver microsomes (n=3, the bars represent standard deviation).
Figure 11:
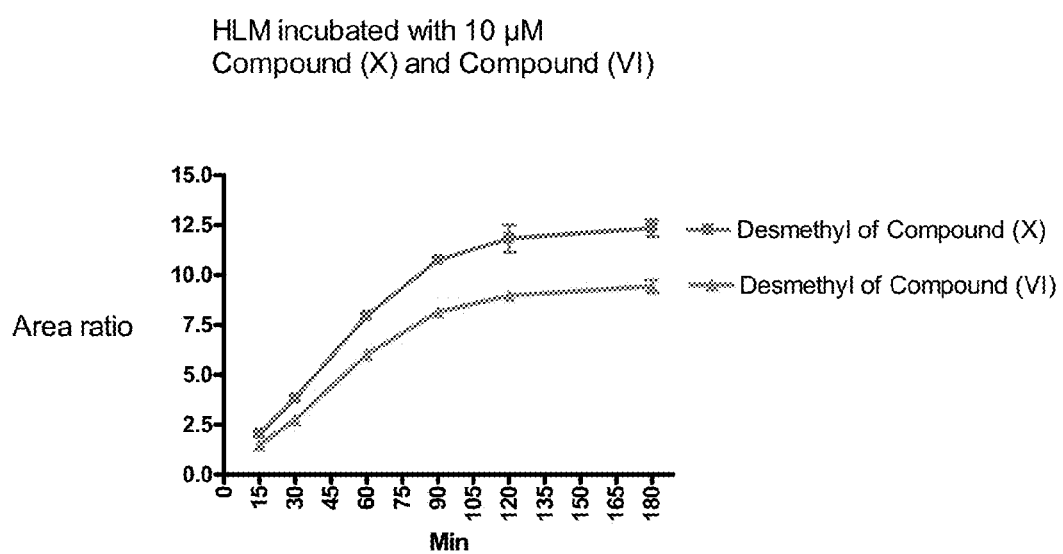
FIG. 11 shows formation of the desmethyl metabolite by metabolism of Compound (VI) (10 micro M) in human liver microsomes (n=3, the bars represent standard deviation).
Figure 12:
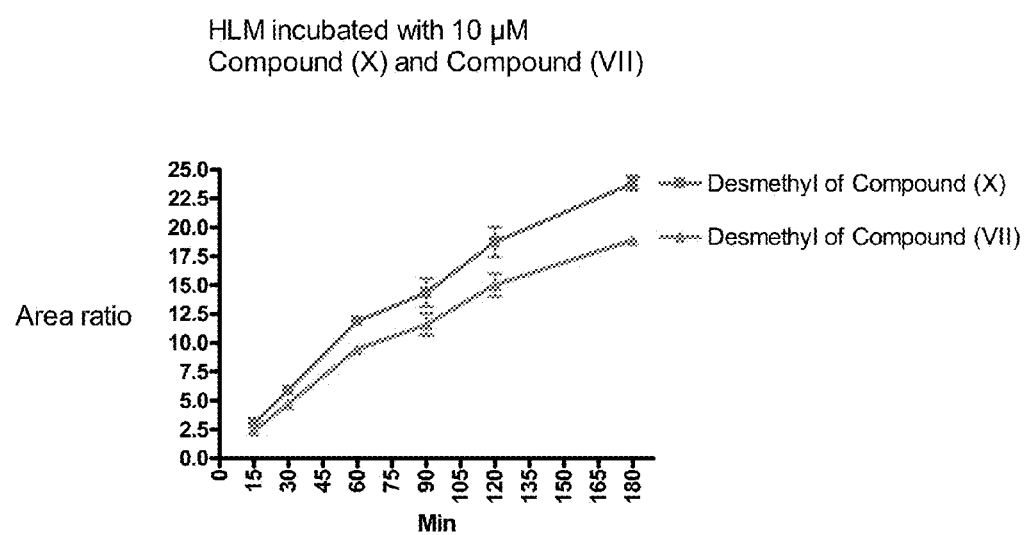
FIG. 12 shows formation of the desmethyl metabolite by metabolism of Compound (VII) (10 micro M) in human liver microsomes (n=3, the bars represent standard deviation).
Figure 13:
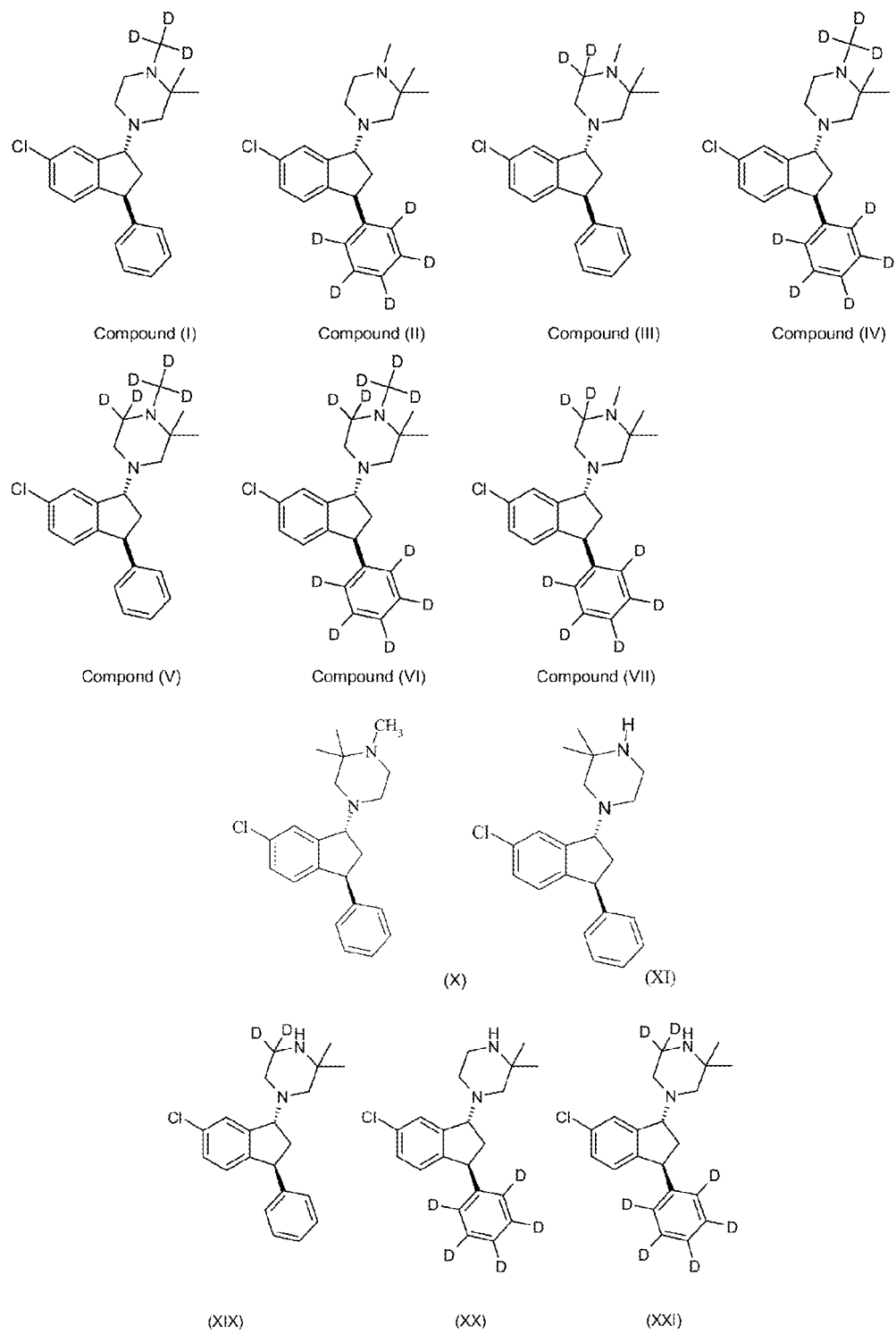
FIG. 13 shows the chemical structure of compounds (I)-(VII), (X)-(XI), and (XIX)-(XXI).

The results are shown as the mean of triplicate determinations±SD. FIG. 7 and FIG. 8 show that the amount of the desmethyl metabolite produced in human liver microsomes is lower from the deuterated form (Compound (II) and Compound (IV)) than from the non-deuterated compound (Compound (X)), both at a concentration of 1 microM (FIG. 7) and at a concentration of 10 microM (FIG. 8). Results for Compound (III) are shown in FIG. 9. Results for Compounds (V)-(VII) are shown in FIGS. 10-12, respectively. The desmethyl metabolites of compounds (II), (IV) and (X) are compounds (XX) and (XI), respectively (see FIG. 13).

Investigations Using Recombinant Human Liver CYP2C19 and CYP3A4

Recombinant human liver CYP2C19 or CYP3A4 isoenzymes (from BD biosciences) were incubated with 1 microM or 10 microM Compound (X), Compound (II) or Compound (IV) at 37° C. The incubation mixture contained 50 mM Tris-HCl, 154 mM KCl, 5 mM MgCl$_2$ and a NADPH regenerating system (1 mM NADP$^+$, 5 mM isocitric acid, 1 unit/mL isocitric dehydrogenase, from Sigma-Aldrich). The protein concentration was 0.5 mg/mL and the final volume was 0.5 mL. Following a 10 minutes pre-incubation, the reaction was initiated by adding Compound (X), Compound (II) and/or Compound (IV). After 0, 15, 30, 60, 90, 120 and 180 minutes the reactions were terminated by transferring the subcellular fraction to 0.5 mL of stopping reagent containing internal standard. The incubations were carried out in triplicate. The samples were centrifuged at 4000 g (4° C., 15 minutes) and the supernatants were analyzed by HPLC-MS/MS. Data were expressed as MS area relative to an internal standard.

Figure 14:
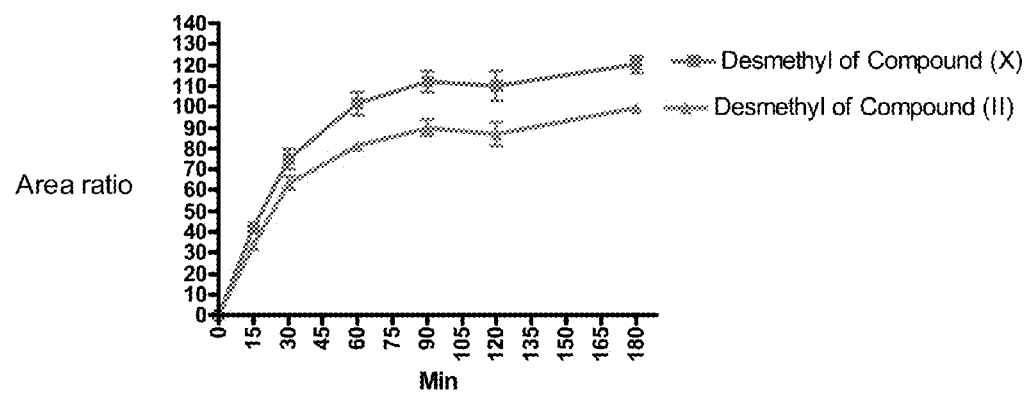
FIG. 14 shows formation of the desmethyl metabolite by metabolism of Compound (II) and (X) (10 micro M) by recombinant human liver CYP2C19 (n=3, the standard deviation).
Figure 15:
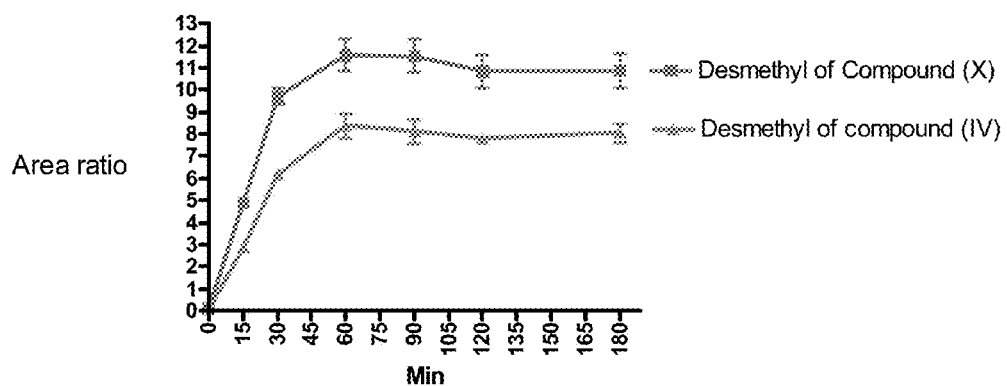
FIG. 15 shows formation of the desmethyl metabolite by metabolism of Compound (IV) and Compound (X) (1 micro M) by recombinant human liver CYP2C19 (n=3, the bars represent standard deviation).

The results (FIG. 14 and FIG. 15) show that the amount of the desmethyl metabolite produced following incubation with recombinant human liver CYP2C19 enzymes is lower from the deuterated forms (Compound (II) and Compound (IV)) than from the non-deuterated compound (Compound (X)), both at a concentration of 10 micro M (FIG. 14, Compound (II)) and at a concentration of 1 micro M (FIG. 15, Compound (IV)). Corresponding results were obtained for Compound (II) at a concentration of 1 micro M and for Compound (IV) at a concentration of 10 micro M.

Correspondingly, the amount of the desmethyl metabolite produced by incubation with recombinant human liver CYP3A4 enzymes is lower from the deuterated forms (Compound (II) and (IV)) than from the non-deuterated compound (Compound (X)), both at a concentration of 1 micro M and 10 micro M.

Example 11

Pharmacology of Compound (IV)

PCP-Induced Hyperactivity

Figure 16:
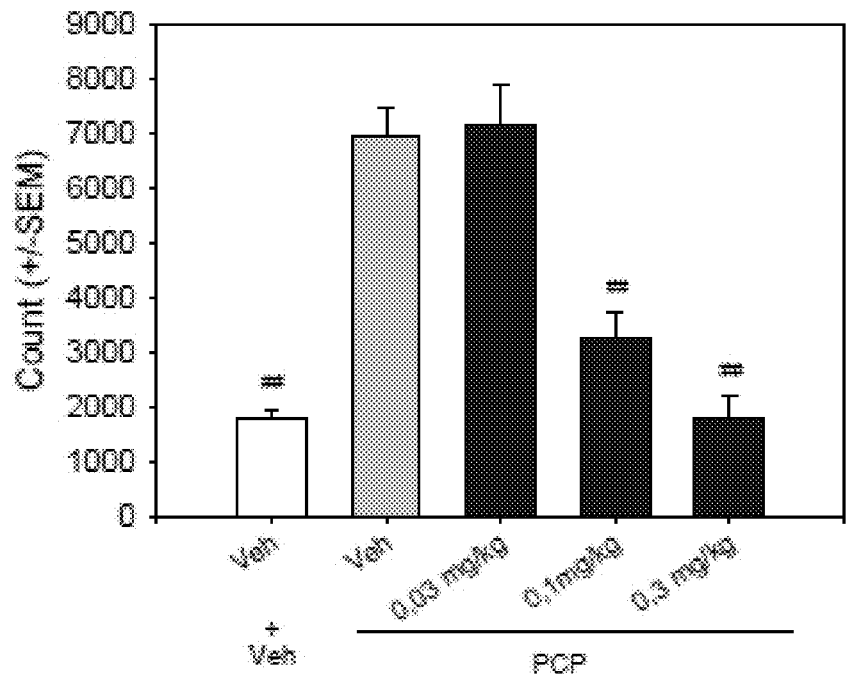
FIG. 16 shows PCP-induced hyperactivity in mice for compound (IV).

Compound (IV) dose-dependently reverses PCP-induced hyperactivity in mice, indicative of antipsychotic efficacy (FIG. 16). Compound (IV) hydrogen tartrate was administered subcutaneous (s.c.) 30 minutes before the test. PCP hydrochloride (2.3 mg/kg) was administered s.c. just before the test. Locomotor activity was measured for 60 minutes as number of beam breaks (counts). Eight to 16 male mice were used in each group. ## indicates P<0.01 versus Vehicle-PCP (One-way analysis of variance [ANOVA] followed by Bonferroni post-hoc test). PCP is blocking NMDA receptors and as such is used to model the hypo-glutamatergic state related to schizophrenia. PCP produces behavioural effects in animals reminiscent of positive, negative, and cognitive symptoms of schizophrenia patients (Jentsch, J. D. and Roth, R. H. *Neuropsychopharmacology* 1999; 20: 201-225; herein incorporated by reference in its entirety). PCP-induced hyperactivity is commonly used as an assay for evaluation of antipsychotic compounds (Jackson, D. M. et al., *Pharmacol Biochem Behav.* 1994; 48: 465-471; herein incorporated by reference in its entirety).

Catalepsy

Catalepsy is thought to reflect drug-induced suppression of the ability to initiate a behavioral response. The catalepsy test in rats is a common and widely used preclinical screening test for the EPS liability of potentially antipsychotic drugs. Although catalepsy is usually assessed following acute drug administration, the test has proven to be a reliable predictor for the propensity of an antipsychotic drug to induce EPS (that is, pseudo parkinsonism, dystonia) in humans (Elliott, P. J. et al, *J. Neural. Transm. Park. Dis. Dement. Sect.* 1990; 2: 79-89; herein incorporated by reference in its entirety).

Figure 17:
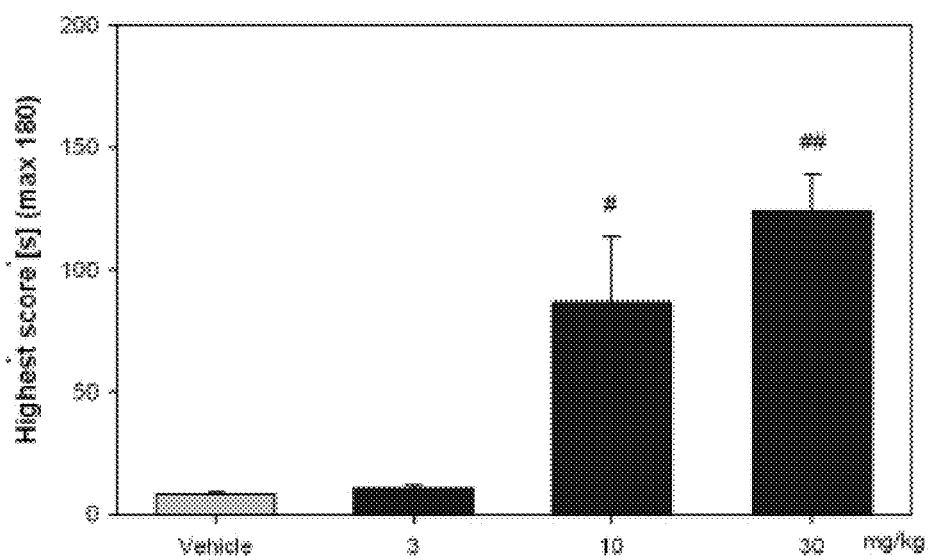
FIG. 17 shows cataleptic response in rats for compound (IV).

Compound (IV) dose-dependently induced catalepsy in rats suggestive of EPS liability. The minimal effective dose inducing catalepsy was 10 mg/kg (FIG. 17). Compound (IV) tartrate was administered s.c. 30 minutes before the test. Eight male Sprague Dawley rats were used in each group. # indicates P<0.05, ## indicates P<0.01 versus vehicle (One-way ANOVA followed by Bonferroni post-hoc test). This dose is 100 times higher than the dose indicating antipsychotic activity (FIG. 16).

Example 12

Human Pharmacokinetic Studies

The pharmacokinetics of Compound (IV) and Compound (X) were compared in a multiple oral dose study in healthy young men. The study participants received daily doses of 3 mg Compound (IV) and 3 mg Compound (X) for 18 days and blood samples were collected for 24 hours (one dosing interval) after the last dose to measure the exposure of both compounds and their demethylated metabolites, Compound (XX) and Compound (XI), respectively.

For all study participants, the area under the time-plasma concentration curve for the dosing interval (AUC 0-24) for Compound (IV) was higher than that for Compound (X), mean 104 h*ng/mL vs 98 h*ng/mL. A consistent shift in the opposite direction was observed for the demethylated metabolites with mean AUC 0-24 of 117 h*ng/mL and 120 h*ng/ml for Compound (XX) and Compound (XI), respectively.

Example 13

Catalytic Enantioselective Synthesis of Ketone Intermediate

This example discloses the synthesis of (S)-6-chloro-3-phenyl($d_5$)-indan-1-one, Compound (XV), and (S)-6-chloro-3-phenyl-indan-1-one, Compound (XVIII).

(S)-6-chloro-3-phenyl($d_5$)-indan-1-one, Compound (XV), has proven to be a valuable building block in the synthesis of deuterated variants of Compound (X) where the free phenyl group is deuterated.

General Experimental

Unless otherwise stated, all reactions were carried out under nitrogen. Reactions were monitored by thin-layer chromatography (TLC) analysis and LC-MS. All reagents were purchased and used without further purification. Spots were visualized by exposure to ultraviolet (UV) light (254 nm), or by staining with a 5% solution of phosphomolybdenic acid (PMA) in ethanol or basic aqueous potassium permanganate ($KMnO_4$) and then heating. Column chromatography was carried out using Merck C60 (40-63 μm, 230-240 mesh) silica gel. NMR spectra were recorded at 500 or 600 MHz ($^1H$ NMR), and calibrated to the residual solvent peak. The following abbreviations are used for NMR data: s, singlet; d, doublet; t, triplet; m, multiplet. Coupling constants are rounded to nearest 0.5 Hz. Enantiomeric excess was determined by chiral HPLC.

LC-MS Method:

Acquity UPLC BEH C18 1.7 μm column; 2.1×50 mm operating at 60° C. with flow 1.2 mL/min of a binary gradient consisting of water+0.1% formic acid (A) and acetonitrile+5% water+0.1% formic acid (B).

Chiral HPLC Method:

Phenomenex Lux 5μ Cellulose-2 column; 250×4.6 mm operating at 30° C. with flow 0.6 mL/min of n-hexane: isopropanol:diethylamine, 90:10:0.1.

Synthesis of (S)-6-chloro-3-phenyl($d_5$)-indan-1-one (Compound (XV)) (Scheme 14)

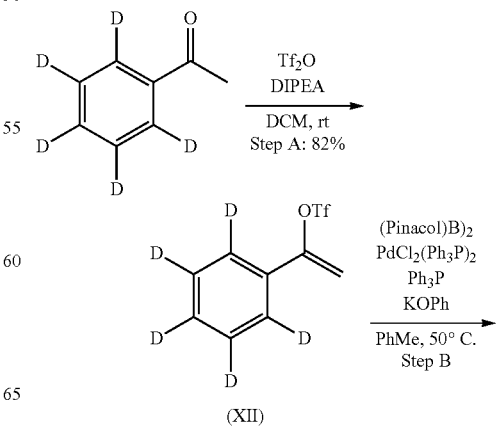

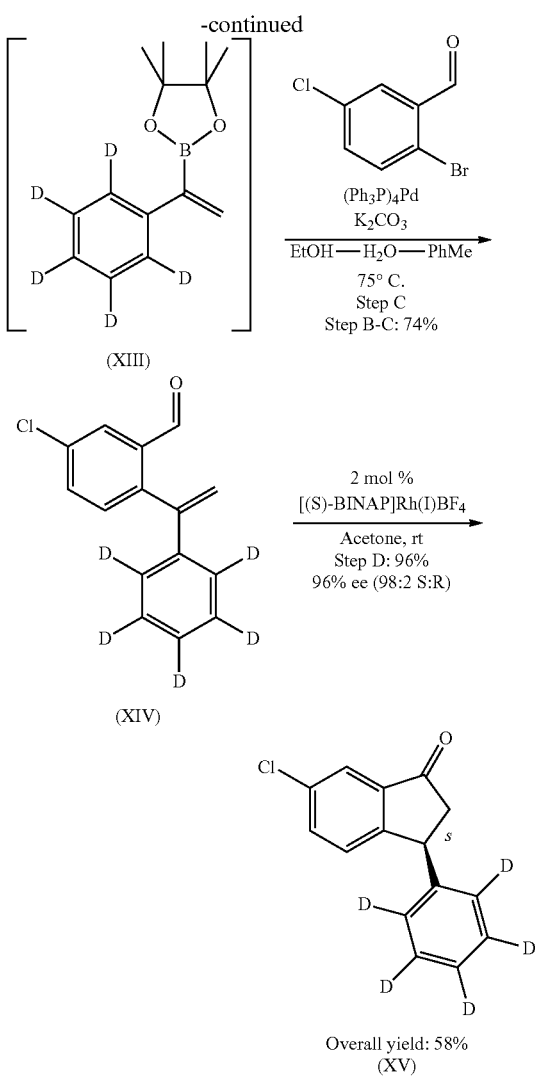

1-phenyl(d$_5$)-vinyl trifluoromethanesulfonate (XII)

To a solution of acetophenone-d$_5$ (1.56 g, 12.5 mmol) in CH$_2$Cl$_2$ (25.0 mL) was added trifluoromethanesulfonic anhydride (2.52 mL, 15.0 mmol) at room temperature. Then N,N-diisopropylethylamine (3.04 mL, 17.5 mmol) was added dropwise while the reaction mixture was cooled in an ice-water bath. The reaction mixture was allowed to warm to room temperature, and it was stirred for 1.5 h. Trifluoromethanesulfonic anhydride (0.63 mL, 3.74 mmol) was added followed by N,N-diisopropylethylamine (1.09 mL, 6.24 mmol). The reaction mixture was stirred for 2 hours at room temperature. Toluene (25 mL) and silica gel (5 g) was added. The mixture was concentrated in vacuo, and the resulting suspension was filtered through a pad of celite. The filter cake was washed with toluene (10 mL), and the filtrate was evaporated to dryness in vacuo to yield crude Compound (XII) (3.11 g, 82%, purity (NMR): approx. 85%) as a dark oil, that was used without further purification.

$^1$H NMR (600 MHz, CDCl$_3$) δ$_H$ 5.38 (d, 1H, J=4.0 Hz), 5.62 (d, 1H, J=4.0 Hz).

5-chloro-2-(1-phenyl(d$_5$)-vinyl)benzaldehyde (XIV) (Takagi, J.; Takahashi, K.; Ishiyama, T.; Miyaura, N. *J. Am. Chem. Soc.* 2002, 124, 8001-8006; Simeone, J. P.; Sowa, J. R. Jr. *Tetrahedron* 2007, 63, 12646-12654; each herein incorporated by reference in its entirety).

To a solution of Compound (XII) (3.11 g, 10.3 mmol, purity (NMR): approx. 85%) in toluene was added triphenylphosphine (108 mg, 0.685 mmol), bis(pinacolato)diboron (2.61 g, 10.3 mmol), bis(triphenylphosphine)palladium (II) chloride (240 mg, 0.342 mmol) and potassium phenolate (1.92 g, 14.6 mmol). The reaction mixture was stirred at 50° C. for 4 hours. This yielded Compound (XIII) in the mixture, which was not isolated. The mixture was cooled to room temperature, and ethanol (10 mL) and water (5 mL) was added, followed by tetrakis(triphenylphosphine)palladium (0) (495 mg, 0.428 mmol), potassium carbonate (4.73 g, 34.2 mmol) and 2-bromo-5-chlorobenzaldehyde (1.88 g, 8.56 mmol). The reaction mixture was stirred at 80° C. for 16 hours. The mixture was cooled to room temperature, and partitioned between water (50 mL) and toluene (50 mL).

The organic phase was separated and washed with water (50 mL) twice, and brine. The organic phase was dried over MgSO$_4$, filtered and evaporated to dryness in vacuo. The residue was subjected to purification by column chromatography eluting with 80:1 n-heptane:EtOAc mixture to afford Compound (XIV) (1.66 g, 74%) as an orange oil.

$^1$H NMR (600 MHz, CDCl$_3$) δ$_H$ 5.28 (d, 1H, J=0.5 Hz), 6.00 (d, 1H, J=0.5 Hz), 7.30 (d, 1H, J=8.0 Hz), 7.56 (dd, 1H; J=2.5, 8.0 Hz), 7.96 (d, 1H, J=2.5 Hz); $^{13}$C NMR (150 MHz, CDCl$_3$) δ$_C$ 118.7, 126.6 (t, J=24.0 Hz), 127.5, 128.2 (t, J=24.0 Hz), 128.4 (t, J=24.0 Hz), 132.5, 133.7, 134.7, 135.7, 140.3, 143.9, 144.8, 190.8; LC-MS (APPI): m/e calc. for C$_{15}$H$_7$D$_5$ClO [M+H]$^+$ 248.1. found 248.1.

(S)-6-Chloro-3-phenyl(d$_5$)-indan-1-one (XV) (Kundu, K.; McCullagh, J. V.; Morehead, A. T. Jr. *J. Am. Chem. Soc.* 2005, 127, 16042-16043; herein incorporated by reference in its entirety).

Hydrogen was bubbled through a N$_2$-flushed solution of ((R)-2,2'-bis(diphenylphosphino)-1,1'-binaphthyl)(norbornadiene)rhodium(I) tetrafluoroborate (37 mg, 0.0404 mmol) in acetone (7.5 mL) for 10 min at room temperature, during which the color of the solution changed from orange to more brownish red. The flask containing the solution was subsequently flushed briefly with N$_2$ gas. Then a solution of (XIV) (526 mg, 2.02 mmol, purity (LC-MS): 95%) in acetone (7.5 mL) was added at room temperature. The reaction mixture was stirred for 24 hours at room temperature. The reaction mixture was mixed with silica gel and evaporated to dryness in vacuo. The obtained material was loaded onto a silica gel column and the product was eluted with 10:1 n-heptane: EtOAc mixture to obtain Compound (XV) (495 mg, 96%, 96.0% ee) as a solid.

$^1$H NMR (500 MHz, CDCl$_3$) δ$_H$ 2.72 (dd, 1H, J=4.0, 19.5 Hz), 3.27 (dd, 1H, J=8.0, 19.5 Hz), 4.55 (dd, 1H, J=4.0, 8.0 Hz), 7.21 (d, 1H; J=8.0 Hz), 7.52 (dd, 1H, J=2.0, 8.0 Hz), 7.77 (d, 1H, J=2.0 Hz); $^{13}$C NMR (125 MHz, CDCl$_3$) δ$_C$ 44.0, 47.2, 123.2, 126.8 (t, J=24.0 Hz), 127.3 (t, J=24.0 Hz), 128.7 (t, J=24.0 Hz), 134.4, 135.1, 138.2, 142.9, 156.0, 206.4; LC-MS (APPI): m/e calc. for C$_{15}$H$_7$D$_5$ClO [M+H]$^+$ 248.1. found 247.6.

Synthesis of (S)-6-chloro-3-phenyl-indan-1-one (XVIII) (Scheme 15)

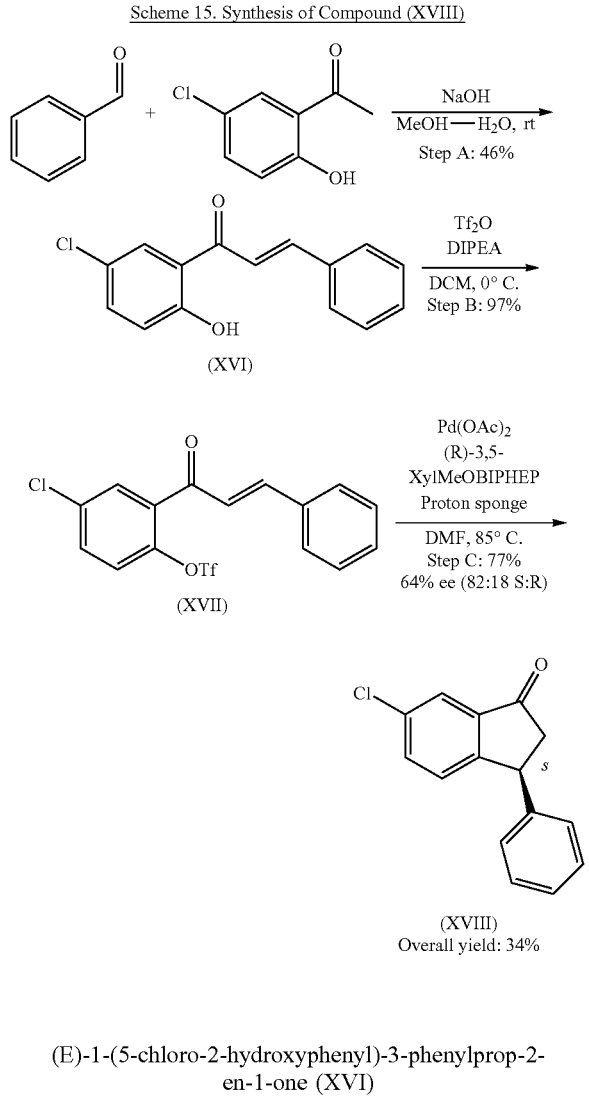

(E)-1-(5-chloro-2-hydroxyphenyl)-3-phenylprop-2-en-1-one (XVI)

To an ice-cooled solution of sodium hydroxide (2.34 g, 58.6 mmol) in water (17.0 mL) was added benzaldehyde (0.746 g, 7.03 mmol) and then a solution of 5-chloro-2-hydroxyacetophenone (1.00 g, 5.86 mmol) in methanol (17.0 mL). The reaction mixture was allowed to warm to room temperature, and it was stirred for 24 hours. The bulk of the organic solvent was removed by evaporation in vacuo. The aqueous residue was extracted with EtOAc (3×30 mL). The combined extracts were washed with water (50 mL) and brine (50 mL), dried over MgSO$_4$, filtered and evaporated to dryness in vacuo. The residue was dissolved in a minimum volume of CH$_2$Cl$_2$, and n-pentane was added which resulted in precipitation. The obtained suspension was filtered and the precipitate was washed with little cold pentane, and dried in vacuo to afford Compound (XVI) (695 mg, 46%) as an orange solid.

$^1$H NMR (500 MHz, CDCl$_3$) $\delta_H$ 6.22 (d, 1H, J=9.0 Hz), 6.80 (dd, 1H, J=3.0, 9.0 Hz), 7.33 (t, 1H, J=7.5 Hz), 7.38-7.42 (m, 4H), 7.60 (d, 2H, J=7.5 Hz); 8.63 (d, 1H, J=16.0 Hz); $^{13}$C NMR (125 MHz, CDCl$_3$) $\delta_C$ 110.6, 125.2, 127.8, 128.1, 128.8, 128.9, 129.4, 129.6, 1'33.0, 136.4, 137.1, 174.5, 188.2.

Trifluoromethanesulfonic acid 4-chloro-2-((E)-(3-phenyl-acryloyl))-phenyl ester (XVII)

To a solution of Compound (XVI) (517 mg, 2.00 mmol) in CH$_2$Cl$_2$ (10.0 mL) was added N,N-diisopropylethylamine (697 μL, 4.00 mmol). Trifluoromethanesulfonic anhydride (437 μL, 2.60 mmol) was added dropwise at 0° C. The reaction mixture was stirred for 45 min at 0° C. Sat. aq. NH$_4$Cl (5 mL) and water (10 mL) was added, and the mixture was stirred for 5 minutes. The organic phase was separated, and the aqueous phase was extracted with CH$_2$Cl$_2$ (10 mL). The combined extracts were dried over MgSO$_4$, filtered and evaporated to dryness in vacuo. The residue was purified by column chromatography eluting with 4:1 n-heptane:EtOAc to yield (XVII) (757 mg, 97%) as an oil.

$^1$H NMR (500 MHz, CDCl$_3$) $\delta_H$ 7.16 (d, 1H, J=16.0 Hz), 7.34 (d, 1H, J=9.0 Hz), 7.40-7.47 (m, 3H), 7.57 (dd, 1H, J=2.5, 9.0 Hz), 7.60-7.62 (m, 2H), 7.69 (d, 1H, 16.0 Hz), 7.72 (d, 1H, J=2.5 Hz); $^{13}$C NMR (125 MHz, CDCl$_3$) $\delta_C$ 124.1, 124.2, 129.0, 129.2, 130.7, 131.5, 132.8, 134.1, 134.6, 145.2, 147.8, 188.4.

(S)-6-Chloro-3-phenyl-indan-1-one (XVIII) (Minatti, A.; Zheng, X.; Buchwald, S. L. *J. Org. Chem.* 2007, 72, 9253-9258; herein incorporated by reference in its entirety).

To a solution of Compound (XVII) (195 mg, 0.500 mmol) in DMF (2.0 mL) was added proton-sponge (214 mg, 1.00 mmol), palladium acetate (6 mg, 0.025 mmol) and (R)-3,5-XylMeOBIPHEP (35 mg, 0.05 mmol) at rt. The reaction mixture was stirred at 85° C. for 45 h. The mixture was cooled to rt, and diluted with TBME (15 mL). The mixture was washed three times with water (3×20 mL), and the organic phase was dried over MgSO$_4$, filtered and evaporated to dryness in vacuo. The residue was subjected to column chromatography eluting with 10:1 n-heptane:EtOAc to yield Compound (XVII) (94 mg, 77%, 64.0% ee).

$^1$H NMR (600 MHz, CDCl$_3$) $\delta_H$ 2.71 (dd, 1H, J=4.0, 19.5 Hz), 3.25 (dd, 1H, J=8.0, 19.5 Hz), 4.54 (dd, 1H, J=4.0, 8.0 Hz), 7.10 (d, 2H, J=7.0 Hz), 7.20 (d, 1H, J=8.0 Hz), 7.25 (t, 1H, J=7.5 Hz), 7.31 (t, 2H, J=7.5 Hz), 7.50 (dd, 1H, J=2.0, 8.0 Hz), 7.75 (d, 2H, J=2.0 Hz); $^{13}$C NMR (150 MHz, CDCl$_3$) $\delta_C$ 44.1, 47.2, 123.3, 127.3, 127.6, 128.3, 129.1, 134.4, 135.2, 138.3, 143.1, 156.1, 204.5.

Enantioenrichment of Compound (XVIII) by Reprecipitation

Compound (XVII) (940 mg, 3.87 mmol, 96% ee) was dissolved in a minimum volume of boiling ethanol (99% v/v). The resulting solution was allowed to cool slowly to rt by placing the glass flask containing the solution in the air. A precipitate formed that was filtered from solution to yield Compound (XVIII) (700 mg, 99.9% ee, 74%). A second crop of Compound (XVIII) could be obtained by cooling the filtrate in the freezer (−8° C.) to yield Compound (XVIII) (80 mg, 98.6% ee, 9%).

Analytical data (NMR and LC-MS) for Compound (XVIII) were the same as those reported above.

Example 14

Large Scale Production of Compound (IV)

The following process was developed for the large scale production of the hydrogen tartrate salt of Compound (IV).

Scheme 16: Synthesis of rac-trans-1-(6-Chloro-3-phenyl(d$_5$)-indan-1-yl)-3,3-dimethyl-piperazine maleate

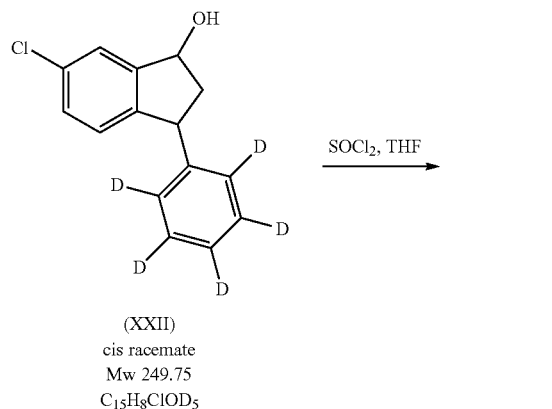

(XXII)
cis racemate
Mw 249.75
C$_{15}$H$_8$ClOD$_5$

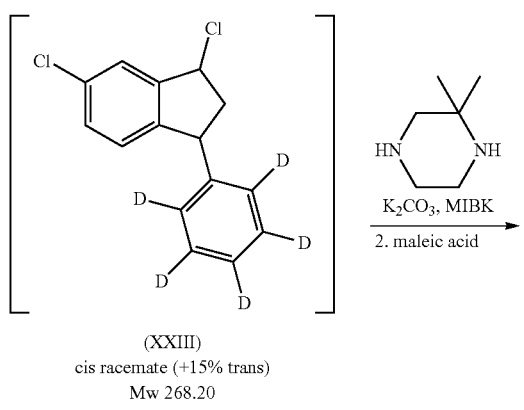

(XXIII)
cis racemate (+15% trans)
Mw 268.20
C$_{15}$H$_7$Cl$_2$D$_5$

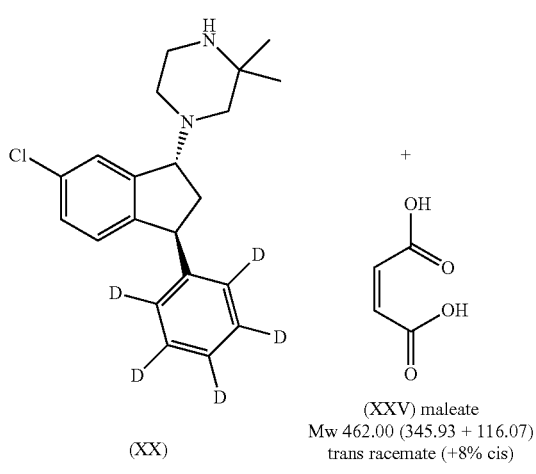

(XX)

(XXV) maleate
Mw 462.00 (345.93 + 116.07)
trans racemate (+8% cis)

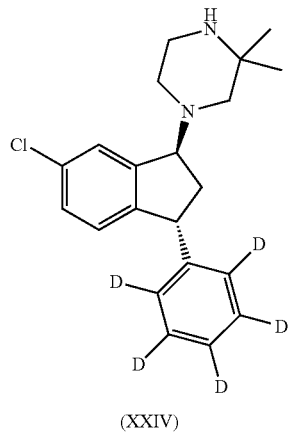

(XXIV)

Procedure:

1.) 2.01 kg (16.9 mol) thionylchloride and 7.2 kg tetrahydrofuran are mixed and the reaction is cooled to 10-15° C.
2.) a solution of 2.76 kg (11.1 mol) (XXII) in 7.2 kg THF is slowly added and after completion 5.9 kg tetrahydrofuran is added
3.) the reaction is stirred at 15° C. for approximately 90 hours
4.) 16.7 kg water is cooled to 11° C. and added slowly to the reaction, afterwards 7.8 kg 27.7% aqueous sodium hydroxide is added slowly, followed by 10 kg ethylacetate
5.) the mixture is stirred for 20-40 minutes
6.) the phases are separated and the organic phase is reduced to a volume of approximately 6 L
7.) 16 kg methyl isobutylketone is added and the volume is reduced to approximately 8 L
8.) 1.58 kg (11.4 mol) potassium carbonate, 1.69 kg (14.8 mol) 2,2-dimethylpiperazin and 13.6 kg methyl isobutyl ketone are added
9.) the reaction is stirred 35 hours at 90-95° C.
10.) after cooling to room temperature 11 kg water is added and the mixture is stirred for 30-60 minutes
11.) the phases are separated. 13.7 kg water is added to the organic phase and the mixture is stirred slowly for 30-60 minutes
12.) the phases are separated and the organic phase is blank filtered
13.) 5 kg methyl isobutyl ketone, 7.8 kg water and 5.9 kg 36% aqueous hydrogen chloride are added and the mixture is stirred at 50° C. for 30-60 minutes
14.) the phases are separated. 8 kg methyl isobutyl ketone is added to the water phase and the mixture is cooled to 10-15° C.
15.) a mixture of 3.5 kg methyl isobutyl ketone and 7.8 kg 25% aqueous ammonia are slowly added to the mixture and the reaction is stirred at 20-25° C. for 60-90 minutes
16.) the phases are separated and the organic phase is washed with 10.5 kg water 17.) the organic phase is reduced to 8 L 18.) 1.19 kg (10.25 mol) maleic acid and 9 kg methyl isobutyl ketone are added and the reaction is afterwards warmed to 75-80° C.

19.) after cooling to 10-15° C. the precipitate is filtered off and washed with 10 kg methyl isobutyl ketone 20.) the solid is dried in a vacuum oven at 50° C. for approximately 20 hours to give 3.47 kg (68% yield) of (XXV) maleate.

NMR Data for (XXV) Maleate:

1H-NMR (dmso-d6, 600 MHz, ppm): 8.60 (bs, 2H, maleic acid), 7.39 (d, 1H, J=1.6 Hz), 7.29 (dd, 1H, J=8.0 Hz, J=1.8 Hz), 6.98 (d, 1H, J=8.2 Hz), 6.04 (s, 2H, maleic acid), 4.56 (dd, 1H, J=8.1 Hz, J=4.9 Hz), 4.48 (dd, 1H, J=8.6 Hz, J=6.2 Hz), 3.37 (bs, 1H), 3.16 (bs, 2H), 2.77 (bs, 1H), 2.58-2.50 (m, 3H), 2.31 (d, 1H, J=12.0 Hz), 2.12 (ddd, 1H, J=13.8 Hz, J=8.0 Hz, J=6.0 Hz), 1.33 (s, 3H), 1.31 (s, 3H).

Scheme 17: Synthesis of rac-trans-1-(6-chloro-3-phenyl(d5)-indan-1-yl)-1(d3), 2,2-trimethyl-piperazine succinate

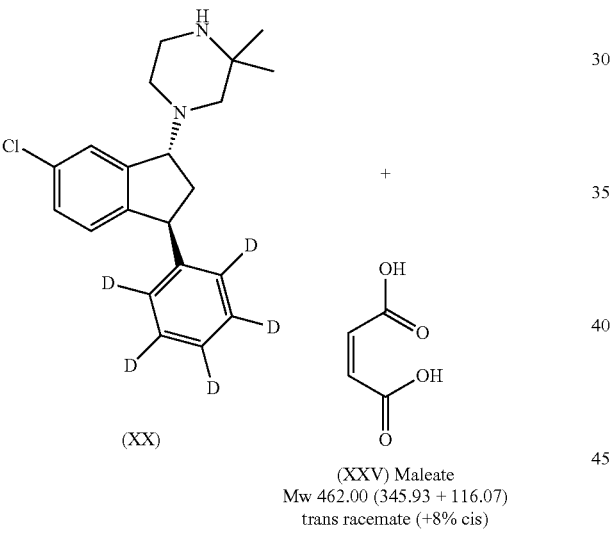

(XX)

(XXV) Maleate
Mw 462.00 (345.93 + 116.07)
trans racemate (+8% cis)

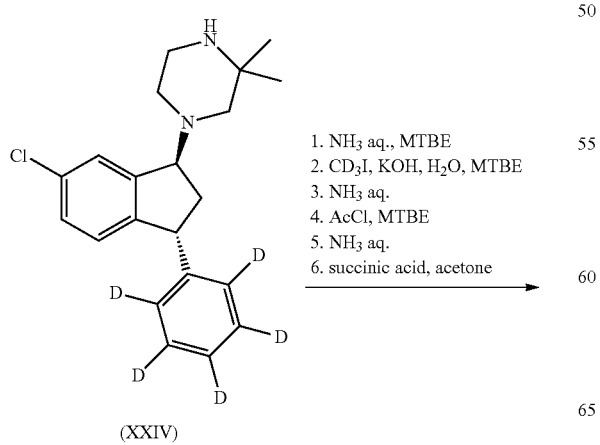

(XXIV)

1. NH3 aq., MTBE
2. CD3I, KOH, H2O, MTBE
3. NH3 aq.
4. AcCl, MTBE
5. NH3 aq.
6. succinic acid, acetone

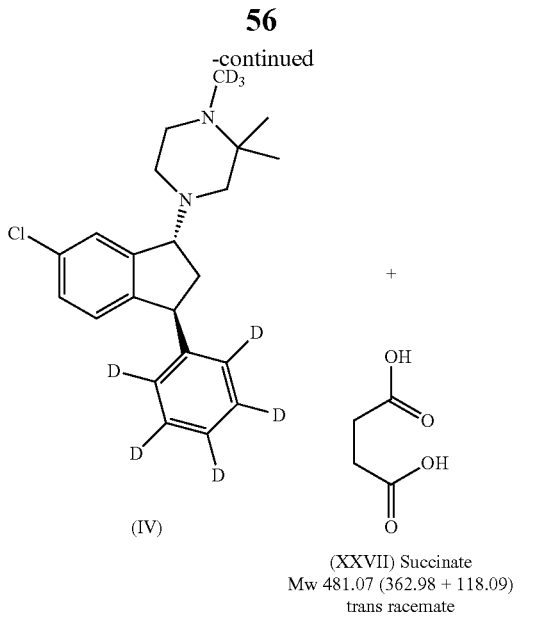

(IV)

(XXVII) Succinate
Mw 481.07 (362.98 + 118.09)
trans racemate (XXVI)

Procedure:

1.) 1.1 kg (2.38 mol) (XXV) maleate, 11 L methyl tertbutyl ether, 1.8 L water and 1 L 25% aqueous ammonia are stirred for 1-2 hours 2.) the phases are separated and the organic phase is washed with two times 2 L water 3.) a solution of 254 g (3.85 mol) 85% aqueous potassium hydroxide and 1.5 L water is added to the organic phase, followed by addition of 450 g (3.11 mol) methyl (d3)iodide (CD3I)

4.) the reaction is stirred at 20-25° C. for 16-24 hours

5.) 2 L water are added and the precipitating by-product is filtered off

6.) 0.8 L water and 0.2 L 25% aqueous ammonia are added to the filtrate and the mixture is stirred for 20-40 minutes 7.) the phases are separated and the organic phase is washed with 2 L water 8.) the phases are separated and 38 g (0.48 mol) acetylchloride is added to the organic phase which is stirred for 20-40 minutes 9.) 0.8 L water and 0.2 L 25% aqueous ammonia are added and the mixture is stirred for 20-40 minutes 10.) the phases are separated and the organic phase is washed with 2 L water 11.) the organic phase is reduced to dryness and acetone is added 12.) 225 g (1.91 mol) succinic acid and acetone are added so that the reaction volume is approximately 6-6.5 L 13.) The reaction is warmed to reflux and afterwards cooled to 5-10° C.

14.) The precipitate is filtered off and washed with 1 L acetone

15.) the solid is dried in a vacuum oven at 50° C. for more than 16 hours to give 630 g (55% yield) of (XXVII) succinate.

NMR Data for (XXVII) Succinate:

1H-NMR (dmso-d6, 600 MHz, ppm): 7.33 (d, 1H, J=1.9 Hz), 7.26 (dd, 1H, J=8.1 Hz, J=2.0 Hz), 6.95 (d, 1H, J=8.0 Hz), 4.46 (dd, 1H, J=8.0 Hz, J=5.1 Hz), 4.46 (dd, 1H, J=8.8 Hz, J=5.8 Hz), 2.65-2.56 (m, 4H), 2.46-2.41 (m, 1H), 2.37 (s, 4H, succinic acid), 2.31 (bs, 1H), 2.13 (d, 1H, J=10.9 Hz), 2.02 (ddd, 1H, J=13.7 Hz, J=7.8 Hz, J=6.0 Hz), 1.04 (s, 3H), 1.02 (s, 3H).

Scheme 18: Synthesis of 4-((1R,3S)-6-chloro-3-phenyl(d5)-indan-1-yl)-1(d3),2,2-trimethyl-piperazine L(+)-hydrogen tartrate.

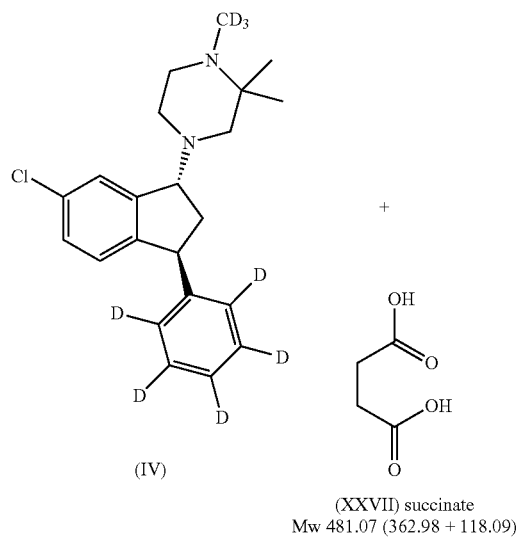

(IV)

(XXVII) succinate
Mw 481.07 (362.98 + 118.09)

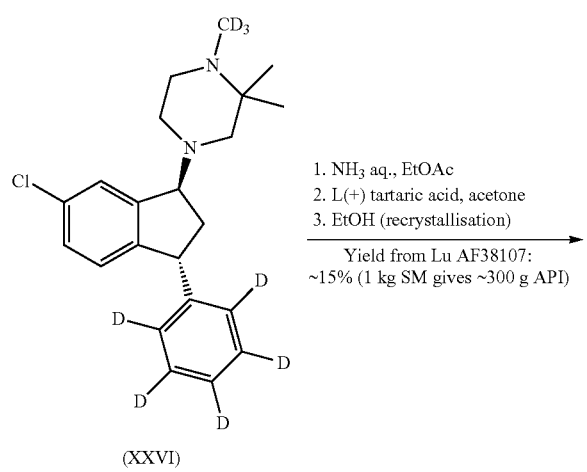

1. NH3 aq., EtOAc
2. L(+) tartaric acid, acetone
3. EtOH (recrystallisation)

Yield from Lu AF38107:
~15% (1 kg SM gives ~300 g API)

(XXVI)

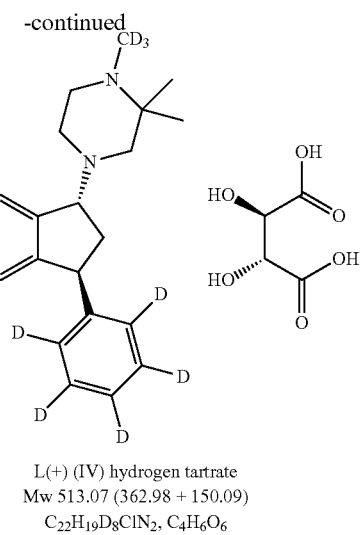

L(+) (IV) hydrogen tartrate
Mw 513.07 (362.98 + 150.09)
$C_{22}H_{19}D_8ClN_2, C_4H_6O_6$ Procedure:

1.) 1.0 kg (2.08 mol) (XXVII) succinate, 8 L ethyl acetate, 2 L water and 1 L 25% aqueous ammonia are stirred for 0.5-1 hours 2.) the phases are separated and the organic phase is washed with 2 L water 3.) the organic phase is reduced to approximately 1.5 L 4.) 10 L acetone and 312 g (2.08 mol) L(+)-tartaric acid are added 5.) the reaction is warmed to reflux and afterwards cooled to 5-10° C.

6.) the precipitate is filtered off, washed with 1.2 L acetone

7.) the wet filtercake is recharged and 11 L absolute ethanol are added

8.) the reaction is warmed to reflux and afterwards cooled to 5-10° C.

9.) the precipitate is filtered off and washed with 1.2 L absolute ethanol

10.) the solid is dried in a vacuum oven at 50° C. for more than 16 hours to give 395 g (37% yield) of (IV) L(+)-hydrogen tartrate.

NMR Data for (IV) L(+)-Hydrogen Tartrate:

1H-NMR (dmso-d6, 600 MHz, ppm): 7.36 (s, 1H), 7.27 (d, 1H, J=8.2 Hz), 6.96 (d, 1H, J=8.2 Hz), 4.50 (dd, 1H, J=8.0 Hz, J=5.1 Hz), 4.45 (dd, 1H, J=8.5 Hz, J=5.8 Hz), 4.07 (s, 2H, tartrate), 2.95 (bs, 1H), 2.77 (bs, 1H), 2.61-2.50 (m, 3H), 2.31 (d, 1H, J=11.7 Hz), 2.04 (ddd, 1H, J=13.7 Hz, J=7.8 Hz, J=6.0 Hz) 1.21 (s, 3H), 1.18 (s, 3H).

Example 15

Physico-Chemical Characterization of Salts of Compound (IV)

$pK_a$ and Log P/D of Compound (IV)

$pK_a$ was determined by potentiometric titration of the base at ion strength 0.16 using MeOH as co-solvent. Three series of three repeated titrations on the same solution of the sample was performed in a conventional way from low to high pH and a difference curve was created from each of these titrations by blank subtraction. The apparent $pK_a$-value at each MeOH:water ratio is calculated from the difference curves, and the $pK_a$ value is determined by extrapolation to zero MeOH content.

The lower $pK_a$ value is too low to be determined by potentiometric titration as data only were found reliable down to ~3. The high $pK_a$ was determined to be 8.9±0.1.

The lower $pK_a$ was determined by Dip Probe Absorption Spectroscopy detection during titration of the base at ion strength 0.16 using MeOH as co-solvent. The change in absorption spectra as a function of ionisation is used to calculate the $pK_a$-value. Two series of three repeated titrations on the same solution of the sample was performed from low to high pH, with a photo diode array as additional detection. The apparent $pK_a$ value at each MeOH:water ratio is calculated by Target factor analysis on the change in absorption spectra, and the $pK_a$ value is determined by extrapolation to zero MeOH content.

Result: The lower $pK_a$ was determined to be 2.5±0.1.

The log D profile was determined by titration at 27° C. and ion strength of approx. 0.16. A series of three repeated titrations on the same sample in solution was performed, from low to high pH. The first titration was performed with a small amount of n-octanol present in the solution, the second and third with increasing amounts.

A difference curve was created from each of these titrations by blank subtraction, and from these difference curves, the apparent $pK_a$ values ($p_oK_a$) were calculated. From the change in the apparent $pK_a$ values ($\Delta pK_a$) with the n-octanol:water ratio combined with the real $pK_a$ value, the Log P value was calculated and the Log D profile was derived. The following values were determined: Log P=5.4±0.4 and Log $D_{7.4}$=3.9±0.4.

Melting Point Determined by DSC

The melting point of the (R,R)-hydrogen tartrate salt of Compound (IV) was determined using differential scanning calorimetry (DSC), using a TA instruments DSC Q1000 heating the sample 5°/minute. The sample was placed in a covered pan with a punched pinhole.

The melting is characterized by onset and peak temperature of the melting endotherm, and the enthalpy of fusion is calculated from the area of the peak. Based on the DSC thermogram an onset temperature of 187.4° C. and a peak maximum at 189.4° C. was found. The enthalpy of fusion was 96 J/g corresponding to 49 kJ/mol, however the thermogram is indicative that the melting happens under decomposition meaning that the enthalpy probably contain energy other than melting.

Solubility

Solubility of the (R,R)-hydrogen tartrate salt of Compound (IV) was measured in aqueous solutions and in cyclodextrins with the following results (Table 5):

TABLE 5

Solubility of (R,R)-hydrogen tartrate salt of Compound (IV).

| Solvent | Meas. conc. (mg base/ml) | pH |
|---|---|---|
| Hydrogen tartrate in water, 5° C. | 3.1 | 3.25 |
| Hydrogen tartrate in water, RT | 4.0 | 3.15 |
| Hydrogen tartrate in water, 37° C. | 6.6 | 3.08 |
| 10% HPβCD | 25.2 | 3.59 |
| 5% HPβCD, at RT | 15.5 | 3.61 |
| 5% HPβCD, at 5° C. | 12 | |

Polymorphism

One solvent free crystal form of the hydrogen tartrate has been isolated. The XRPD of this form is shown in FIG. 18, and designated herein as "polymorph A".

Salts of Compound (IV)

Four salts were prepared by precipitation of Compound (IV) from 99% EtOH.

Analytical data are given in the table below (Table 6).

TABLE 6

Data for salts of Compound (IV)

| Salt | DSC ($T_{onset}$ ° C.) | Solubility (mg/ml) | pH |
|---|---|---|---|
| Dihydrogen phosphate | Degradation at 250° C. | 1.4 | 4.67 |
| Hydrogen fumarate | 202.7° C. | 1.2 | 4.10 |
| Hydrogen maleate | 150.4° C. | 1.2 | 4.94 |
| Hydrogen malonate | 145.0° C. followed by degradation | 9.5 | 4.08 |
| Hydrogen tartrate | 187° C. | 4.0 | 3.15 |
| Base | 59.9 | 0.1 | 7.6 |

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and/or rearranged in various ways within the scope and spirit of the invention to produce further embodiments that are also within the scope of the invention. Those skilled in the art will recognize, or be able to ascertain, using no more than routine experimentation, numerous equivalents to the specific embodiments described specifically in this disclosure. Such equivalents are intended to be encompassed in the scope of the following claims.

What is claimed:

1. A hydrochloride salt of the following compound:

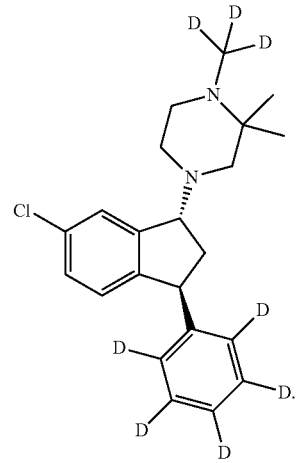

2. A hydrobromide salt of the following compound:
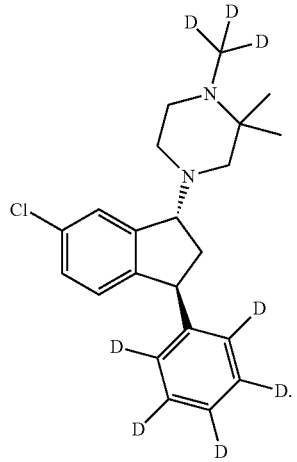
3. A hydroiodic salt of the following compound:
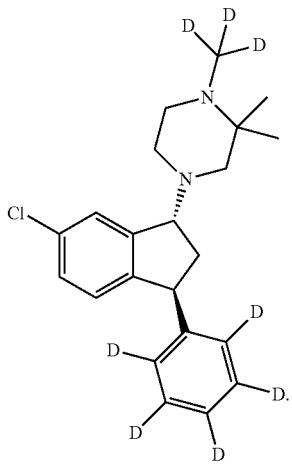
* * * * *